US008173370B2

(12) United States Patent
Oeth et al.

(10) Patent No.: US 8,173,370 B2
(45) Date of Patent: May 8, 2012

(54) NUCLEIC ACID-BASED TESTS FOR RHD TYPING, GENDER DETERMINATION AND NUCLEIC ACID QUANTIFICATION

(75) Inventors: Paul A. Oeth, San Diego, CA (US); Mathias Ehrich, San Diego, CA (US); Min S. Lee, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 0 days.

(21) Appl. No.: 12/027,954

(22) Filed: Feb. 7, 2008

(65) Prior Publication Data

US 2008/0299562 A1 Dec. 4, 2008

Related U.S. Application Data

(60) Provisional application No. 60/888,942, filed on Feb. 8, 2007.

(51) Int. Cl.
*C12Q 1/68* (2006.01)
*C12P 19/34* (2006.01)

(52) U.S. Cl. ........................ 435/6.12; 435/6.1; 435/6.11

(58) Field of Classification Search ........................ None
See application file for complete search history.

(56) References Cited

U.S. PATENT DOCUMENTS

| | | | |
|---|---|---|---|
| 4,656,127 | A | 4/1987 | Mundy |
| 4,683,195 | A | 7/1987 | Mullis |
| 4,683,202 | A | 7/1987 | Mullis |
| 4,851,331 | A | 7/1989 | Vary |
| 4,965,188 | A | 10/1990 | Mullis |
| 5,210,015 | A | 5/1993 | Gelfand |
| 5,487,972 | A | 1/1996 | Gelfand |
| 5,492,806 | A | 2/1996 | Drmanac |
| 5,525,464 | A | 6/1996 | Drmanac |
| 5,547,835 | A | 8/1996 | Koster |
| 5,589,330 | A | 12/1996 | Shuber |
| 5,605,798 | A | 2/1997 | Koster |
| 5,656,493 | A | 8/1997 | Mullis |
| 5,679,524 | A | 10/1997 | Nikiforov |
| 5,691,141 | A | 11/1997 | Koster |
| 5,695,940 | A | 12/1997 | Drmanac |
| 5,723,293 | A | 3/1998 | Huang |
| 5,834,189 | A | 11/1998 | Stevens |
| 5,849,483 | A | 12/1998 | Shuber |
| 5,849,542 | A | 12/1998 | Reeve |
| 5,851,770 | A | 12/1998 | Babon |
| 5,869,242 | A | 2/1999 | Kamb |
| 5,876,934 | A | 3/1999 | Duthie |
| 5,891,625 | A | 4/1999 | Buchardt |
| 5,908,755 | A | 6/1999 | Kumar |
| 5,912,118 | A | 6/1999 | Ansorge |
| 5,928,906 | A | 7/1999 | Koster |
| 5,952,174 | A | 9/1999 | Nikiforov |
| 5,958,692 | A | 9/1999 | Cotton |
| 5,976,802 | A | 11/1999 | Ansorge |
| 5,981,186 | A | 11/1999 | Gabe |
| 5,998,143 | A | 12/1999 | Ellis |
| 6,004,744 | A | 12/1999 | Goelet |
| 6,013,431 | A | 1/2000 | Soderlund |
| 6,013,499 | A | 1/2000 | Narumiya |
| 6,017,702 | A | 1/2000 | Lee |
| 6,018,041 | A | 1/2000 | Drmanac |
| 6,043,031 | A | 3/2000 | Koster |
| 6,045,996 | A | 4/2000 | Cronin |
| 6,046,005 | A | 4/2000 | Ju |
| 6,087,095 | A | 7/2000 | Rosenthal |
| 6,110,684 | A | 8/2000 | Kemper |
| 6,136,541 | A | 10/2000 | Gulati |
| 6,140,054 | A | 10/2000 | Wittwer |
| 6,142,681 | A | 11/2000 | Gulati |
| 6,156,501 | A | 12/2000 | McGall |
| 6,183,958 | B1 | 2/2001 | Stanton |
| 6,194,144 | B1 | 2/2001 | Koster |
| 6,197,506 | B1 | 3/2001 | Fodor |
| 6,210,891 | B1 | 4/2001 | Nyren |
| 6,223,127 | B1 | 4/2001 | Berno |
| 6,225,625 | B1 | 5/2001 | Pirrung |
| 6,229,911 | B1 | 5/2001 | Balaban |
| 6,239,273 | B1 | 5/2001 | Pease |
| 6,258,538 | B1 | 7/2001 | Koster |
| 7,005,276 | B1 | 2/2006 | Flegel et al. |
| 7,252,949 | B2 | 8/2007 | Flegel et al. |
| 7,553,629 | B2 | 6/2009 | Flegel et al. |

(Continued)

FOREIGN PATENT DOCUMENTS

JP 2004089057 3/2004

(Continued)

OTHER PUBLICATIONS

Wagner et al., "Molecular Basis of Weak D Phenotypes," Blood, 1999, vol. 93, pp. 385-393.*

Genbank Accession No. AC093428, authors Kaul et al., Jan 2002, pp. 1-40.*

Geifman-Holtzman et al., "Fetal RhD genotyping in fetal cells flow sorted from maternal blood," American Journal of Obstetrics and Gynecology, Mar. 1996, vol. 174, No. 3, pp. 818-822.*

Ekman et al., American Journal of Hematology, 2002, vol. 69, pp. 34-40.*

Beiboer et al., "Rapid genotyping of blood group antigens by multipex polymerase chain reaction and DNA microarray hybridization," Transfusion, May 2005, vol. 45, pp. 667-679.

Buck et al., "Design Strategies and Performance of Custom DNA Sequencing Primers," Biotechniques, Sep. 1999, vol. 27, No. 3, pp. 528-536.

Denomme et al., "High-throughput multiplex single-nucleotide polymorphism analysis for red cell and platelet antigen genotypes," Transfusion May 2005, vol. 45, pp. 660-666.

(Continued)

*Primary Examiner* — Young J Kim
(74) *Attorney, Agent, or Firm* — Grant Anderson LLP

(57) ABSTRACT

The invention in part provides nucleic acid-based assays, which are particularly useful for non-invasive prenatal testing. The invention in part provides compositions and methods for RhD typing, detecting the presence of fetal nucleic in a sample, determining the relative amount of fetal nucleic acid in a sample and determining the sex of a fetus, wherein each of the assays may be performed alone or in combination.

9 Claims, 19 Drawing Sheets

U.S. PATENT DOCUMENTS

| | | | |
|---|---|---|---|
| 2005/0079521 | A1 | 4/2005 | Beaulieu |
| 2008/0261205 | A1 | 10/2008 | Denomme |
| 2009/0186340 | A1 | 7/2009 | Olsson et al. |

FOREIGN PATENT DOCUMENTS

| | | | |
|---|---|---|---|
| JP | 2003513620 | * | 11/2005 |
| WO | WO 99/37763 | | 7/1999 |
| WO | WO 9937763 | A2 * | 7/1999 |
| WO | WO 00/52625 | | 9/2000 |
| WO | WO 01/20039 | | 3/2001 |
| WO | WO 01/25485 | | 4/2001 |
| WO | WO 01/27326 | | 4/2001 |
| WO | WO 01/27327 | | 4/2001 |
| WO | WO 01/27329 | | 4/2001 |
| WO | WO 01/29259 | | 4/2001 |
| WO | WO 2006/032897 | | 3/2006 |

OTHER PUBLICATIONS

Lo, Y.M.D., "Recent developments in fetal nucleic acids in maternal plasma: implications to noninvasive prenatal fetal blood group genotyping," Transfusion clinique et bilogique, 2006, vol. 13, pp. 50-52.

Van Kim et al., "Molecular Cloning and primary structure of the human blood group RhD polypeptide," Proc.Natl.Acad.Sci, 1992, vol. 89, pp. 10925-10929.

Chen et al., Proc. Natl. Acad. Sci. USA 94/20: 10756-10761 (1997).

Chen & Kwok, Nucleic Acids Research 25: 347-353 (1997).

Chow, et al., "Mass Spectrometric detection of a SNP panel as an internal positive control for fetal DNA analysis in maternal plasma," Clin. Chem. 53, 141-142 (2007).

Grompe et al., Proc. Natl. Acad. Sci. USA 86: 5888-5892 (1989).

Grompe, Nature Genetics 5: 111-117 (1993).

Jurinke, C., et al., "MALDI-TOF mass spectrometry: a versatile tool for high-performance DNA analysis." Mol. Biotechnol. 26, 147-164 (2004).

Li, Y., Wenzel, F., Holzgreve, W., Hahn, S., Genotyping fetal paternally inherited SNPs by MALDI-TOF MS using cell-free fetal DNA in maternal plasma: Influence of size fractionation. Electrophoresis 27, 3889-3896 (2006).

Lo et al., Lancet 350, 485-487 (1997).

Lo, Y.M.D. et al. Am. J. Hum. Genet. 62, 768-775 (1998).

Lo, Y.M.D. et al. N. Engl. J. Med. 339, 1734-1738 (1998).

Oeth, P. et al., iPLEX™ Assay: Increased Plexing Efficiency and Flexibility for MassARRAY® System through single base primer extension with mass-modified Terminators. SEQUENOM Application Note (2005).

Orita et al., Proc. Natl. Acad. Sci. U.S.A 86: 27776-2770 (1989).

Sheffield et al., Proc. Natl. Acad. Sci. USA 49: 699-706 (1991).

Van der Schoot, et al., "Real-time PCR of bi-allelic insertion/deletion polymorphisms can serve as a reliable positive control for cell-free fetal DNA in non-invasive prenatal genotyping," Blood v. 102, p. 93a, Abstract #315 (2003).

White et al., Genomics 12: 301-306 (1992).

Avent et al., "Evidence of Genetic Diversity Underlying Rh D⁻, Weak D (D^u), and Partial D Phenotypes as Determined by Multiplex Polymerase Chain Reaction Analysis of the RHD Gene," Blood, vol. 89, No. 7 Apr. 1, 1997: pp. 2568-2577.

Bischoff et al., "Nonvasive Determination of Fetal RhD Status Using Fetal DNA in Maternal Serum and PCR," J. Soc. Gynecol Invest. vol. 6. No. 2, Mar./Apr. 1999.

Claussen et al., "Reliable test for prenatal prediction of fetal RhD type using maternal plasma from RhD negative women," Prenatal Diagnosis 2005:25: 1040-1044.

Costa et al., "Fetal RHD genotyping in maternal serum during the first trimester of pregnancy," British Journal of Hematology 2002, 119, 255-260.

Faas et al., "Detection of fetal RHD-specific sequences in maternal plasma," The Lancet, vol. 352, pp. 1196, Oct. 10, 1998.

Finning et al., "Prediction of fetal D status from maternal plasma:introduction of a new noninvasive fetal RHD genotyping service," Transfusion vol. 42, Aug. 2002 1079-1086.

Gautier et al., "Fetal RhD genotyping by maternal serum analysis: A two-year experience," American Journal of Obstetrics and Gynocology (2005) 192, 666-669.

Harper et al., "Use of maternal plasma for noninvasive determination of fetal RhD status," American Journal of Obstetrics and Gynocology (2004) 191, 1730-1732.

Hoof et al., "PCR-Based RH genotyping with fetal DNA isolated using QlAamp Technology," Customer Application Article, pp. 19-21, Issue 4, 1999.

Le Van Kim et al., "Multiple Rh Messenger RNA Isoforms Are Produced by Alternative Splicing," Blood, vol. 80, No. 4 Aug. 15, 1992: pp. 1074-1078.

Le Van Kim et al., "Molecular cloning and primary structure of the human blood group RhD polypeptide," PNAS vol. 89, pp. 10925-10929 Nov. 1992.

Lo et al., "Prenatal Diagnosis of Fetal RhD Status by Molecular Analysis of Maternal Plasma," The New England Journal of Medicine, vol. 339, No. 24, Dec. 10, 1998, pp. 1734-1738.

Moise, Kenneth J., "Fetal RhD typing with free DNA in maternal plasma," American Journal of Obstetrics and Gynecology (2005) 192, 663-665.

Okuda et al., "The RhD Gene Is Highly Detectable in RhD-negative Japanese Donors," J. Clin. Invest., vol. 100, No. 2, Jul. 1997, 373-379.

Simsek et al., "Rapid Rh D Genotyping by Polymerase Chain Reaction-Based Amplification of DNA," Blood, vol. 85, No. 10 May 15, 1995: pp. 2975-2980.

Singleton et al., "The presence of an RHD pseudogene containing a 37 base pair duplication and a nonsense mutation in Africans with the Rh D-negative blood group phenotype," Blood, Jan. 1, 2000, vol. 95, No. 1, pp. 12-18.

Van der Schoot et al., "Non-invasive antenatal RHD typing Le génotypage RHD prenatal non invasive," Transfusion Clinique et Biologique 13 (2006) 53-57.

Wagner and Flegel, "RHD gene deletion occurred in Rhesus box," Blood, Jun. 15, 2000, vol. 95, No. 12, 3662-3668.

Wagner et al., "RHD positive haplotypes in D negative Europeans," BMC Genetics (2001) 2:10.

* cited by examiner

Exon 4:

Exon 4 and RhDΨ 37bp insertion detection

```
Amplicon 1:        108bp (functional RhD), 145bp (RhD pseudogene)
Forward Primer:    ACGTTGGATGGACTATCAGGGCTTGCCCCG
Reverse Primer:    ACGTTGGATGTGCGAACACGTAGATGTGCA
Extend Primer:     CTGCAGACAGACTACCACATGAAC
Extend Direction:  F
RhD Call:          A
RhDΨ Call:         A & T
RhCE               C

seq1    GTAAGCTCTGAACACCAGTCTCATGGCTTCAAGTCACACCTCCTAAGTGAAGCTCTGAAC
        ||||||||||||||||||||||||||||||||||||||||||||||||||||||||||||
seq2    GTAAGCTCTGAACACCAGTCTCGTGGCTTCAAGTCACACCTCCTAAGTGAAGCTCTGAAC
      28600     28610     28620     28630     28640     28650

                                            TTACTGGGTTTTATTGCAGACAGACTACCACATGAAC

seq1    TTTCTCCAAGGACTATCAGGGCTTGCCCC-GGGCAGAGGATGCCGACACTCACTGCTCTT
        |||||||||||||||||||| |||| ||||||||||||||||||||||||||||||||||
seq2    TTTCTCCAAGGACCATCAGGGCTTTCCCCTGGGCAGAGGATGCCGACACTCACTGCTCTT
      28660     28670     28680     28690     28700     28710

seq1    ACTGGGTTTTATTGCAGACAGACTACCACATGAACATGATGCACATCTACGTGTTCGCAG
        |||||||||||||||||||||||||||||||||| ||| |||| ||||||||||||||||
seq2    ACTGGGTTTTATTGCAGACAGACTACCACATGAACCTGAGGCACTTCTACGTGTTCGCAG
      28720     28730     28740     28750     28760     28770

seq1    CCTATTTTGGGCTGTCTGTGGCCTGGTGCCTGCCAAAGCCTCTACCCGAGGGAACGGAGG
        |||||||||||||| |||||||||||||||||||||||||||||||||||||||||||||
seq2    CCTATTTTGGGCTGACTGTGGCCTGGTGCCTGCCAAAGCCTCTACCCAAGGGAACGGAGG
      28780     28790     28800     28810     28820     28830

seq1    ATAAAGATCAGACAGCAACGATACCCAGTTTGTCTGCCATGCTGGGTAAGGACAAGGTGG
        |||| |||||||||||||||||||||||||||||||||||||||||||||||||||||||
seq2    ATAATGATCAGAGAGCAACGATACCCAGTTTGTCTGCCATGCTGGGTAAGGACAAGGTGG
      28840     28850     28860     28870     28880     28890

seq1    GGTGAGTGGTCTCCTACTTGGGCTGAGCAGAATGGCTCAGAAAAGGCTCTGGCTGAAAAA
        ||||||||||||| ||||||||||||||||||||||||||||||||||||||||||||||
seq2    GGTGAGTGGTCTCATACTTGGGCTGAGCAGAATGGCTCAGAAAAGGCTCTGGCTGAAAAA
      28900     28910     28920     28930     28940     28950
```

FIG. 1A

Exon 4:
Zygosity of RhDΨ

Amplicon 1: 79bp
Forward Primer: *ACGTTGGATG*AGAACGGAGGATAAAGATCAGAC
Reverse Primer: *ACGTTGGATG*AGCCAGCATGGCAGACAAACTG
Extend Primer: GATAAAGATCAGACAGCAAC
Extend Direction: F
RhDΨ Call: A (homozygote); AG (heterozygote)
RhD and RhCE Call: G

```
seq1   GTAAGCTCTGAACACCAGTCTCATGGCTTCAAGTCACACCTCCTAAGTGAAGCTCTGAAC
       ||||||||||||||||||||||||||||||||||||||||||||||||||||||||||||
seq2   GTAAGCTCTGAACACCAGTCTCGTGGCTTCAAGTCACACCTCCTAAGTGAAGCTCTGAAC
      28600     28610     28620     28630     28640     28650

seq1   TTTCTCCAAGGACTATCAGGGCTTGCCCC-GGGCAGAGGATGCCGACACTCACTGCTCTT
       |||||||||||||||||||||||| |||| ||||||||||||||||||||||||||||||
seq2   TTTCTCCAAGGACCATCAGGGCTTTCCCCTGGGCAGAGGATGCCGACACTCACTGCTCTT
      28660     28670     28680     28690     28700     28710

seq1   ACTGGGTTTTATTGCAGACAGACTACCACATGAACATGATGCACATCTACGTGTTCGCAG
       ||||||||||||||||||||||||||||||||||| ||| |||| |||||||||||||||
seq2   ACTGGGTTTTATTGCAGACAGACTACCACATGAACCTGAGGCACTTCTACGTGTTCGCAG
      28720     28730     28740     28750     28760     28770

seq1   CCTATTTTGGGCTGTCTGTGGCCTGGTGCCTGCCAAAGCCTCTACCCGAGGGAACGGAGG
       |||||||||||||| |||||||||||||||||||||||||||||||||||||||||||||
seq2   CCTATTTTGGGCTGACTGTGGCCTGGTGCCTGCCAAAGCCTCTACCCAAGGGAACGGAGG
      28780     28790     28800     28810     28820     28830

                          A(psi)
seq1   ATAAAGATCAGACAGCAACGATACCCAGTTTGTCTGCCATGCTGGGTAAGGACAAGGTGG
       |||| |||||||||||||||||||||||||||||||||||||||||||||||||||||||
seq2   ATAATGATCAGAGAGCAACGATACCCAGTTTGTCTGCCATGCTGGGTAAGGACAAGGTGG
      28840     28850     28860     28870     28880     28890

seq1   GGTGAGTGGTCTCCTACTTGGGCTGAGCAGAATGGCTCAGAAAAGGCTCTGGCTGAAAAA
       ||||||||||||| ||||||||||||||||||||||||||||||||||||||||||||||
seq2   GGTGAGTGGTCTCATACTTGGGCTGAGCAGAATGGCTCAGAAAAGGCTCTGGCTGAAAAA
      28900     28910     28920     28930     28940     28950
```

FIG. 1B

Exon 5:
Amplicon: 71bp
Forward Primer: *ACGTTGGATG*AATCGAAAGGAAGAATGCCG
Reverse Primer: *ACGTTGGATG*CTGAGATGGCTGTCACCACG
Extend Primer: ATGCCGTGTTCAACACCTACTATGCT
Extend Direction: F
RhD Call: G
RhCE Call: C
Extend Primer: GATGGCTGTCACCACGCTGACTGCTA
Extend Direction: R
RhD Call: C
RhCE Call: G

```
        28970     28980     28990     29000     29010     29020
seq1    TTTGGAGCAGGAGTGTGATTCTGGCCAACCACCCTCTCTGGCCCCCAGGCGCCCTCTTCT
        ||||||||||||||||||||||||||||||||||||||||||||||||||||||||||||
seq2    TTTGGAGCAGGAGTGTGATTCTGGCCAACCACCCTCTCTGGCCCCCAGGCGCCCTCTTCT
        29920     29930     29940     29950     29960     29970

        29030     29040     29050     29060     29070     29080
seq1    TGTGGATGTTCTGGCCAAGTTTCAACTCTGCTCTGCTGAGAAGTCCAATCGAAAGGAAGA
        |||||||||||||||||| ||||||||||||||||||||||||||| |||||||||
seq2    TGTGGATGTTCTGGCCAAGTGTCAACTCTGCTCTGCTGAGAAGTCCAATCCAAAGGAAGA
        29980     29990     30000     30010     30020     30030

        29090     29100     29110     29120     29130     29140
seq1    ATGCCGTGTTCAACACCTACTATGCTGTAGCAGTCAGCGTGGTGACAGCCATCTCAGGGT
        ||||| |||||||||||||||||||| |||||||||| ||||||||||||||||||||||
seq2    ATGCCATGTTCAACACCTACTATGCTCTAGCAGTCAGTGTGGTGACAGCCATCTCAGGGT
        30040     30050     30060     30070     30080     30090

        29150     29160     29170     29180     29190     29200
seq1    CATCCTTGGCTCACCCCCAAGGGAAGATCAGCAAGGTGAGCAGGGCGCTGCCCTTGGGCA
        |||||||||||||||||| ||||||||||| ||||||||||||||||||||||||||||
seq2    CATCCTTGGCTCACCCCCAAAGGAAGATCAGCATGGTGAGCAGGGCGCTGCCCTTGGGCA
        30100     30110     30120     30130     30140     30150
```

FIG. 1C

```
Exon 6:
Amplicon:            83bp
Forward Primer:      ACGTTGGATGTGTGGCTGGGCTGATCTGCG
Reverse Primer:      ACGTTGGATGTTCAGCCAAAGCAGAGGAGG
Extend Primer:       AGTTGTCTAGTTTCTTACCGGCAGG
Extend Direction:    R
RhD Call:            A
RhCE Call:           G

         30770     30780     30790     30800     30810     30820
                                                           G(psi)
seq1  GTGTTCTCTCTCTACCTTGCTTCCTTTACCCACACGCTATTTCTTTGCAGACTTATGTGC
      ||||||||||||||||||||||||||||||||||||||||||||||||||||||||||||
seq2  GTGTTCTCTCTCTACCTTGCTTCCTTTACCCACACGCTATTTCTTTGCAGACTTATGTGC
         31720     31730     31740     31750     31760     31770

         30830     30840     30850     30860     30870     30880
seq1  ACAGTGCGGTGTTGGCAGGAGGCGTGGCTGTGGGTACCTCGTGTCACCTGATCCCTTCTC
      ||||||||||||||||||||||||||||||||||||||||||||||||||||||||||||
seq2  ACAGTGCGGTGTTGGCAGGAGGCGTGGCTGTGGGTACCTCGTGTCACCTGATCCCTTCTC
         31780     31790     31800     31810     31820     31830

         30890     30900     30910     30920     30930     30940
seq1  CGTGGCTTGCCATGGTGCTGGGTCTTGTGGCTGGGCTGATCTCCGTCGGGGGAGCCAAGT
      |||||||||||||||||||||||||||||||||||||||||||| |||||||||||||||
seq2  CGTGGCTTGCCATGGTGCTGGGTCTTGTGGCTGGGCTGATCTCCATCGGGGGAGCCAAGT
         31840     31850     31860     31870     31880     31890

         30950     30960     30970     30980     30990     31000
seq1  ACCTGCCGGTAAGAAACTAGACAACTAACCTCCTCTGCTTTGGCTGAAGGCCAGCAGGAC
       ||||||||||||||||||||||||||    ||||||||||||||||||||||||||||
seq2  GCCTGCCGGTAAGAAACTAGACAACTAATGCTCTCTGCTTTGGCTGAAGGCCAGCAGGAC
         31900     31910     31920     31930     31940     31950
```

FIG. 1D

Exon 7:

| | |
|---|---|
| Amplicon: | 95 bp |
| Forward Primer: | *ACGTTGGATG*AGCTCCATCATGGGCTACAAC |
| Reverse Primer: | *ACGTTGGATG*TTGCCGGCTCCGACGGTATC |
| Extend Primer: | TGCTGGGTCTGCTTGGAGAGATCA |
| Extend Direction: | F |
| RhD Call: | T |
| RhCE Call: | C |

```
         34060     34070     34080     34090     34100     34110
seq1    TGCCAATCTGCTTATAATAACACTTGTCCACAGGGGTGTTGTAACCGAGTGCTGGGGATT
        ||||||||||||||||||||||||||||||||| ||||||||||||||||||||||||||
seq2    TGCCAATCTGCTTATAATAACACTTGTCCACAGGTGTGTTGTAACCGAGTGCTGGGGATT
         35000     35010     35020     35030     35040     35050

         34120     34130     34140     34150     34160     34170
seq1    CCCCACAGCTCCATCATGGGCTACAACTTCAGCTTGCTGGGTCTGCTTGGAGAGATCATC
        | ||||||  |||| ||||| || || ||||||||||||||||||||||||||||||| |
seq2    CACCACATCTCCGTCATGCACTCCATCTTCAGCTTGCTGGGTCTGCTTGGAGAGATCACC
         35060     35070     35080     35090     35100     35110

         34180     34190     34200     34210     34220     34230
seq1    TACATTGTGCTGCTGGTGCTTGATACCGTCGGAGCCGGCAATGGCATGTGGGTCACTGGG
        ||||||||||||||||||||||| ||| ||| | |||||||||||||||||||||||||
seq2    TACATTGTGCTGCTGGTGCTTCATACTGTCTGGAACGGCAATGGCATGTGGGTCACTGGG
         35120     35130     35140     35150     35160     35170

         34240     34250     34260     34270     34280     34290
seq1    CTTACCCCCCATCCCCTTAACACTCCCCTCCAACTCAGGAAGAAATGTGTGCAGAGTCCT
        ||||||||||||||||||||||||||||||||||||||||||||||||||||||||||||
seq2    CTTACCCCCCATCCCCTTAACACTCCCCTCCAACTCAGGAAGAAATGTGTGCAGAGTCCT
         35180     35190     35200     35210     35220     35230
```

FIG. 1E

```
RhD Exon 10:
Amplicon:              63bp
RhD Forward:           ACGTTGGATGACGCTCATGACAGCAAAGTC
RhD Reverse Primer:    ACGTTGGATGAACTCCATTTTCTCTGACTC
RhD Extend Primer:     GTCTCCAATGTTCGCGCAGGCAC
RhD Extend Direction:  F
RhD Call:              T

56330     56340     56350     56360     56370     56380
seq1      AGATCAAGCCAAAATCAGTATGTGGGTTCATCTGCAATAAAAATGTTTGTTTTGCTTTTA
          ||||||||||||||||||||||||||||||||||||||||||||||||||||||||||||
seq2      AGATCAAGCCAAAATCAGTATGTGGGTTCATCTGCAATAAAAATGTTTGTTTTGCTTTTA
            58250     58260     58270     58280     58290     58300

          56390     56400     56410     56420     56430     56440
seq1      CAGTTTCCTCATTTGGCTGTTGGATTTTAAGCAAAAGCATCCAAGAAAAACAAGGCCTGT
          ||||||||||||||||||||||||||||||||||||||||||||||||||||||||||||
seq2      CAGTTTCCTCATTTGGCTGTTGGATTTTAAGCAAAAGCATCCAAGAAAAACAAGGCCTGT
            58310     58320     58330     58340     58350     58360

          56450     56460     56470     56480     56490     56500
seq1      TCAAAAACAAGACAACTTCCTCTCACTGTTGCCTGCATTTGTACGTGAGAAACGCTCATG
          ||||||||||||||||||||||||||||||||||||||||||||||||||||||||||||
seq2      TCAAAAACAAGACAACTTCCTCTCACTGTTGCCTGCATTTGTACGTGAGAAACGCTCATG
            58370     58380     58390     58400     58410     58420

          56510     56520     56530     56540     56550     56560
seq1      ACAGCAAAGTCTCCAAT-GTTCGCGCAGGCACTGGAGTCAGAGAAAATGGAGTTGAATCCT
          ||||||||||||||
seq2      ACAGCAAAGTCTCCTTATGTATAATGAAACAAGGTCAGAGACAGATTTGATA
```

FIG. 1F

SRY

TTTCTAAAAGTCAAATGTTAGCCATCCTAGAAGTTGGGCATAAAATACTTGTAAGTATATGCTAATATTC
TGATACTTAATGCCTGTGAAAAATGTGTATAGAATTTTCAATTTTTAAATAGAAGTGAAGAAAAAGCGAT
AATAATTACTATAAATTCAATATGCAGTTATGTATGTATGTGTGTGGTTAAGACAATTAGGTTCTCATTA
AGCTTTGTTTTTTTAAAGATAACATACACATATATTGATAATGATAAACAATTCATATAGCTTTTTGTGT

SRY-3-h-i

CCTCTCGTTTTGTGACATAAAAGGTCAATGAAAAAATTGGCGATTAAGTCAAATTCGCATTTTTCAGGAC
AGCAGTAGAGCAGTCAGGGAGGCAGATCAGCAGGGCAAGTAGTCAACGTTACTGAATTACCATGTTTTGC
TTGAGAATGAATACATTGTCAGGGTACTAGGGGGTAGGCTGGTTGGGCGGGGTTGAGGGGGTGTTGAGGG
CGGAGAAATGCAAGTTTCATTACAAAAGTTAACGTAACAAAGAATCTGGTAGAAGTGAGTTTTGGATAGT
AAAATAAGTTTCGAACTCTGGCACCTTTCAATTTTGTCGCACTCTCCTTGTTTTTGACAATGCAATCATA
TGCTTCTGCTATGTTAAGCGTATTCAACAGCGATGATTACAGTCCAGCTGTGCAAGAGAATATTCCCGCT
CTCCGGAGAAGCTCTTCCTTCCTTTGCACTGAAAGCTGTAACTCTAAGTATCAGTGTGAAACGGGAGAAA
ACAGTAAAGGCAACGTCCAGGATAGAGTGAAGCGACCCATGAACGCATTCATCGTGTGGTCTCGCGATCA

SRY-4-i

GAGGCGCAAGATGGCTCTAGAGAATCCCAGAATGCGAAACTCAGAGATCAGCAAGCAGCTGGGATACCAG
TGGAAAATGCTTACTGAAGCCGAAAAATGGCCATTCTTCCAGGAGGCACAGAAATTACAGGCCATGCACA
GAGAGAAATACCCGAATTATAAGTATCGACCTCGTCGGAAGGCGAAGATGCTGCCGAAGAATTGCAGTTT
GCTTCCCGCAGATCCCGCTTCGGTACTCTGCAGCGAAGTGCAACTGGACAACAGGTTGTACAGGGATGAC
TGTACGAAAGCCACACACTCAAGAATGGAGCACCAGCTAGGCCACTTACCGCCCATCAACGCAGCCAGCT

SRY-5-i

CACCGCAGCAACGGGACCGCTACAGCCACTGGACAAAGCTGTAGGACAATCGGGTAACATTGGCTACAAA
GACCTACCTAGATGCTCCTTTTTACGATAACTTACAGCCCTCACTTTCTTATGTTTAGTTTCAATATTGT
TTTCTTTTCTCTGGCTAATAAAGGCCTTATTCATTTCAGTTTTACTGGTATTTCATTTTAAACTTAATTT
CAAGACAAGTTGTGTCAACACGATTAACATGCAAAGAAATAAGACATCCAGAAGTGAGCCTGCCTATGTT
TGTGGCCGTCAGAGTACTAACTTGATACAAACGGACACTGTGGCTTACTTTAAATGCTCTAATGAGAAAC
ACACTTGAAAATTGTACCAAAAAAAATCACACTTCTATATGCAGCGTGTTAAGCAGTCCTCTCTAGACCG
TGTATTCATTGGTCTTTCAGCTACTTTGTACGTGTCTATAAATTGCAGGTAACTAAGGAATGGATATGTA
AGCAGGATCAAACTTGTTTCTTTCTCTCCCCTTCACGCTGTGGAAAAAACCAGTTTTACCTCCACTTGCA
ATTCAGTTCCTTTACTCCATATAAATCCAAACGGTTGACATTTCCTTTCAACTAGTTATAAAATGCCTCT
GGTAAAACAAAATATTTAATTCCTTGTCATTTTTGTATCTCTATGAAACTTATCATTTTGCCTTTCTTCT
GAAAACTATCTTTTAAAATGGCAATCTACTTGTTTCCATGGCCTATTAACTTTTAAGCCTGTGGAATGAA

Forward PCR Primer
Reverse PCR Primer

FIG. 2

<u>Extend Primer</u>

SRY-3-h-i:

PCR-F: 5'- ACGTTGGATGCGCATTTTTCAGGACAGCAG-3'

PCR-R: 5'- ACGTTGGATGGTAACGTTGACTACTTGCCC-3'

Extend: 5'- CAGGACAGCAGTAGAGCA-3'

Competitor-S:
5'-CGCATTTTTCAGGACAGCAGTAGAGCACTCAGGGAGGCAGATCAGCAGGGCAAGTAGTCAACGTTAC-3'

Competitor-AS:
5'-GTAACGTTGACTACTTGCCCTGCTGATCTGCCTCCCTGAGTGCTCTACTGCTGTCCTGAAAAATGCG-3'

SRY-4-i:

PCR-F: 5'-ACGTTGGATGAGATGGCTCTAGAGAATCCC-3'

PCR-R: 5'-ACGTTGGATGGCATTTTCCACTGGTATCCC-3'

Extend: 5'- TCCCAGAATGCGAAACTC-3'

Competitor-S:
5'-

AGATGGCTCTAGAGAATCCCAGAATGCGAAACTCtGAGATCAGCAAGCAGCTGGGATACCAGTGGAAAATGC-3'

Competitor-AS:
5'-GCATTTTCCACTGGTATCCCAGCTGCTTGCTGATCTCaGAGTTTCGCATTCTGGGATTCTCTAGAGCCATCT-
3'

SRY-5-i:
PCR-F: 5'- ACGTTGGATGAGCAACGGGACCGCTACAG-3'

PCR-R: 5'- ACGTTGGATGAGCATCTAGGTAGGTCTTTG-3'

Extend: 5'-(c)GTTACCCGATTGTCCTAC-3'

Note: non-templated c added for multiplex with Fetal Identifiers. not necessary if run with target gene panels alone.

Competitor-S:
5'-AGCAACGGGACCGCTACAGCCACTGGACAAAGCaGTAGGACAATCGGGTAACATTGGCTACAAAGACCTACCTAGATGCT-3'

Competitor-AS:
5'-AGCATCTAGGTAGGTCTTTGTAGCCAATGTTACCCGATTGTCCTACtGCTTTGTCCAGTGGCTGTAGCGGTCCCGTTGCT-3'

FIG. 2(cont)

CDY

>chrY:26177118+26177212 95bp
>chrY:24603989-24604083 95bp

TCACGAGGTCAGGAGATCGAGACAATCCTGGCTAACATGGTGAAACCCCGTCTCTACTAAAAATACAACA
AATTCGTAGGGCCAGGTGGCAGGTG

| Amplification primer | Amplification primer | Extend Primer sequence |
| --- | --- | --- |
| ACGTTGGATGAGGAGATCGAGACAATCCTG | ACGTTGGATGCTGGCCCTACGAATTTGTTG | cGGCCCTACGAATTTGTTGTATTTTT |

TTTY22

>chrY:6291654+6291734 81bp
>chrY:24603989-24604083 95bp

GCTACTTCTCTACCTTATGGCAGGGACTTGTCGCTAGGCAATGGTGGCATTCATTGTGATGCTAGCCAGA
GCTCACAGCTC

| Amplification primer | Amplification primer | Extend Primer |
| --- | --- | --- |
| ACGTTGGATGTACCTTATGGCAGGGACTTG | ACGTTGGATGCTCTGGCTAGCATCACAATG | GGGACTTGTCGCTAGG |

FIG. 2(cont)

Non-invasive prenatal sex test - AMG_(F/M)-

```
                         10        20        30        40        50        60
 AM-X.SEQ      ACCTCATCCTGGGCACCCTGGTTATATCAACTTCAGCTATGAGGTAATTTTTCTCTTTAC
               X:::::::::::::::::::::::::::::::::::::::::::::::::::::::::::
 AM-Y.SEQ      ACCTCATCCTGGGCACCCTGGTTATATCAACTTCAGCTATGAGGTAATTTTTCTCTTTAC
                         10        20        30        40        50        60

                         70        80        90       100       110       120
 AM-X.SEQ      TAATTTTGACCATTGTTTGCGTTAACAATGCCCTGGGCTCTGTAAAGAATAGTGTGTTGA
               ::::::::: :: ::::::: ::: :: : :::::::::::::::::::::::: :: ::
 AM-Y.SEQ      TAATTTTGATCACTGTTTGCATTAGCAGTCCCCTGGGCTCTGTAAAGAATAGTGGGTGGA
                         70        80        90       100       110       120

                        130                 140       150       160       170
 AM-X.SEQ      TTCTTTATCCCAGAT------GTTTCTCAAGTGGTCCTGATTTTACAGTTCCTACCACCA
               ::::: :::::X ::      ::::::::::::::::  :::::::::::::::::: ::
 AM-Y.SEQ      TTCTTCATCCCAAATAAAGTGGTTTCTCAAGTGGTCCCAATTTTACAGTTCCTACCATCA
                        130       140       150       160       170       180

                    180       190       200       210
 AM-X.SEQ      GCTTCCCAGTTTAAGCTCTGATGGTTGGCCTCAAGCCT
               ::::::::::::::::::::::::::::::::::::::
 AM-Y.SEQ      GCTTCCCAGTTTAAGCTCTGATGGTTGGCCTCAAGCCT
                        190       200       210
```

Primers for non-invasive prenatal sex testing using AMG as target:

PCR primers:
AMG-F: 5'-ACGTTGGATGCCCTGGGCTCTGTAAAGAAT-3'
AMG-R: 5'-ACGTTGGATGAGGCTTGAGGCCAACCATCAG-3'

EXTEND primers:
AMG-E: 5'-TTCTTCATCCCAAATAAAGT-3'

Competitors:
AMG-X-S:
5'-CCCTGGGCTCTGTAAAGAATAGTGTGTTGATTCTTTATCCCAGAaGTTTCTCAAGTGGTCCTGATTTTACAGTTCCTACCACCA GCTTCCCAGTTTAAGCTCTGATGGTTGGCCTCAAGCCT-3'

AMG-X-AS:
5'-AGGCTTGAGGCCAACCATCAGAGCTTAAACTGGGAAGCTGGTGGTAGGAACTGTAAAATCAGGACCACTTGAGAAACtTCTGGGATAAAGA ATCAACACACTATTCTTTACAGAGCCCAGGG-3'

AMG-Y-S:
5'-CCCTGGGCTCTGTAAAGAATAGTGGGTGGATTCTTCATCCCAAATAAAGTcGTTTCTCAAGTGGTCCCAATTTTACAGTTCCTACCATCA GCTTCCCAGTTTAAGCTCTGATGGTTGGCCTCAAGCCT-3'

AMG-Y-AS:
5'-AGGCTTGAGGCCAACCATCAGAGCTTAAACTGGGAAGCTGATGGTAGGAACTGTAAAATTGGGACCACTTGAGAAACgACTTTATTTGGGATGA AGAATCCACCCACTATTCTTTACAGAGCCCAGGG

FIG. 3A

Non-invasive prenatal sex test - AMG-XY-5-i

```
                    10        20        30        40        50        60
AM-X.SEQ      ACCTCATCCTGGGCACCCTGGTTATATCAACTTCAGCTATGAGGTAATTTTTCTCTTTAC
              X:::::::::::::::::::::::::::::::::::::::::::::::::::::::::::
AM-Y.SEQ      ACCTCATCCTGGGCACCCTGGTTATATCAACTTCAGCTATGAGGTAATTTTTCTCTTTAC
                    10        20        30        40        50        60

                    70        80        90       100       110       120
AM-X.SEQ      TAATTTTGACCATTGTTTGCGTTAACAATGCCCTGGGCTCTGTAAAGAATAGTGTGTTGA
              ::::::::: :: ::::::: ::: :: : :::::::::::::::::::::::: :: ::
AM-Y.SEQ      TAATTTTGATCACTGTTTGCATTAGCAGTCCCCTGGGCTCTGTAAAGAATAGTGGGTGGA
                    70        80        90       100       110       120

                   130             140       150       160       170
AM-X.SEQ      TTCTTTATCCCAGAT------GTTTCTCAAGTGGTCCTGATTTTACAGTTCCTACCACCA
              ::::: :::::X ::      ::::::::::::::::  :::::::::::::::::: ::
AM-Y.SEQ      TTCTTCATCCCAAATAAAGTGGTTTCTCAAGTGGTCCCAATTTTACAGTTCCTACCATCA
                   130       140       150       160       170       180

                180       190       200       210
AM-X.SEQ      GCTTCCCAGTTTAAGCTCTGATGGTTGGCCTCAAGCCT
              ::::::::::::::::::::::::::::::::::::::
AM-Y.SEQ      GCTTCCCAGTTTAAGCTCTGATGGTTGGCCTCAAGCCT
                   190       200       210
```

Primers for non-invasive prenatal sex testing using AMG as target:

PCR primers:
AMG-XY-5-i-F: 5'-ACGTTGGATGTATCAACTTCAGCTATGAGG-3'
AMG-XY-5-i-R: 5'-ACGTTGGATGCACTATTCTTTACAGAGC-3'

EXTEND primers:
AMG-XY-5-i-E: 5'-CTTTACAGAGCCCAGGG-3'

Competitors:
AMG-XY-5-i-S:
5'-TATCAACTTCAGCTATGAGGTAATTTTTCTCTTTACTAATTTTGAYCAYTGTTTGCRTTARCARTaCCCTGGGCTCTGTAAAGAATAGTG-3'

AMG-XY-5-i-AS:
5'-CACTATTCTTTACAGAGCCCAGGGtARTGRTAARGCAAACAYTGYTCAAAATTAGTAAAGAGAAAAATTACCTCATAGCTGAAGTTGATA-3'

FIG.3B

Non-invasive prenatal sex test

```
                    10        20        30        40        50        60
AM-X.SEQ    ACCTCATCCTGGGCACCCTGGTTATATCAACTTCAGCTATGAGGTAATTTTTCTCTTTAC
            X:::::::::::::::::::::::::::::::::::::::::::::::::::::::::::
AM-Y.SEQ    ACCTCATCCTGGGCACCCTGGTTATATCAACTTCAGCTATGAGGTAATTTTTCTCTTTAC
                    10        20        30        40        50        60

                    70        80        90       100       110       120
AM-X.SEQ    TAATTTTGACCATTGTTTGCGTTAACAATGCCCTGGGCTCTGTAAAGAATAGTGTGTTGA
            ::::::::: :: ::::::: ::: :: : :::::::::::::::::::::::: :: ::
AM-Y.SEQ    TAATTTTGATCACTGTTTGCATTAGCAGTCCCCTGGGCTCTGTAAAGAATAGTGGGTGGA
                    70        80        90       100       110       120

                   130             140       150       160       170
AM-X.SEQ    TTCTTTATCCCAGAT------GTTTCTCAAGTGGTCCTGATTTTACAGTTCCTACCACCA
            ::::: :::::X ::      ::::::::::::::::  :::::::::::::::::: ::
AM-Y.SEQ    TTCTTCATCCCAAATAAAGTGGTTTCTCAAGTGGTCCCAATTTTACAGTTCCTACCATCA
                   130       140       150       160       170       180

               180       190       200       210
AM-X.SEQ    GCTTCCCAGTTTAAGCTCTGATGGTTGGCCTCAAGCCT
            ::::::::::::::::::::::::::::::::::::::
AM-Y.SEQ    GCTTCCCAGTTTAAGCTCTGATGGTTGGCCTCAAGCCT
                   190       200       210
```

New primers for non-invasive prenatal sex testing using AMG as target:

PCR primers:
AMG-F: 5'-CCCTGGGCTCTGTAAAGAAT-3'
AMG-R: 5'-GAGCTTAAACTGGGAAGCTG-3'

EXTEND primers:
AMG-Y: 5'-TTCTTCATCCCAAATAAAGT-3'
AMG-CON: 5'-CCCTGGGCTCTGTAAAGAATAGT-3'

EXTEND products:
Y chromosome: TTCTTCATCCCAAATAAAGTG
Template positive: CCCTGGGCTCTGTAAAGAATAGTG

RESULTS TABLE

| Sequence Name | Primer Sequence | No. of Nucleotides | Mass |
|---|---|---|---|
| AMG-Y primer | TTCTTCATCCCAAATAAAGT | 20 | 6011 |
| Ychromosome positive | TTCTTCATCCCAAATAAAGTg | 21 | 6340.2 |
| | | | |
| AMG-CON primer | CTGGGCTCTGTAAAGAATAGT | 21 | 6457.2 |
| template positive | CTGGGCTCTGTAAAGAATAGTg | 22 | 6786.4 |
| | | | |
| SRY primer | caggacagcagtagagca | 18 | 5550.6 |
| SRY extension product | caggacagcagtagagcag | 19 | 5879.8 |

FIG.3C

Non-invasive prenatal Albumin test

```
Query 1   GCTCAGTATCTTCAGCAGTGTCCATTTGAAGATCATGTAAAATTAGTGAATGAAGTAACT  60
          ||||||||||||||||||||||||||||||||||||||||||||||||||||||||||||
Sbjct 193 GCTCAGTATCTTCAGCAGTGTCCATTTGAAGATCATGTAAAATTAGTGAATGAAGTAACT
252

Query  61   GAATTTGC  68
            ||||||||
Sbjct  253  GAATTTGC  260
```

ALB Assay:

PCR-F: 5'-ACGTTGGATGCAGTATCTTCAGCAGTGTCC-3'

PCR-R: 5'-ACGTTGGATGGCAAATTCAGTTACTTCATTC-3'

Extend: 5'-CAGTGTCCATTTGAAGATC-3'

Competitor-S:
5'-CAGTATCTTCAGCAGTGTCCATTTGAAGATCtTGTAAAATTAGTGAATGAAGTAACTGAATTTGC-3'

Competitor-AS:
5'-GCAAATTCAGTTACTTCATTCACTAATTTTACAaGATCTTCAAATGGACACTGCTGAAGATACTG-3'

FIG.4

NUCLEIC ACID-BASED TESTS FOR RHD TYPING, GENDER DETERMINATION AND NUCLEIC ACID QUANTIFICATION

RELATED PATENT APPLICATION

This patent application claims the benefit of U.S. provisional patent application No. 60/888,942, filed Feb. 8, 2007, naming Paul Andrew Oeth and Mathias Ehrich as inventors, entitled NUCLEIC ACID-BASED TESTS FOR RHD TYPING, GENDER DETERMINATION AND NUCLEIC ACID QUANTIFICATION, and having attorney docket no. SEQ-6005-PV. The entirety of this provisional patent application is incorporated herein, including all text and drawings.

FIELD

The invention pertains generally to the field of RhD typing, which finds use, for example, in prenatal testing.

BACKGROUND

The Rh system is a highly polymorphic blood group system that plays an important role in haemolytic transfusion reactions, neonatal haemolytic disease and autoimmune haemolytic anemia. There are two different, but highly homologous, genes in the Rh system. One gene (RhD) encodes the D polypeptide, while the other gene (RHCE) encodes the CcEe polypeptide. RhD carries the D antigen—the most potent blood group immunogen. This antigen is absent from a relatively large segment (15-17%) of the population (the Rh-negative phenotype), as a result of RhD gene deletion or other RhD gene alterations (e.g., gene conversion, Pseudogene RhD psi). As used herein the term "psi" refers to the Greek symbol "ψ." RHCE exists in four allelic forms and each allele determines the expression of two antigens in Ce, ce, cE or CE combination (RHCE is the collective name of the four alleles).

Tests for determining RhD type are critical for a wide range of applications. When blood of a rhesus D (RhD) positive donor is given to an RhD negative patient there is a high chance that alloantibody formation occurs. RhD antibodies will lead to rapid destruction of RhD-positive red cells and to transfusion reactions. Furthermore, when a woman with red cell or platelet antibodies becomes pregnant, those antibodies can cross the placenta and can destruct the red cells or the platelets of the unborn child.

In the past, nucleic acid-based RhD typing was performed on fetal nucleic acid procured through invasive means. However, conventional invasive sampling techniques that analyze fetal DNA from amniotic fluid or chorionic villus are costly and may lead to miscarriage and sensitization of the mother. An alternative source of fetal DNA was shown to be maternal plasma and serum (Lo et al., Lancet 350, 485-487 (1997)).

SUMMARY

Recent years have shown a significant increase in the efforts to use circulating cell-free fetal DNA in maternal plasma for non-invasive prenatal diagnostics for example in sex-linked disorders, fetal rhesus D status and beta-thalassaemia (Lo, Y. M. D. et al. *Am. J. Hum. Genet.* 62, 768-775 (1998); and Lo, Y. M. D. et al. *N. Engl. J. Med.* 339, 1734-1738 (1998); both of which are hereby incorporated by reference). In addition to prenatal diagnostics, circulating free fetal nucleic acid may also be used, inter alia, to determine the presence of fetal nucleic acid in a sample, to determine the amount of fetal nucleic acid in a sample, and to determine the sex of a fetus. A non-invasive RhD typing test that is sensitive and accurate enough to determine the RhD genotype of fetal DNA using maternal plasma, but also fast, reliable and affordable enough to be used for a wide range RhD-related applications (e.g., testing donor blood) can serve as an invaluable tool for prenatal diagnostics and blood-related testing.

The invention in part provides nucleic acid-based assays that are particularly useful for non-invasive prenatal testing. The invention in part provides compositions and methods for RhD typing, detecting the presence of fetal nucleic in a sample, determining the relative amount of fetal nucleic acid in a sample, and determining the sex of a fetus, wherein each of the assays may be performed alone or in combination.

The invention in part provides compositions and methods for determining RhD type. In one embodiment, the compositions and methods of the invention may be used to determine the presence or absence of one or more exons in the RhD gene. In a related embodiment, the compositions and methods of the invention may be used to determine the presence or absence of any one of exon 4, exon 5, exon 7 or exon 10 in the RhD gene. In a related embodiment, the compositions and methods of the invention may be used to determine the presence or absence of the RhD pseudogene psi. In a related embodiment, the zygosity of the pseudogene psi is also determined. In another related embodiment, the compositions and methods of the invention may be used to determine the presence or absence of exon 10 of the RhD gene, whereby the presence of exon 10 acts as a positive control for the occurrence of nucleic acid amplification. In another related embodiment, determining RhD type is carried out by annealing an extend primer to a region of the exon, and extending the primer with one or more nucleotides, chain terminating nucleotides or any combination thereof, further wherein the exon region is selected such that primer extension distinguishes between an RhD exon or RhC exon, and whereby the identity of the primer extension product confirms the presence of an RhD exon versus an RhC exon. In some embodiments, the exon region is selected such that primer extension distinguishes between an RhD exon or RhD pseudogene exon, and whereby the identity of the primer extension product confirms the presence of an RhD exon versus an RhD pseudogene exon. In a related embodiment, determining RhD type is carried out by annealing an extend primer to a region of the exon, and extending the primer with one or more nucleotides, chain terminating nucleotides or any combination thereof, further wherein the exon region is selected such that primer extension distinguishes between an RhD gene or RhD psi pseudogene, and whereby the identity of the primer extension product confirms the presence of an RhD gene versus an RhD psi pseudogene.

In certain embodiments, a probe oligonucleotide having the nucleotide sequence of an extend primer described herein, or a nucleotide sequence that is about 90% or more identical (e.g., about 90%, 91%, 92%, 93%, 94%, 95%, 96%, 97%, 98% or 99% or more identical) to the sequence of an extend primer, and further wherein the primer still is specific for a given Rh exon (i.e., specifically hybridizes to a Rh exon) is utilized in place of an extend primer. In such embodiments, the probe oligonucleotide includes a quenchable, detectable label, such as a fluorescent label suitable for use in quantitative polymerase chain reaction detection procedures, for example, known to the person of ordinary skill in the art. Such probe oligonucleotides can be utilized in detection procedures known to the person of ordinary skill in the art, such as quantitative polymerase chain reaction procedures (utilized in a quantitative or non-quantitative format). Quantitative polymerase chain reaction procedures often incorporate the use of a polymerase having exonuclease activity selected by the person of ordinary skill in the art.

The invention in part provides compositions and methods to analyze a nucleic acid sample for the presence or absence of one or more RhD exons, comprising the steps of amplifying the one or more RhD exons with one or more primer pairs provided in Table 3; determining the presence or absence of the amplification products from the amplification reaction, thereby determining the Rh status of an individual. In a related embodiment, the sample is blood from a pregnant female. In some embodiments, one or more of exon 4, exon 5, exon 7 or exon 10 of the RhD gene. In some embodiments, one or more of exon 4, exon 5, exon 7 or exon 10 of the RHCE gene is analyzed. In some embodiments, the exons are analyzed in a multiplexed amplification reaction. In a related embodiment, two or more multiplexed assays are performed in parallel. In some embodiments, the sample is blood, plasma or serum from a pregnant female. In a related embodiment, the sample contains fetal nucleic acid and maternal nucleic acid. In a related embodiment, the RhD status of the fetus and mother are determined in a multiplexed amplification reaction, or a combination of two or more multiplexed reactions. In a related embodiment, the primer pairs in Table 3 comprise a tag sequence to improve multiplexing. In some embodiments, the presence or absence of amplification products is determined by mass spectrometry. In some embodiments, the presence or absence of amplification products is determined by detection of hybridization of the amplification products to a gene chip. In some embodiments, the presence or absence of amplification products is determined by real time-PCR (alternatively called RT-PCR or Q-PCR).

In a related embodiment, the invention in part provides a method of analyzing a sample comprising nucleic acid to determine an Rh genotype, comprising amplifying one or more RhD gene exons or fragments thereof with one or more pairs, or combinations thereof, of amplification primers (i) comprising one of the full length nucleotide sequences hereafter, (ii) comprising one of the underlined nucleotide sequences hereafter, or (iii) comprising one of the underlined nucleotide sequences hereafter and a tag nucleotide sequence:

```
Exon 4 (psi zygosity) Primer Pair 1:
                                  (SEQ ID NO: 1)
ACGTTGGATGCTGCCAAAGCCTCTACACG
and

                                  (SEQ ID NO: 2)
ACGTTGGATGTGGCAGACAAACTGGGTGTC;
or

Exon 4 (psi zygosity) Primer Pair 2:
                                  (SEQ ID NO: 3)
ACGTTGGATGAGAACGGAGGATAAAGATCAGAC
and

                                  (SEQ ID NO: 4)
ACGTTGGATGAGCCAGCATGGCAGACAAACTG,
```

and analyzing the amplification products from the first step to determine the presence or absence of one or more RhD gene exons or fragments thereof, wherein the presence or absence of one or more RhD gene exons or fragments thereof is indicative of an Rh genotype. In some embodiments, each primer of the amplification primer pair may comprise the entire sequence shown or only the underlined sequence, wherein the underlined portion of the primer is a sequence-specific primer sequence and the non-underlined portion is a tag sequence for improved multiplexing. The tag nucleotide sequence may be any tag sequence known in the art, or selected by a person of ordinary skill in the art, that improves multiplexing (e.g., improves mass spectrometry multiplexing). In some embodiments, the invention in part includes primers that are substantially similar to the primers provided herein, for example, a primer having a nucleotide sequence that is about 90% or more identical (e.g., about 90%, 91%, 92%, 93%, 94%, 95%, 96%, 97%, 98% or 99% or more identical), and further wherein the primer still is specific for a given Rh exon (i.e., specifically hybridizes to a Rh exon). For example, one or more bases of a primer sequence may be changed or substituted, for example with an inosine, but the primer still maintains the same specificity and plexing ability.

In a related embodiment, the invention in part provides a method of analyzing a sample comprising nucleic acid to determine an Rh genotype, comprising amplifying one or more RhD gene exons or fragments thereof with one or more pairs, or combinations thereof, of amplification primers (i) comprising one of the full length nucleotide sequences hereafter, (ii) comprising one of the underlined nucleotide sequences hereafter, or (iii) comprising one of the underlined nucleotide sequences hereafter and a tag nucleotide sequence:

```
Exon 4 (psi insertion) Primer Pair 1:
                                  (SEQ ID NO: 5)
ACGTTGGATGGACTATCAGGGCTTGCCCCG
and

                                  (SEQ ID NO: 6)
ACGTTGGATGTGCGAACACGTAGATGTGCA;
```

and analyzing the amplification products from the first step to determine the presence or absence of one or more RhD gene exons or fragments thereof, wherein the presence or absence of one or more RhD gene exons or fragments thereof is indicative of an Rh genotype. In some embodiments, each primer of the amplification primer pair may comprise the entire sequence shown or only the underlined sequence, wherein the underlined portion of the primer is a sequence-specific primer sequence and the non-underlined portion is a tag sequence for improved multiplexing. The tag sequence may be any tag sequence known in the art that improves multiplexing (e.g., multiplex analysis by mass spectrometry). In some embodiments, the invention in part includes primers that are substantially similar to the primers provided herein, for example, a primer having a nucleotide sequence that is about 90% or more identical (e.g., about 90%, 91%, 92%, 93%, 94%, 95%, 96%, 97%, 98% or 99% or more identical), and further wherein the primer still is specific for a given Rh exon (i.e., specifically hybridizes to a Rh exon).

In a related embodiment, the invention in part provides a method of analyzing a sample comprising nucleic acid to determine an Rh genotype, comprising amplifying one or more RhD gene exons or fragments thereof with one or more pairs, or combinations thereof, of amplification primers (i) comprising one of the full length nucleotide sequences hereafter, (ii) comprising one of the underlined nucleotide sequences hereafter, or (iii) comprising one of the underlined nucleotide sequences hereafter and a tag nucleotide sequence:

```
Exon 5 Primer Pair 1:
                                  (SEQ ID NO: 7)
ACGTTGGATGAATCGAAAGGAAGAATGCCG
```

-continued and (SEQ ID NO: 8)
ACGTTGGATGCTGAGATGGCTGTCACCACG;

and analyzing the amplification products from the first step to determine the presence or absence of one or more RhD gene exons or fragments thereof, wherein the presence or absence of one or more RhD gene exons or fragments thereof is indicative of an Rh genotype. In some embodiments, each primer of the amplification primer pair may comprise the entire sequence shown or only the underlined sequence, wherein the underlined portion of the primer is a sequence-specific primer sequence and the non-underlined portion is a tag sequence for improved multiplexing. The tag sequence may be any tag sequence known in the art that improves multiplexing (e.g., multiplex analysis by mass spectrometry). In some embodiments, the invention in part includes primers that are substantially similar to the primers provided herein, for example, a primer having a nucleotide sequence that is about 90% or more identical (e.g., about 90%, 91%, 92%, 93%, 94%, 95%, 96%, 97%, 98% or 99% or more identical), and further wherein the primer still is specific for a given Rh exon (i.e., specifically hybridizes to a Rh exon).

In a related embodiment, the invention in part provides a method of analyzing a sample comprising nucleic acid to determine an Rh genotype, comprising amplifying one or more RhD gene exons or fragments thereof with one or more pairs, or combinations thereof, of amplification primers (i) comprising one of the full length nucleotide sequences hereafter, (ii) comprising one of the underlined nucleotide sequences hereafter, or (iii) comprising one of the underlined nucleotide sequences hereafter and a tag nucleotide sequence:

Exon 7 Primer Pair 1:
(SEQ ID NO: 9)
ACGTTGGATGAGCTCCATCATGGGCTACAA
and (SEQ ID NO: 10)
ACGTTGGATGTTGCCGGCTCCGACGGTATC;
or Exon 7 Primer Pair 2:
(SEQ ID NO: 11)
ACGTTGGATGAGCTCCATCATGGGCTACAAC
and (SEQ ID NO: 10)
ACGTTGGATGTTGCCGGCTCCGACGGTATC, and analyzing the amplification products from the first step to determine the presence or absence of one or more RhD gene exons or fragments thereof, wherein the presence or absence of one or more RhD gene exons or fragments thereof is indicative of an Rh genotype. In some embodiments, each primer of the amplification primer pair may comprise the entire sequence shown or only the underlined sequence, wherein the underlined portion of the primer is a sequence-specific primer sequence and the non-underlined portion is a tag sequence for improved multiplexing. The tag sequence may be any tag sequence known in the art that improves multiplexing (e.g., multiplex analysis by mass spectrometry). In some embodiments, the invention in part includes primers that are substantially similar to the primers provided herein, for example, a primer having a nucleotide sequence that is about 90% or more identical (e.g., about 90%, 91%, 92%, 93%, 94%, 95%, 96%, 97%, 98% or 99% or more identical), and further wherein the primer still is specific for a given Rh exon (i.e., specifically hybridizes to a Rh exon).

In a related embodiment, the invention in part provides a method of analyzing a sample comprising nucleic acid to determine an Rh genotype, comprising amplifying one or more RhD gene exons or fragments thereof with one or more pairs, or combinations thereof, of amplification primers (i) comprising one of the full length nucleotide sequences hereafter, (ii) comprising one of the underlined nucleotide sequences hereafter, or (iii) comprising one of the underlined nucleotide sequences hereafter and a tag nucleotide sequence: Exon 10 Primer Pair 1:

Exon 10 Primer Pair 1:
(SEQ ID NO: 12)
ACGTTGGATGACGCTCATGACAGCAAAGTC
and (SEQ ID NO: 13)
ACGTTGGATGAACTCCATTTTCTCTGACTC;

Exon 10 Primer Pair 2:
(SEQ ID NO: 14)
ACGTTGGATGACTCCATTTTCTCTGACTC
and (SEQ ID NO: 12)
ACGTTGGATGACGCTCATGACAGCAAAGTC, and analyzing the amplification products from the first step to determine the presence or absence of one or more RhD gene exons or fragments thereof, wherein the presence or absence of one or more RhD gene exons or fragments thereof is indicative of an Rh genotype. In some embodiments, each primer of the amplification primer pair may comprise the entire sequence shown or only the underlined sequence, wherein the underlined portion of the primer is a sequence-specific primer sequence and the non-underlined portion is a tag sequence for improved multiplexing. The tag sequence may be any tag sequence known in the art that improves multiplexing (e.g., multiplex analysis by mass spectrometry). In some embodiments, the invention in part includes primers that are substantially similar to the primers provided herein, for example, a primer having a nucleotide sequence that is about 90% or more identical (e.g., about 90%, 91%, 92%, 93%, 94%, 95%, 96%, 97%, 98% or 99% or more identical), and further wherein the primer still is specific for a given Rh exon (i.e., specifically hybridizes to a Rh exon).

Primer Extension

The invention in part provides compositions and methods to analyze a nucleic acid sample for the presence of one or more RhD exons, comprising the steps of amplifying the one or more RhD exons with one or more primer pairs provided in Table 3; annealing one or more extend primers to the amplification products of first step, the extend primers provided in Table 3; performing a primer extension reaction; and analyzing the primer extension products to determine the Rh status of a fetus. The primer extension products may be analyzed using the RhD Test Interpretation Table provided in Table 1. In some embodiments, the presence or absence of primer extension products is determined by mass spectrometry. In some embodiments, the presence or absence of primer extension products is determined by any method known in the art.

In a related embodiment, the invention in part provides a method of analyzing a sample comprising nucleic acid to determine an Rh genotype, comprising the steps of amplifying one or more RhD gene exons or fragments thereof with one or more pairs of amplification primers (i) comprising one of the full length nucleotide sequences hereafter, (ii) comprising one of the underlined nucleotide sequences hereafter, or (iii) comprising one of the underlined nucleotide sequences hereafter and a tag nucleotide sequence:

Exon 4 (psi zygosity) Primer Pair 1:
(SEQ ID NO: 1)
ACGTTGGATGCTGCCAAAGCCTCTACACG
and (SEQ ID NO: 2)
ACGTTGGATGTGGCAGACAAACTGGGTGTC;
or Exon 4 (psi zygosity) Primer Pair 2:
(SEQ ID NO: 3)
ACGTTGGATGAGAACGGAGGATAAAGATCAGAC
and (SEQ ID NO: 4)
ACGTTGGATGAGCCAGCATGGCAGACAAACTG;

annealing one or more extend primers to the amplification products from the first step, the extend primer comprising:

(SEQ ID NO: 15)
gGTCTCCAATGTTCGCGCAGGCAC,
or (SEQ ID NO: 16)
gGATAAAGATCAGACAGCAAC;

extending the primer with one or more nucleotides; and analyzing the primer extension products to determine the presence or absence of one or more RhD gene exons or fragments thereof, wherein the presence or absence of one or more RhD gene exons or fragments thereof is indicative of an Rh genotype. In some embodiments, each primer of the amplification primer pair may comprise the entire sequence shown or only the underlined sequence, wherein the underlined portion of the primer is a sequence-specific primer sequence and the non-underlined portion is a tag sequence for improved multiplexing. The tag sequence may be any tag sequence known in the art that improves multiplexing (e.g., multiplex analysis by mass spectrometry). In some embodiments, the invention in part includes primers that are substantially similar to the amplification and extend primers provided herein, for example, a primer having a nucleotide sequence that is about 90% or more identical (e.g., about 90%, 91%, 92%, 93%, 94%, 95%, 96%, 97%, 98% or 99% or more identical), and further wherein the primer still is specific for a given Rh exon (i.e., specifically hybridizes to a Rh exon). For example, one or more bases of a primer sequence may be changed or substituted, for example with an inosine, but the primer still maintains the same specificity and plexing ability.

In a related embodiment, the invention in part provides a method of analyzing a sample comprising nucleic acid to determine an Rh genotype, comprising the steps of amplifying one or more RhD gene exons or fragments thereof with one or more pairs of amplification primers (i) comprising one of the full length nucleotide sequences hereafter, (ii) comprising one of the underlined nucleotide sequences hereafter, or (iii) comprising one of the underlined nucleotide sequences hereafter and a tag nucleotide sequence:

Exon 4 (psi insertion) Primer Pair 1:
(SEQ ID NO: 5)
ACGTTGGATGGACTATCAGGGCTTGCCCCG
and -continued
(SEQ ID NO: 6)
ACGTTGGATGTGCGAACACGTAGATGTGCA;

annealing one or more extend primers to the amplification products from the first step, the extend primer comprising:

(SEQ ID NO: 17)
GAACGGAGGATAAAGATCAGA,
or (SEQ ID NO: 18)
cTGCAGACAGACTACCACATGAAC;

extending the primer with one or more nucleotides; and analyzing the primer extension products to determine the presence or absence of one or more RhD gene exons or fragments thereof, wherein the presence or absence of one or more RhD gene exons or fragments thereof is indicative of an Rh genotype. In some embodiments, each primer of the amplification primer pair may comprise the entire sequence shown or only the underlined sequence, wherein the underlined portion of the primer is a sequence-specific primer sequence and the non-underlined portion is a tag sequence for improved multiplexing. The tag sequence may be any tag sequence known in the art that improves multiplexing (e.g., multiplex analysis by mass spectrometry). In some embodiments, the invention in part includes primers that are substantially similar to the amplification and extend primers provided herein, for example, a primer having a nucleotide sequence that is about 90% or more identical (e.g., about 90%, 91%, 92%, 93%, 94%, 95%, 96%, 97%, 98% or 99% or more identical), and further wherein the primer still is specific for a given Rh exon (i.e., specifically hybridizes to a Rh exon).

In a related embodiment, the invention in part provides a method of analyzing a sample comprising nucleic acid to determine an Rh genotype, comprising the steps of amplifying one or more RhD gene exons or fragments thereof with one or more pairs of amplification primers (i) comprising one of the full length nucleotide sequences hereafter, (ii) comprising one of the underlined nucleotide sequences hereafter, or (iii) comprising one of the underlined nucleotide sequences hereafter and a tag nucleotide sequence:

Exon 5 Primer Pair 1:
(SEQ ID NO: 7)
ACGTTGGATGAATCGAAAGGAAGAATGCCG
and (SEQ ID NO: 8)
ACGTTGGATGCTGAGATGGCTGTCACCACG;

annealing one or more extend primers to the amplification products from the first step, the extend primer comprising:

(SEQ ID NO: 19)
ATGCCGTGTTCAACACCTACTATGCT, (SEQ ID NO: 20)
GATGGCTGTCACCACGCTGACTGCTA,
or (SEQ ID NO: 21)
tTGTCACCACGCTGACTGCTA;

extending the primer with one or more nucleotides; and analyzing the primer extension products to determine the presence or absence of one or more RhD gene exons or fragments thereof, wherein the presence or absence of one or more RhD gene exons or fragments thereof is indicative of an Rh genotype. In some embodiments, each primer of the amplification primer pair may comprise the entire sequence shown or only the underlined sequence, wherein the underlined portion of the primer is a sequence-specific primer sequence and the non-underlined portion is a tag sequence for improved multiplexing. The tag sequence may be any tag sequence known in the art that improves multiplexing (e.g., multiplex analysis by mass spectrometry). In some embodiments, the invention in part includes primers that are substantially similar to the amplification and extend primers provided herein, for example, a primer having a nucleotide sequence that is about 90% or more identical (e.g., about 90%, 91%, 92%, 93%, 94%, 95%, 96%, 97%, 98% or 99% or more identical), and further wherein the primer still is specific for a given Rh exon (i.e., specifically hybridizes to a Rh exon).

In a related embodiment, the invention in part provides a method of analyzing a sample comprising nucleic acid to determine an Rh genotype, comprising the steps of amplifying one or more RhD gene exons or fragments thereof with one or more pairs of amplification primers (i) comprising one of the full length nucleotide sequences hereafter, (ii) comprising one of the underlined nucleotide sequences hereafter, or (iii) comprising one of the underlined nucleotide sequences hereafter and a tag nucleotide sequence:

```
Exon 7 Primer Pair 1:
                                        (SEQ ID NO: 9)
ACGTTGGATGAGCTCCATCATGGGCTACAA
and

                                        (SEQ ID NO: 10)
ACGTTGGATGTTGCCGGCTCCGACGGTATC;
or

Exon 7 Primer Pair 2:
                                        (SEQ ID NO: 11)
ACGTTGGATGAGCTCCATCATGGGCTACAAC
and

                                        (SEQ ID NO: 12)
ACGTTGGATGTTGCCGGCTCCGACGGTATC;
```

annealing one or more extend primers to the amplification products from the first step, the extend primer comprising:

```
                                        (SEQ ID NO: 22)
CTTGCTGGGTCTGCTTGGAGAGATCA;
```

extending the primer with one or more nucleotides; and analyzing the primer extension products to determine the presence or absence of one or more RhD gene exons or fragments thereof, wherein the presence or absence of one or more RhD gene exons or fragments thereof is indicative of an Rh genotype. In some embodiments, each primer of the amplification primer pair may comprise the entire sequence shown or only the underlined sequence, wherein the underlined portion of the primer is a sequence-specific primer sequence and the non-underlined portion is a tag sequence for improved multiplexing. The tag sequence may be any tag sequence known in the art that improves multiplexing (e.g., multiplex analysis by mass spectrometry). In some embodiments, the invention in part includes primers that are substantially similar to the amplification and extend primers provided herein, for example, a primer having a nucleotide sequence that is about 90% or more identical (e.g., about 90%, 91%, 92%, 93%, 94%, 95%, 96%, 97%, 98% or 99% or more identical), and further wherein the primer still is specific for a given Rh exon (i.e., specifically hybridizes to a Rh exon).

In a related embodiment, the invention in part provides a method of analyzing a sample comprising nucleic acid to determine an Rh genotype, comprising the steps of amplifying one or more RhD gene exons or fragments thereof with one or more pairs of amplification primers (i) comprising one of the full length nucleotide sequences hereafter, (ii) comprising one of the underlined nucleotide sequences hereafter, or (iii) comprising one of the underlined nucleotide sequences hereafter and a tag nucleotide sequence:

```
Exon 10 Primer Pair 1:
                                        (SEQ ID NO: 12)
ACGTTGGATGACGCTCATGACAGCAAAGTC
and

                                        (SEQ ID NO: 13)
ACGTTGGATGAACTCCATTTTCTCTGACTC;

Exon 10 Primer Pair 2:
                                        (SEQ ID NO: 14)
ACGTTGGATGACTCCATTTTCTCTGACTC
and

                                        (SEQ ID NO: 12)
ACGTTGGATGACGCTCATGACAGCAAAGTC;
```

annealing one or more extend primers to the amplification products from the first step, the extend primer comprising:

```
                                        (SEQ ID NO: 15)
gGTCTCCAATGTTCGCGCAGGCAC;
```

extending the primer with one or more nucleotides; and analyzing the primer extension products to determine the presence or absence of one or more RhD gene exons or fragments thereof, wherein the presence or absence of one or more RhD gene exons or fragments thereof is indicative of an Rh genotype. In some embodiments, each primer of the amplification primer pair may comprise the entire sequence shown or only the underlined sequence, wherein the underlined portion of the primer is a sequence-specific primer sequence and the non-underlined portion is a tag sequence for improved multiplexing. The tag sequence may be any tag sequence known in the art that enables multiplexing. In some embodiments, the invention in part includes primers that are substantially similar to the amplification and extend primers provided herein, for example, a primer having a nucleotide sequence that is about 90% or more identical (e.g., about 90%, 91%, 92%, 93%, 94%, 95%, 96%, 97%, 98% or 99% or more identical), and further wherein the primer still is specific for a given Rh exon (i.e., specifically hybridizes to a Rh exon).

In another related embodiment, the invention in part provides a method of analyzing a sample derived from a pregnant female for the presence of one or more of exon 4, exon 5, exon 7 or exon 10 of the RhD gene from fetal nucleic acid, and exon 10 of the RhD gene from maternal nucleic acid, comprising the steps of amplifying the RhD nucleic acid with one or more primer pairs provided in Table 3; determining the presence or absence of the amplification products from the first step, thereby determining the Rh status of a fetus. In an optional embodiment, the presence or absence of exon 10 of the RhD gene may serve as a positive control for the occurrence of nucleic acid amplification or a primer extension reaction. In another related embodiment, a primer extension reaction is performed to determine the presence or absence of one or more of exon 4, exon 5, exon 7 or exon 10 of the RhD gene from fetal nucleic acid, and exon 10 of the RhD gene from maternal nucleic acid, wherein the extend primers are provided in Table 3.

The amplification products and/or primer extension products may be detected by any detection method known in the art, which includes but is not limited to RT-PCR, mass spectrometry and hybridization to a gene chip.

In one embodiment, the primer extension reaction includes the incorporation of a chain terminating nucleotide. In a related embodiment, the chain terminating nucleotide is a dideoxynucleotide, dideoxybromouridine or acyclonucleotide. In some embodiments, the extension reaction comprises incorporation of a deoxynucleotide, a dideoxynucleotide or a combination thereof. In some embodiments, the extension reaction comprises incorporation of a labeled nucleotide. In a related embodiment, the extension reaction comprises using a mixture of labeled and unlabeled nucleotides. In another related embodiment, the labeled nucleotide is labeled with a molecule selected from the group consisting of radioactive molecule, fluorescent molecule, mass label, antibody, antibody fragment, hapten, carbohydrate, biotin, derivative of biotin, phosphorescent moiety, luminescent moiety, electrochemiluminescent moiety, chromatic moiety, and moiety having a detectable electron spin resonance, electrical capacitance, dielectric constant and electrical conductivity. In another related embodiment, the labeled nucleotide is labeled with a fluorescent molecule.

The invention in part provides compositions and methods to detect the presence or absence of a target nucleic acid in a sample. In one embodiment, the compositions and methods of the invention may be used to detect the presence or absence of fetal nucleic acid in a maternal sample. In one embodiment, compositions and methods are provided for analyzing a plurality of polymorphisms in a nucleic acid sample of fetal origin; and analyzing a plurality of polymorphisms in a nucleic acid sample of maternal origin, whereby the presence of at least one polymorphism in the nucleic acid sample of fetal origin, which is not present in the nucleic acid sample of maternal origin, confirms the presence of fetal nucleic acid in the fetal nucleic acid sample. In a related embodiment, the presence of at least one polymorphism in the nucleic acid sample of fetal origin, which is not present in the nucleic acid sample of maternal origin, is a paternally-inherited allele. In some embodiments, the same polymorphisms are analyzed in fetal nucleic acid and maternal nucleic acid. In some embodiments, the polymorphism is heterozygous. The plurality of polymorphisms may include 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000 or more polymorphisms. In a related embodiment, the polymorphism is a single nucleotide polymorphism (SNP), insertion/deletion, short tandem repeats (STRs), RFLPs or any other alternate form of a gene, genomic DNA or non-coding region of DNA that occupies the same position on a chromosome. The polymorphism may be naturally-occurring or synthetic. Synthetic polymorphisms may include alternative forms introduced on a synthetic oligonucleotide that serve as a competitor or control.

In a related embodiment, the invention in part provides compositions and methods of determining the presence or absence of fetal nucleic acid in the sample using the fetal identifiers set forth in Table 3 or 4. In one embodiment, the method of detecting the presence or absence of fetal nucleic acid in a sample comprises obtaining or possessing a nucleic acid sample known to be of maternal origin and suspected of comprising fetal nucleic acid; analyzing the nucleic acid sample to determine the maternal genotype of at one or more nucleotide polymorphisms selected from the group consisting of the polymorphisms set forth in Table 3 or 4; and analyzing the nucleic acid sample to determine the fetal genotype of one or more nucleotide polymorphisms selected from the group consisting of the polymorphisms set forth in Table 3 or 4, wherein a fetal genotype possessing a paternally-inherited allele indicates the presence of fetal nucleic acid. In a related embodiment, the maternal genotypes are determined from DNA that is substantially free of fetal nucleic acid. For example, in the case when the sample is blood, the maternal genotypes may be determined from the portion of the blood that comprises nucleated maternal cells (e.g., white blood cells). In one embodiment, the DNA that is substantially free of fetal nucleic acid is from peripheral blood mononuclear cells. In some embodiments, the amount of fetal DNA is determined by comparing the relative amount of paternally-inherited alleles to maternally-inherited alleles in fetal nucleic acid.

In certain embodiments, the compositions and methods of the invention may be used to detect the presence or absence of the Y-chromosome in a maternal sample, which may be used to determine the sex of a fetus. The presence or absence of the Y-chromosome in a maternal sample may be determined by performing the SRY assay provided herein. The SRY assay is a highly sensitive quantitative internal standard assay that detects trace amounts of the Y-chromosome.

The presence or absence of the Y-chromosome in a maternal sample may also be determined by performing the AMG assay provided herein. The presence or absence of a target nucleic acid may be determined in combination with other assays, such as an RhD assay or sex test assay. The methods may also be used for other applications, including but not limited to, paternity testing, forensics or quality control assays.

The invention in part also provides compositions and methods to determine the relative amount of target nucleic acid in a sample (e.g., fetal nucleic acid in a pregnant female sample). In one embodiment, the compositions and methods of the invention may be used to quantitate the relative amount of the alleles at a heterozygous polymorphic site, wherein said heterozygous polymorphic site has been identified by determining the sequence of alleles at a polymorphic site from template DNA obtained from a maternal sample, wherein said relative amount is expressed as a ratio, wherein said ratio indicates the relative amount of fetal nucleic acid present in the maternal sample. In a related embodiment, the polymorphic sites are provided in Table 3 or 4, 3 or 4. In some embodiments, the polymorphic site is an insertion/deletion, STR or RFLP.

In a related embodiment, the invention in part provides compositions and methods to determine the relative amount of fetal DNA in a sample (e.g., plasma of a pregnant woman carrying a male fetus), which comprises annealing one or more X and Y-specific AMG sequences to the fetal DNA, the primers provided in FIG. 3A-3C; performing a primer extension reaction; and analyzing the primer extension products to determine the ratio of the X and Y-specific extension products. In a related embodiment, the fetal AMG amplicon is first amplified using the amplification primers provided in FIGS. 3A-3C. In another related embodiment, the competitors provided in FIGS. 3A-3C are introduced as an internal standard to determine copy number.

In a related embodiment, the invention in part provides compositions and methods to determine the relative amount of target nucleic acid in a sample (e.g., fetal nucleic acid in plasma of a pregnant woman carrying a male fetus). In one embodiment, one or more Y-specific SRY sequences are annealed to the fetal DNA, the primer comprising GTTACCCGATTGTCCTAC (SEQ ID NO: 23); performing a primer extension reaction; and analyzing the primer extension products to determine the presence and relative amount of Y-specific extension products. In a related embodiment, the fetal SRY amplicon is first amplified using the following amplification primer pair: ACGTTGGATGAGCATCTAGGTAGGTCTTTG (SEQ ID NO: 24) and ACGTTGGATGAGCAACGGGACCGCTACAG (SEQ ID NO: 25).

In some embodiments, the total copy number of nucleic acid molecules for the human serum albumin (ALB) gene is determined. Methods for determining the total copy number of nucleic acid present in a sample comprise detecting albumin-specific extension products and comparing the relative amount of the extension products to competitors introduced to the sample. In a related embodiment, the invention in part provides compositions and methods to determine the relative amount of fetal DNA in a sample (e.g., plasma of a pregnant woman carrying a male fetus), which comprises annealing one or more albumin gene sequences to the fetal DNA, the primers provided in FIG. 4; performing a primer extension reaction; and analyzing the primer extension products to determine the relative amount of ALB extension products. In a related embodiment, the fetal ALB amplicon is first amplified using the amplification primers provided in FIG. 4. The assay is useful to measure how much nucleic acid (e.g., total copy number) is present in a sample or loaded into a particular reaction. The assay may serve as an internal control and a guide to the likelihood of success for a particular PCR reaction. For example, if only 400 copies of ALB are measured then the probability of detecting any fetal DNA may be considered low. In another related embodiment, the competitors provided in FIG. 4 are introduced as an internal standard to determine copy number. In one embodiment, 200, 300, 400, 500, 600, 700, 800 or more competitors are introduced to the assay.

The methods of the present invention may be performed alone or in combination with other tests.

In one embodiment the sample is blood. In certain embodiments, the sample is blood from a pregnant female. In a related embodiment, the blood is obtained from a human pregnant female when the fetus is at a gestational age selected from the group consisting of: 0-4,4-8, 8-12, 12-16, 16-20, 20-24, 24-28, 28-32, 32-36, 36-40, 40-44, 44-48, 48-52, and more than 52 weeks. In another related embodiment, the sample is obtained through non-invasive means. In some embodiments, the nucleic acid is obtained from plasma from said blood. In some embodiments, the nucleic acid is obtained from serum from said blood. In some embodiments, the sample comprises a mixture of maternal DNA and fetal DNA. While the invention is not limited by how the sample is obtained, the methods and compositions of the invention are particularly useful for assaying samples obtained by non-invasive means, which may contain lower amounts of nucleic acid to be assayed. In a related embodiment, the sample is processed to selectively enrich fetal nucleic acid. In another related embodiment, the maternal and fetal Rh genotypes are determined in a multiplexed assay, or a combination of two or more multiplexed reactions. In a further related embodiment, the maternal Rh genotype is determined by analyzing maternal nucleic acid from maternal nucleated cells, for example, peripheral mononuclear blood cells (PMBC).

The invention in part utilizes multiplexed reactions to improve throughput and reduce cost. Thus, provided herein are optimized methods for performing a primer mass extension assay, including an optimized PCR amplification reaction that produces amplified targets for subsequent multiplexed primer mass extension genotyping analysis using mass spectrometry. Also provided herein are optimized methods for performing multiplexed amplification reactions and multiplexed primer mass extension reactions in a single well to further increase the throughput and reduce the cost per genotype for primer mass extension reactions. The nucleic acid target-region amplification and primer mass extension genotyping reactions have been optimized herein to permit moderate to high level multiplexing reactions with greater efficiency and accuracy, while at the same time not adversely affecting the mass spectrometry analysis of mass extension products.

In one embodiment, the amplification primers provided in Table 3 comprises a 5' tag and a gene-specific sequence (underlined). The tag is used to assist in the amplification of the nucleic acids. The primer tags may serve to stabilize the primer during amplification or they may serve as universal primer sites. More specifically, once the RhD gene nucleic acids have been PCR amplified using the primers, primers to the tags are used to further amplify the sequences. In one embodiment, both amplification steps are performed simultaneously. As will be appreciated by those skilled in the art, primers without the 5' tag (primer sequences underlined in the Table) can be used in the method of the invention in order to amplify the RhD gene nucleic acids. Alternatively, the primer sequences can comprise different tag sequences than the tags indicated in the Table. Tag sequences useful for multiplex amplification reactions are well known in the art.

In some embodiments, the amplification primers allow for sequence specific amplification. For example, the PCR primers are designed to discriminate against amplification of the RHCE gene by taking advantage of sequence differences between the RHD and RHCE gene. In some embodiments, the extend primer of the post-PCR primer extension reaction is designed to target a sequence difference between RHD and RHCE gene so that any leakage in the allele-specific amplification would lead to a distinguishable primer extension product that does not interfere with correct interpretation of RHD detection.

In particular embodiments, a sequence tag is attached to a plurality of primary and secondary primer pairs provided in Table 3. The sequence tag can be attached to either one or both of the primary and secondary primers from each pair. Typically, the sequence tag is attached to the primary and secondary primer of each pair. The sequence tags used herein can range from 5 up to 20, from 5 up to 30, from 5 up to 40, or from 5 up to 50nucleotides in length, with a sequence tag of 10-mer length being particularly useful in the methods provided herein. The sequence tag need not be the same sequence for each primer pair in the multiplexed amplification reaction, nor the same sequence for a primary and secondary primer within a particular amplification pair. In a particular embodiment, the sequence tag is the same for each primer in the multiplexed amplification reaction. For example, in certain embodiments, the sequence tag is a 10-mer, such as -ACGTTGGATG- (SEQ ID NO: 26), and is attached to the 5' end of each primary and secondary primer. In particular embodiments of the methods provided herein, only a single primer pair is used to amplify each particular nucleic acid target-region.

BRIEF DESCRIPTION OF THE DRAWINGS

FIG. 1A-1 F provide the location design of the RhD primers. The amplification primers are highlighted and the extend primers are in bold. The Figures also provide the extend primer product associated with each respective assay result. For example, in FIG. 1A, an extension product with an adenine (A) chain terminating nucleotide indicates the presence of exon 4 of the RhD gene, an extension product with an adenine and a thymine (A & T) chain terminating nucleotide indicates the presence of exon 4 of the RhD psi pseudogene, and an extension product with a cytosine (C) chain terminating nucleotide indicates the presence of exon 4 of the RHCE gene. FIG. 1A discloses SEQ ID NOS 5-6, 18 and 174-176, respectively, in order of appearance. FIG. 1B discloses SEQ ID NOS 3-4, 177 and 174-175, respectively, in order of appearance. FIG. 1C discloses SEQ ID NOS 7-8, 19-20and 178-179, respectively, in order of appearance. FIG. 1D discloses SEQ ID NOS 180-184, respectively, in order of appearance. FIG. 1E discloses SEQ ID NOS 11, 10 and 185-187, respectively, in order of appearance. Figure IF discloses SEQ ID NOS 12-13 and 188-190, respectively, in order of appearance.

FIG. 2 provides the location design of the SRY primers in the SRY gene coding sequence (SEQ ID NO: 191). The amplification primers are highlighted and the extend primers are underlined. Where the PCR primers are provided alone, the sequence-specific portion of the primer is underlined, and the multiplex tag is not underlined. In addition, competitor sequences are provided. FIG. 2 discloses SEQ ID NOS 192-201, 25, 24, 202-212, respectively, in order of appearance.

FIG. 3A-3C provide the location design of the AMG primers. The amplification primers are underlined once and the extend primers are underlined twice. In addition, competitor sequences are provided. FIG. 3C includes a Results Table that shows the different masses generated by each of the AMG and SRY assays, which may be used to interpret the results from the assays. FIG. 3A discloses SEQ ID NOS 213-221, respectively, in order of appearance. FIG. 3B discloses SEQ ID NOS 213-214 and 222-226, respectively, in order of appearance. FIG. 3C discloses SEQ ID NOS 213-241, 227-228, 217, 229-231, 217, 230, 232-233, 194 and 234, respectively, in order of appearance.

FIG. 4 provides the location design of the albumin (ALB) primers. The amplification primers are highlighted and the extend primer is underlined twice. Where the PCR primers are provided alone, the sequence-specific portion of the primer is underlined, and the multiplex tag is not underlined. In addition, competitor sequences are provided. FIG. 4 discloses SEQ ID NOS 235-241, respectively, in order of appearance.

DETAILED DESCRIPTION

Figure 5:
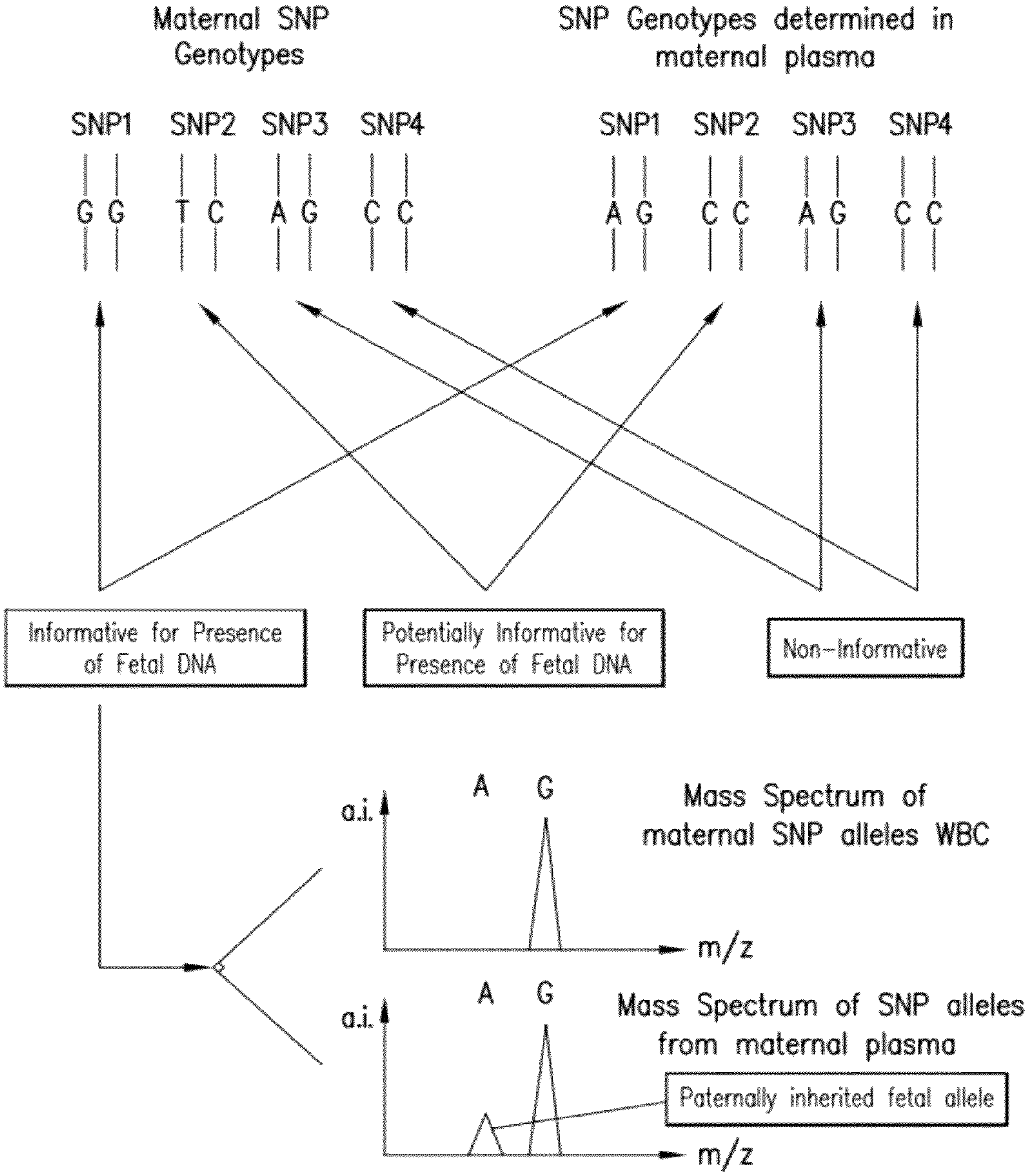
FIG. 5 shows the use of single nucleotide polymorphisms (SNP's) Fetal Identifiers to confirm the presence of fetal DNA by paternally-inherited alleles.

The determination of fetal Rh genotypes from maternal plasma is usually performed by PCR amplification of individual RhD exons. Negative test results, in particular for female fetuses, can require additional tests confirming the presence of sufficient amounts of fetal DNA. The compositions and methods of the invention offer nucleic acid-based tests for determining Rh type and determining the relative amount of target nucleic acid in a sample. The tests are particularly useful for prenatal diagnostics, wherein the presence and relative amount of fetal nucleic acid in a maternal sample can be determined, and further wherein fetal and maternal Rh type can be determined in a highly sensitive, accurate multiplexed reaction. The invention, therefore, provides an alternative method that further comprises high-frequency single nucleotide polymorphisms (SNPs) to determine the amount of fetal nucleic acid present in a sample, which in turn reduces the number of inconclusive tests.

The test primers were designed to ensure that the exon sequence for exons 4, 5, 7 and 10 inclusive of RhD is amplified by the RhD MPX PCR of the invention. The location design of the RhD primers is illustrated in FIGS. 1A-1F.

The assays provided herein offer many advantageous over existing RhD typing methods. Specifically, the multiplexed test reagents address the limited availability of fetal nucleic acid, complexity of genetic changes and high quality testing. The multiplexed RhD/Fetal Identifier assays allow for comprehensive non-invasive Rh genotyping of fetal DNA in only two reactions, while guarding against false-interpretation of negative test results caused by insufficient amounts of fetal DNA. Alternatively, the reactions are performed in a single, multiplexed reaction. The assays have built in quality controls to improve the accuracy of results. The $RhD_\psi$ pseudogene is recognized even in heterozygote state. The SRY assay is highly sensitive and specific for paternal alleles, and the determination of maternal baseline requires only one additional reaction. Finally, the assay can be used for analysis of adult blood donor subjects. This is important in connection with subjects who receive frequent transfusions, for example, those with sickle cell anemia.

In one embodiment, the invention also relates to a method for determining whether a patient in need of a blood transfusion is to be transfused with RhD negative blood from a donor. The invention has important implications for devising a transfusion therapy in humans. For example, it can now be conveniently tested whether the patient actually needs a transfusion with a RhD negative blood or whether such precautions need not be taken.

As used herein, "sample" refers to a composition containing a material to be detected or analyzed. Samples include "biological samples", which refer to any material obtained from a living source, for example, an animal such as a human or other mammal, a plant, a bacterium, a fungus, a protist or a virus or a processed form, such as amplified or isolated material. The sample may be obtained through invasive (e.g., amniocentesis) or non-invasive (e.g., blood draw) means. In a preferred embodiment, the sample is obtained non-invasively. The biological sample can be in any form, including a solid material such as a tissue, cells, a cell pellet, a cell extract, a biopsy, or feces, or a biological fluid such as urine, whole blood, plasma, serum, interstitial fluid, vaginal swab, pap smear, peritoneal fluid, lymph fluid, ascites, sweat, saliva, follicular fluid, breast milk, non-milk breast secretions, cerebral spinal fluid, seminal fluid, lung sputum, amniotic fluid, exudate from a region of infection or inflammation, a mouth wash containing buccal cells, synovial fluid, or any other fluid sample produced by the subject. In addition, the sample can be solid samples of tissues or organs, such as collected tissues, including bone marrow, epithelium, stomach, prostate, kidney, bladder, breast, colon, lung, pancreas, endometrium, neuron, muscle, and other tissues. Samples can include organs, and pathological samples such as a formalin-fixed sample embedded in paraffin. If desired, solid materials can be mixed with a fluid or purified or amplified or otherwise treated. Samples examined using the methods described herein can be treated in one or more purification steps in order to increase the purity of the desired cells or nucleic acid in the sample. Samples also can be examined using the methods described herein without any purification steps to increase the purity or relative concentration of desired cells or nucleic acid. As used herein, the term "blood" encompasses whole blood or any fractions of blood, such as serum and plasma as conventionally defined.

The terms "nucleic acid" and "nucleic acid molecule" may be used interchangeably throughout the disclosure. The terms refer to a deoxyribonucleotide (DNA), ribonucleotide polymer (RNA), RNA/DNA hybrids and polyamide nucleic acids (PNAs) in either single- or double-stranded form, and unless otherwise limited, would encompass known analogs of natural nucleotides that can function in a similar manner as naturally occurring nucleotides.

As used herein, the term "amplifying" or "amplification" refers to means for increasing the amount of a biopolymer, especially nucleic acids. Based on the 5' and 3' primers that are chosen, amplification also serves to restrict and define a target-region or locus of the genome which is subject to analysis. Amplification can be by any means known to those skilled in the art, and in particular embodiments, includes the use of the polymerase chain reaction (PCR). The phrase simultaneous amplification refers to the amplification of 2 or more nucleic acid target-regions at the same time. The simultaneous amplification is typically within the same amplification mixture.

As used herein, the term "multiplexing" refers to the simultaneous amplification or primer mass extension reaction of more than one oligonucleotide or primer (e.g., in a single reaction container); or the simultaneous analysis of more than one oligonucleotide, in a single mass spectrometric or other mass measurement, i.e., a single mass spectrum or other method of reading sequence.

As used herein, the phrase "simultaneous amplification" refers to the multiplexed amplification of 2 or more loci or nucleic acid target-regions in a single reaction mixture. Simultaneous amplification therefore encompasses 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 30 or more, 40 or more, 50 or more, 60 or more, 70 or more, 80 or more, 100 or more, 200 or more, 500 or more, 1000 or more, 2000 or more amplification reactions. The amplification of each particular target-region occurs in parallel at the same time. Although it is contemplated herein that the simultaneous amplifications can occur in separate reaction mixtures, for the methods provided herein the simultaneous amplification reactions typically occur in the same single reaction. Likewise multiplexed primer mass extension refers to the simultaneous extension of 2 or more genotyping primers in a single reaction mixture. Accordingly, multiplexed primer mass extension therefore encompasses [5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 30 or more, 40 or more, 50 or more, 60 or more, 70 or more, 80 or more, 100 or more, 200 or more, 500 or more, 1000 or more, 2000 or more primer mass extension reactions. Multiplexed amplification and primer mass extension reactions also encompass 21, 22, 23, 24, 24, 25, 26, 27, 28, 29, 30, 35, 40, 45, 50, 60, 70, 80, 100, 1000 or more reactions.

As used herein, the phrase "target nucleic acid" refers to one or more nucleic acids, such as genomic DNA, from which one or more regions or loci are to be amplified.

As used herein, the phrase "nucleic acid-target region" refers to the region-specific areas or loci of a target nucleic acid (e.g., UTR, exon or intron) that are amplified for subsequent sequence variation analysis. The amplified nucleic acid-target regions each contain at least one sequence variation or site that is being genotyped.

As used herein, the term "polymorphism" refers to the coexistence of more than one form or allele of a nucleic acid, such as a chromosome, or portion thereof. For example, a portion or locus of a gene at which there are at least two different alleles, i.e., two different nucleotide sequences, is referred to as a polymorphic loci, site or region of a gene. A polymorphic loci can be a single nucleotide (e.g., SNP) or can be several nucleotides in length (e.g., insertions or deletions). Accordingly, polymorphism includes substitutions, insertions, duplications and deletions of nucleotides. A polymorphism can also refer to a particular nucleotide(s) or nucleotide sequence occurring at a particular polymorphic site.

As used herein, the term "genotyping" refers to the process of determining the particular nucleotide or nucleotides (e.g., sequence variation) either present or absent at a particular polymorphic loci or genomic location.

As used herein, "allele", which is used interchangeably herein with "allelic variant" refers to alternative forms of a nucleic acid such as a gene or polymorphic regions thereof. Alleles occupy the same locus or position (referred to herein as a polymorphic region) on homologous chromosomes. When a subject has two identical alleles of a polymorphic region within a gene, the subject is said to be homozygous for the allele. When a subject has two different alleles of a polymorphic region within a gene, the subject is said to be heterozygous for the allele. Alleles of a specific gene can differ from each other at a polymorphic region corresponding to a single nucleotide, or several nucleotides, and can include substitutions, deletions, insertions and duplications of nucleotides. An allele of a gene can also be a form of a gene containing a mutation.

As used herein, the term "non-homologous variant" refers to one or more sequence variations that exist between two or more highly homologous genes (e.g., RhD and RHCE), pseudogenes, transcript variants, repeats or other similar genomic sequences. Non-homologous variants between genes can differ from each other by a single nucleotide, or several nucleotides, and can include substitutions, deletions, insertions and duplications of nucleotides. For example, an RhD pseudogene exists that contains a 37 base pair insertion in exon 4. In the context of the present invention, the 37 base pair insertion of the pseudogene is considered a non-homologous variant. Non-homologous variants usually occupy the same locus or position on highly homologous genes (e.g., in the same, corresponding exon or intron). For example, sequence variations between the highly homologous RhD and RHCE genes are particularly useful for RhD testing.

As used herein, the term "genotype" refers to the identity of the alleles or non-homologous variants present in an individual or sample. The term "genotyping a sample" or "genotyping an individual" refers to determining a specific allele or specific nucleotide(s) in a sample or carried by an individual at particular region(s).

As used herein, the phrase "RhD testing" refers to a DNA-based genotyping method to detect the RhD and/or RHCE genes and their prevalent alleles, non-homologous variants and combinations thereof (e.g., RhD sequence that contains replacements with homologous RHCE sequences). RhD testing may be used to determine an RhD phenotype.

As used herein, the term “Rh phenotype” refers to determining the presence or absence of antigens of the Rh blood group, specifically red cell antigens C, D and E. An individual is either Rh-positive or Rh-negative for a given antigen. For example, “an RhD-negative” individual does not express antigen D, whereas an RhD-positive individual does express antigen D. “Rh incompatibility” occurs when red cells from a Rhesus positive fetus cross the placenta and sensitize a Rhesus negative mother, especially at parturition. The mother’s antibody may then, in a subsequent pregnancy, cause haemolytic disease of the newborn if the fetus is Rhesus positive.

Whether detecting sequence differences, detecting amplification products or primer extension products, any detection method known in the art may be utilized. While many detection methods include a process in which a DNA region carrying the polymorphic site of interest is amplified, ultra sensitive detection methods which do not require amplification may be utilized in the detection method, thereby eliminating the amplification process. Polymorphism detection methods known in the art include, for example, primer extension or microsequencing methods, ligase sequence determination methods (e.g., U.S. Pat. Nos. 5,679,524 and 5,952,174, and WO 01/27326), mismatch sequence determination methods (e.g., U.S. Pat. Nos. 5,851,770; 5,958,692; 6,110,684; and 6,183,958), microarray sequence determination methods, restriction fragment length polymorphism (RFLP) procedures, PCR-based assays (e.g., TAQMAN® PCR System (Applied Biosystems)), nucleotide sequencing methods, hybridization methods, conventional dot blot analyses, single strand conformational polymorphism analysis (SSCP, e.g., U.S. Pat. Nos. 5,891,625 and 6,013,499; Orita et al., *Proc. Natl. Acad. Sci. U.S.A* 86: 27776-2770 (1989)), denaturing gradient gel electrophoresis (DGGE), heteroduplex analysis, mismatch cleavage detection, and techniques described in Sheffield et al., *Proc. Natl. Acad. Sci. USA* 49: 699-706 (1991), White et al., *Genomics* 12: 301-306 (1992), Grompe et al., *Proc. Natl. Acad. Sci. USA* 86: 5855-5892 (1989), and Grompe, *Nature Genetics* 5: 111-117 (1993), detection by mass spectrometry (e.g., US 20050079521, which is hereby incorporated by reference), real time-PCR (e.g., U.S. Pat. No. 5,210,015, U.S. Pat. No. 5,487,972, both of which are hereby incorporated by reference), or hybridization with a suitable nucleic acid primer specific for the sequence to be detected. Suitable nucleic acid primers can be provided in a format such as a gene chip.

Primer extension polymorphism detection methods, also referred to herein as “microsequencing” methods, typically are carried out by hybridizing a complementary oligonucleotide to a nucleic acid carrying the polymorphic site. In these methods, the oligonucleotide typically hybridizes adjacent to the polymorphic site. As used herein, the term “adjacent” refers to the 3' end of the extension oligonucleotide being sometimes 1 nucleotide from the 5' end of the polymorphic site, often 2 or 3, and at times 4, 5, 6, 7, 8, 9, or 10 nucleotides from the 5' end of the polymorphic site, in the nucleic acid when the extension oligonucleotide is hybridized to the nucleic acid. The extension oligonucleotide then is extended by one or more nucleotides, often 1, 2, or 3 nucleotides, and the number and/or type of nucleotides that are added to the extension oligonucleotide determine which polymorphic variant or variants are present. Oligonucleotide extension methods are disclosed, for example, in U.S. Pat. Nos. 4,656,127; 4,851,331; 5,679,524; 5,834,189; 5,876,934; 5,908,755; 5,912,118; 5,976,802; 5,981,186; 6,004,744; 6,013,431; 6,017,702; 6,046,005; 6,087,095; 6,210,891; and WO 01/20039. The extension products can be detected in any manner, such as by fluorescence methods (see, e.g., Chen & Kwok, *Nucleic Acids Research* 25: 347-353 (1997) and Chen et al., *Proc. Natl. Acad. Sci. USA* 94/20:10756-10761 (1997)) and by mass spectrometric methods (e.g., MALDI-TOF mass spectrometry or electrospray mass spectrometry). Oligonucleotide extension methods using mass spectrometry are described, for example, in U.S. Pat. Nos. 5,547,835; 5,605,798; 5,691,141; 5,849,542; 5,869,242; 5,928,906; 6,043,031; 6,194,144; and 6,258,538.

Microsequencing detection methods often incorporate an amplification process that proceeds the extension step. The amplification process typically amplifies a region from a nucleic acid sample that comprises the polymorphic site. Amplification can be carried out by utilizing a pair of oligonucleotide primers in a polymerase chain reaction (PCR), in which one oligonucleotide primer typically is complementary to a region 3' of the polymorphism and the other typically is complementary to a region 5' of the polymorphism. A PCR primer pair may be used in methods disclosed in U.S. Pat. Nos. 4,683,195; 4,683,202, 4,965,188; 5,656,493; 5,998,143; 6,140,054; WO 01/27327; and WO 01/27329 for example. PCR primer pairs may also be used in any commercially available machines that perform PCR, such as any of the GENEAMP® Systems available from Applied Biosystems.

A microarray can be utilized for determining whether a polymorphic variant is present or absent in a nucleic acid sample. A microarray may include any oligonucleotides described herein, and methods for making and using oligonucleotide microarrays suitable for prognostic use are disclosed in U.S. Pat. Nos. 5,492,806; 5,525,464; 5,589,330; 5,695,940; 5,849,483; 6,018,041; 6,045,996; 6,136,541; 6,142,681; 6,156,501; 6,197,506; 6,223,127; 6,225,625; 6,229,911; 6,239,273; WO 00/52625; WO 01/25485; and WO 01/29259. The microarray typically comprises a solid support and the oligonucleotides may be linked to this solid support by covalent bonds or by non-covalent interactions. The oligonucleotides may also be linked to the solid support directly or by a spacer molecule. A microarray may comprise one or more oligonucleotides complementary to a polymorphic site within a nucleotide sequence in Tables 6, 7 or 8.

Fetal Identifiers

Cell-free fetal DNA constitutes only a minor fraction of the total DNA found in maternal plasma. The amount of fetal DNA in maternal plasma is dependent on the gestational age and is estimated at 3-6%.

Because the analysis is relying on the detection of a paternally-inherited disease-causing sequence, it is vital to be able to ascertain that the absence of the disease-causing sequence is a true diagnostic result and not caused by insufficient amount of circulating fetal DNA or even loss of the fetal DNA during sample processing.

The use of polymorphisms provide a means to confirm the presence of fetal DNA and therefore complete the analysis of negative, and otherwise inconclusive, test result in non-invasive prenatal diagnostics. The use of single nucleotide polymorphisms (SNPs), the most abundant type of polymorphism in the human genome, or insertion/deletion (Ins/Del) polymorphisms may serve as fetal identifiers to determine the presence of fetal DNA in a processed sample (Li, Y., Wenzel, F., Holzgreve, W., Hahn, S., Genotyping fetal paternally inherited SNPs by MALDI-TOF MS using cell-free fetal DNA in maternal plasma: Influence of size fractionation. Electrophoresis 27, 3889-3896 (2006); Van der Schoot, C. E., Rijnders, R. J., Bossers, B., de Haas, M., Christiaens, G. C., Dee, R. Real-time PCR of bi-allelic insertion/deletion polymorphisms can serve as a reliable positive control for cell-free fetal DNA in non-invasive prenatal genotyping [abstract] Blood 102, 93a (2003); and Chow, K. C., Chiu, R. W., Tsui, N. B., Ding, C., Lau, T. K., Leung, T. N., Lo, Y. M., Mass Spectrometric detection of a SNP panel as an internal positive control for fetal DNA analysis in maternal plasma. Clin. Chem. 53, 141-142 (2007), all of which are hereby incorporated by reference).

A SNP is considered informative for the determination of the presence of fetal DNA, if the mother is homozygous and the fetus inherited the opposite allele from the father, rendering the genotype of the fetus heterozygous.

To ensure a high probability that the presence of fetal DNA can be confirmed by the presence of the paternally-inherited allele in at least 1 SNP, a sufficient number of SNPs or Ins/Dels with a high population frequency (>0.4 for the minor frequent allele) has to be analyzed. A scheme exemplifying the concept of using SNPs to confirm the presence of fetal DNA in maternal plasma is depicted in FIG. 5.

Analysis of multiple polymorphisms in DNA extracted from maternal plasma creates a two-fold challenge: firstly, the paternally-inherited allele needs to be detected in the background of the maternal DNA; secondly, the high number of polymorphisms require significant sample material and a significant number of reactions before a conclusive test result is achieved.

Thus the invention in part provides a multiplexed panel of SNPs to establish a universal assay panel for non-invasive prenatal diagnostics.

Kits

Furthermore, the invention relates to a kit comprising the compositions of the invention. Parts of the kit can be packaged individually in vials or in combination in containers or multicontainer units. The kit of the present invention may be advantageously used for carrying out the method of the invention and could be, inter alia, employed in a variety of applications referred to above. The manufacture of the kits follows preferably standard procedures which are known to people skilled in the art.

EXAMPLES

The following examples illustrate but do not limit the invention.

Example 1

RhD Test

Analysis of RhD exons and SNPs was enabled by multiplex PCR followed by multiplexed allele-specific primer extension and analysis by MALDI-TOF MS. Initial evaluation of the assays was performed using genomic DNA. Multiplexes were also evaluated from artificial mixtures to establish sensitivity and precision of the semi-quantitative readout of SNP alleles. Final performance was established using cell-free fetal DNA from maternal plasma.

Extraction of cell-free fetal DNA was performed using a modified Qiagen MinElute protocol.

Two multiplex reactions were developed that cumulatively integrated the detection of RhD exons 4, 5, 7, 10 and the detection of the RhD psi pseudogene conversion with 16 high-frequent SNPs. The use of 16 SNPs statistically provides up to 4 assays, which can confirm the presence of fetal DNA through detection of the paternally-inherited fetal allele. Performance of the multiplexed assays in artificial mixtures and in cell-free fetal DNA extracted from maternal plasma was demonstrated.

The method comprises the following 8 steps:

1. Isolate plasma and peripheral blood mononuclear cells (PBMC) from whole blood.
2. Purify cell-free DNA from the plasma (designated fetal DNA).
3. Purify DNA from PBMC (designated maternal DNA).
4. Prepare fetal and maternal DNA working dilutions (0.15 ng/μl).
5. Amplify the fetal and maternal DNA.
6. Process the Iplex™ Gold extend reactions on the amplified fetal and maternal DNA.
7. Dispense the MassExtend reaction products to a SpectroCHIP® array.
8. Analyze samples on the MassARRAY Analyzer Compact
9. Interpret the results using with the aid of Table 1

TABLE 1

RhD Test Interpretation

| | RhD/ RhD psi Exon 4 | RhD/ RhD psi Exon 4 | RhD Exon 5 | RhD Exon 7 | RhD Exon 10 | Test Interpretation |
|---|---|---|---|---|---|---|
| Gene deletion | **C** | **G** | **C** | **C** | — | RhD− |
| Gene conversion RhD-CE-D; exons 1 and 10 of RhD gene present | **C** | **G** | **C** | **C** | T | RhD− |
| Gene conversion RhD-CE-D; exons 1-3 and 9-10 of RhD gene present | **C** | **G** | **C** | **C** | T | RhD− |
| Pseudogene RhDy homozygous | AT | A | G | T | T | RhD− |
| Pseudogene RhDy heterzygous | AT | AG | G | T | T | RhD+ |
| Apparently intact RhD gene; possibly bearing single point mutations | A | G | G | T | T | RhD+ |

RhCE alleles denoted in bold and underlined represent leakage from allele-specific priming.

Any negative result is a true negative.

Any positive result is a true positive.

Inconclusive Results will Result in Further Testing and/or Therapy.

Step 5 and 6 are further described herein. Following genomic amplification, the assay interrogates amplified regions through the use of specific primers that are designed to hybridize directly adjacent to the site of interest. These DNA oligonucleotides are referred to as iPLEX MassEXTEND primers. In the extension reaction, the iPLEX primers are hybridized to the complementary DNA templates and extended with a DNA polymerase. Special termination mixtures that contain different combinations of deoxy- and dideoxynucleotide triphosphates along with enzyme and buffer, direct limited extension of the iPLEX primers. Primer extension occurs until a complementary dideoxynucleotide is incorporated.

The extension reaction generates primer products of varying length, each with a unique molecular weight. As a result, the primer extension products can be simultaneously separated and detected using Matrix Assisted Laser Desorption/Ionization, Time-Of-Flight(MALDI-TOF) mass spectrometry on the MassARRAY® Analyzer Compact. Following this separation and detection, SEQUENOM's proprietary software automatically analyzes the data and presents the assay results in the BioReporter RhD report.

A more specific protocol is provided in the Tables below. These conditions are not intended to limit the scope of the invention.

TABLE A

PCR Master Mix Preparation (MMX)

| MMX | Reagent | Final Conc. per 50 μl rxn | Volume per each 50 μl (ul) | Volume per 100 rxn (ul) |
|---|---|---|---|---|
| MMX1 | Water | N/A | 7.55 | 755 |
| | 10 × PCR Buffer (contains 15 mM MgCl2, Tris-Cl, KCl, (NH4)2SO4, pH 8.7 (Qiagen) | 1.25x | 6.25 | 625 |
| | 25 mM $MgCl_2$ (Qiagen) | 1.625 mM | 3.25 | 325 |
| | PCR Nucleotide Mix (10 mM each dATP, dCTP, dGTP, dUTP) (Roche) | 800 μM (200 uM each | 1 | 100 |
| | 2 U/μl Uracil-DNA-Glycosylase (UDG)(NEB) | 2.5 U/rxn | 1.25 | 125 |
| | 5 U/μl HotStar Taq (Qiagen) | 3.5 U/rxn | 0.7 | 70 |
| | Sub Total for MMX1 | | 20 | 2000 |
| MMX2 | 0.5-1.5 uM RhD primers Mix (Operon/IDT) | 0.1-0.5 uM each | 10 | 1000 |
| MMX | Total for MMX | | 30 | 3000 |
| Sample | DNA ng/ul | | 20 | |
| | PCR Reaction Total | | 50 | |

1.2.1 Combine 20 ul of MMX1 and 10 ul of MMX2 to make 30 ul of each PCR MMX.

1.2.2 Add 20 ul of sample (plasma DNA) to MMX 1.2.3 Mix well, seal plate, spin briefly and cycle according to following parameters in table 3.

TABLE B

PCR 30-11 Cycling Conditions (two steps cycling)

| Temp. | Time | Cycles | Notes |
|---|---|---|---|
| 30 C. | 10 min | 1 | UDG Incubation |
| 94 C. | 15 min | 1 | Initial Denaturation |
| 94 C. | 20 sec | 30 cycles | Target Amplification |
| 56 C. | 30 sec | | |
| 72 C. | 1 min | | |
| 94 C. | 20 sec | 11 cycles | Product Amplification |
| 62 C. | 30 sec | | |
| 72 C. | 1 min | | |
| 72 C. | 3 min | 1 | Final Extension |
| 4 C. | Forever | 1 | Hold |

1.2.4 10 uL PCR Aliquots

Prepare two iPLEX EXTEND reaction plates by plating 10 uL PCR samples from each well of the PCR plate into two new 96-well plates designated for SAP and EXTEND reactions using the liquid handler 1.3 SAP Reaction 1.3.1 Prepare the SAP mixes according to Table 4 below. Dispense 6 μl SAP mix to the corresponding wells of one V-bottom Sarstedt 96-well plate. Transfer 4 μl SAP from the 96-well stock plate to each of the 96-well PCR plates, using a Liquid Handler.

TABLE C

SAP Cocktail preparation

| Reagent | Final C | Volume [uL] (60% overhang) n = 1 | 160 | Lot# |
|---|---|---|---|---|
| Nanopure Water, Autoclaved | n/a | 2.95 | 472 | |
| SAP Buffer, 10x | 0.85x | 0.34 | 54.4 | |
| SAP (1.7 U/ul = transparent label) | 1.2 U/rxn | 0.71 | 113.6 | |
| Total volume [uL] | n/a | 4 | 640 | n/a |

1.3.2 When preparation is finished, seal the plate, vortex, centrifuge briefly and cycle each plate according to the following parameters in the table below.

TABLE D

SAP Thermal Cycling Conditions

| Temperature | Incubation Time | Plate ID |
|---|---|---|
| 37° C. | 40 minutes | Program ID: SAP-40-5 |
| 80° C. | 5 minutes | |
| 4° C. | store | |

1.4 iPLEX Extension

TABLE E iPLEX EXTEND Cocktail Mix Preparation

| Extend Reagent | Volume = 1-Rxn | Volume [uL] (60% overhang) 160 |
|---|---|---|
| Water (HPLC grade) | 1.238 | 198.08 |
| iPLEX detergent free buffer (10x) | 0.4 | 64 |
| iPLEX Termination Mix | 0.4 | 64 |
| Extend Primer Mix | 1.88 | 300.8 |
| Thermosequenase (32 U/uL) | 0.082 | 13.12 |
| Total Volume | 4 | 640 |

1.4.1 Add 6 ul cocktail to each well of one V-bottom Sarstedt 96 plate. Transfer 4 μl iPLEX-EXTEND cocktail from the V-bottom Sarstedt 96 plate to each well of the 96-SAP/PCR plates, using a Matrix MassARRAY Liquid Handler into well positions according to plate lay out.

1.4.2 Seal the plates, vortex, centrifuge briefly and cycle according to the parameters listed below in Table 10.

TABLE F hME-100

| Temperature | Incubation Time | Cycles | Notes |
|---|---|---|---|
| 94° C. | 2 minutes | 1 | Plate ID: 1) 06-28-2006_HLBK_ST_DOL |
| 94° C. | 5 seconds | 99 cycles | Program ID: hME-100 |
| 52° C. | 5 seconds | | Cycler ID: BLK0116, BSE 0046 |
| 72° C. | 5 seconds | | Cycler Bonnet ID (iM applicable): |
| 4° C. | forever | 1 | |

Example 2

Fetal Identifiers, Sex Test and Copy Number Determination

Selection of SNPs

Analysis of paternally-inherited alleles in clinical samples and correlation with Y-chromosome frequency in male fetuses was performed with a total of 16 SNPs; SNP assays for analysis of clinical samples were multiplexed as 8-plexes; all SNPs had a minor allele frequency (maf) of ~0.4 in all ethnic groups and were unlinked.

For performance evaluation of a universal Fetal Identifier panel that can be multiplexed with disease-specific markers, a new panel of 87 A/T SNPs with a pan-ethnic maf >0.4 was selected and multiplexed into 16-plexes.

Method of SNP Analysis

Figure 6:
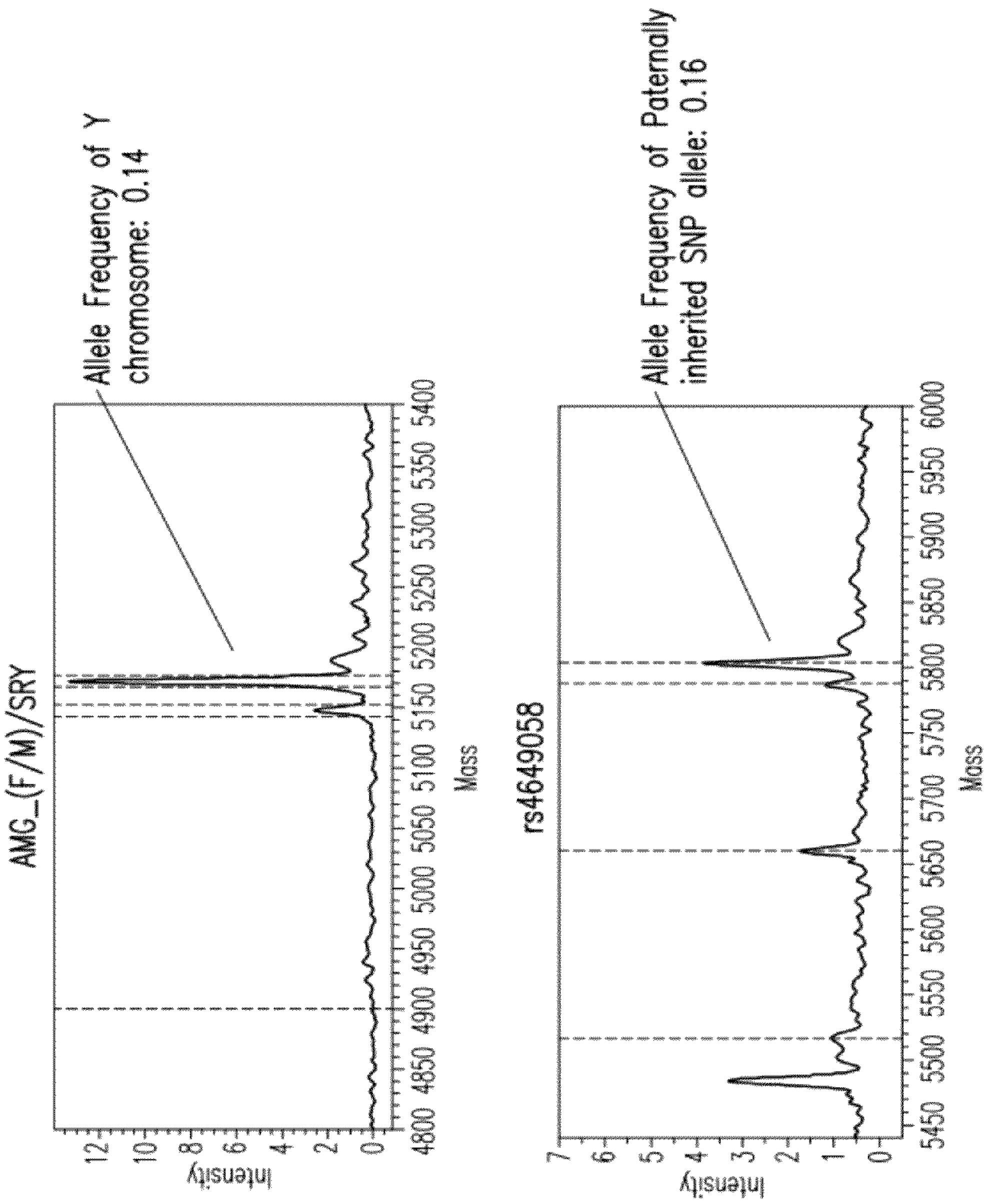
FIG. 6 shows representative mass spectra demonstrating the correlation between fetal DNA amounts estimated from AMG XY and from Fetal Identifier assays. The results were generated using the AMG primers provided in FIG. 3.

Analysis of SNPs in maternal buffy coat and maternal plasma was performed using the iPLEX™ assay and MassARRAY® technology (Jurinke, C., Oeth, P., van den Boom, D., MALDI-TOF mass spectrometry: a versatile tool for high-performance DNA analysis. *Mol. Biotechnol.* 26, 147-164 (2004); and Oeth, P. et al., iPLEX™ Assay: Increased Plexing Efficiency and Flexibility for MassARRAY® System through single base primer extension with mass-modified Terminators. SEQUENOM Application Note (2005), both of which are hereby incorporated by reference). In brief, the target region surrounding the SNP is first amplified by PCR. Subsequently an oligonucleotide primer is annealed to the PCR product and is extended allele-specifically by a single nucleotide using a mixture of 4 terminator nucleotides and a DNA polymerase. The extension products are transferred to a miniaturized chip array and are analyzed by MALDI-TOF Mass Spectrometry. Determination of the molecular mass of extension products allows unambiguous identification of the SNP allele present in the sample. The peak area ratio of mass signals allows the estimation of the relative abundance of the alleles in a given sample. FIG. 6 provides an overview of the assay used for SNP analysis.

Clinical Samples

The total sample set consisted of 35 paired blood/plasma samples from pregnant Caucasian woman (nine 1st trimester; twelve 2nd trimester; fourteen 3rd trimester).

The subset of samples used for correlation of Y-chromosome frequency and paternally-inherited alleles in maternal plasma consisted of 19 samples of pregnant Caucasian woman carrying a male fetus.

DNA Extraction

DNA extraction was performed from 1 ml of maternal plasma using the Qiagen MinElute kit for fetal genotyping.

DNA extraction from frozen blood (minus plasma) was performed from 4 ml using Qiagen's PureGene kit for maternal genotyping.

Results

An assay targeting sequence differences in the Amelogenin region on the X and Y chromosome was used to assess the relative amount of fetal DNA extracted from plasma of pregnant woman carrying a male fetus. Details of the AMG assay are depicted in FIGS. 3A-3C. X and Y-specific sequences can be discriminated by sequence specific iPLEX extension products and their respective mass signals. The peak area ratio of the extension products allows estimation of the relative amount of fetal DNA, because the Y-specific sequences represent 50% of the total fetal DNA contribution.

Sixteen of nineteen (84%) plasma samples with a male fetus showed a Y-chromosome frequency of higher than 5%, indicating presence of at least 10% fetal DNA in the extracted DNA.

Figure 7:
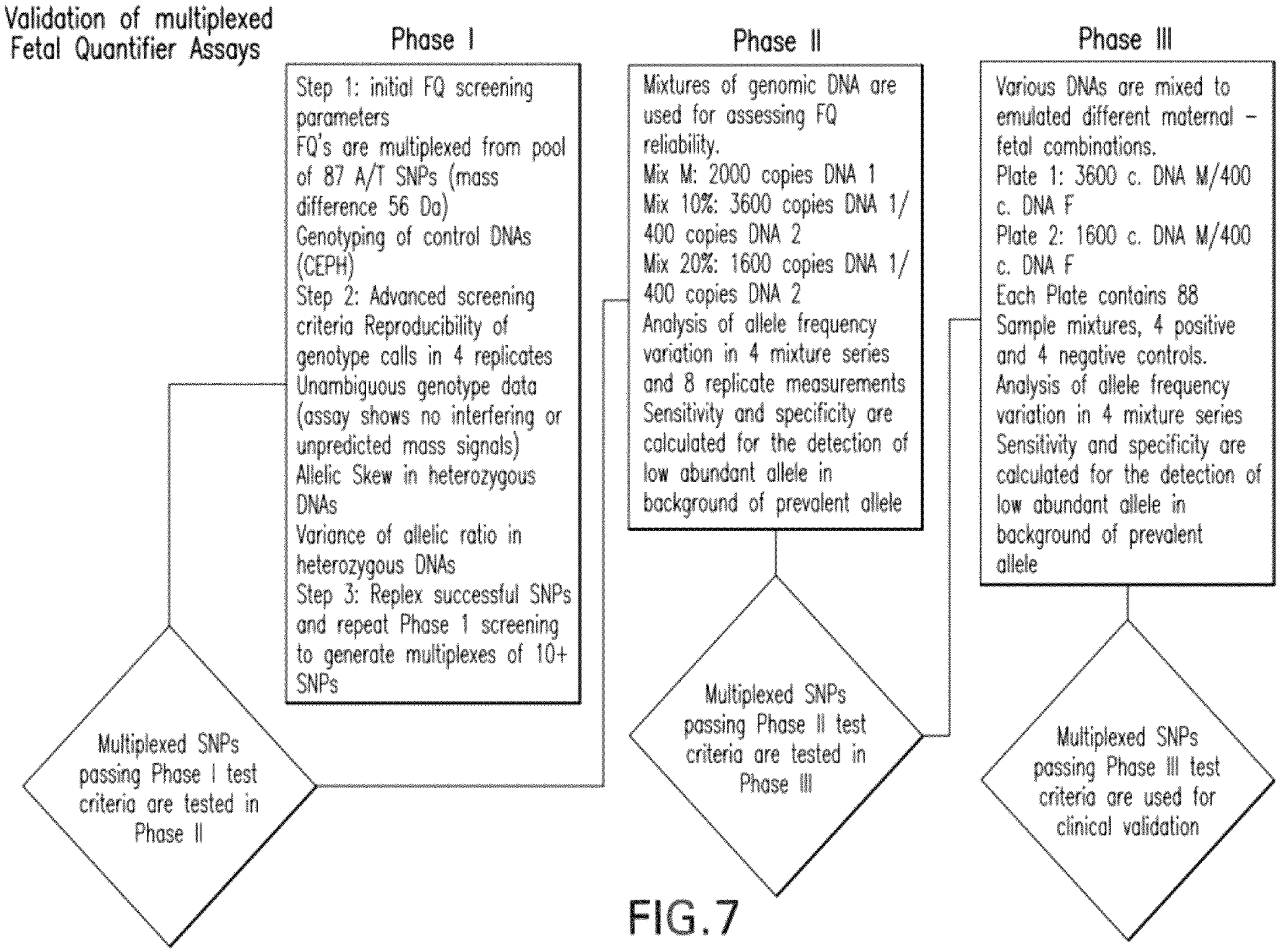
FIG. 7 depicts the validation scheme, performance criteria and model system used to qualify multiplex SNP assays for their utility in identifying the presence for fetal DNA.
Figure 8:
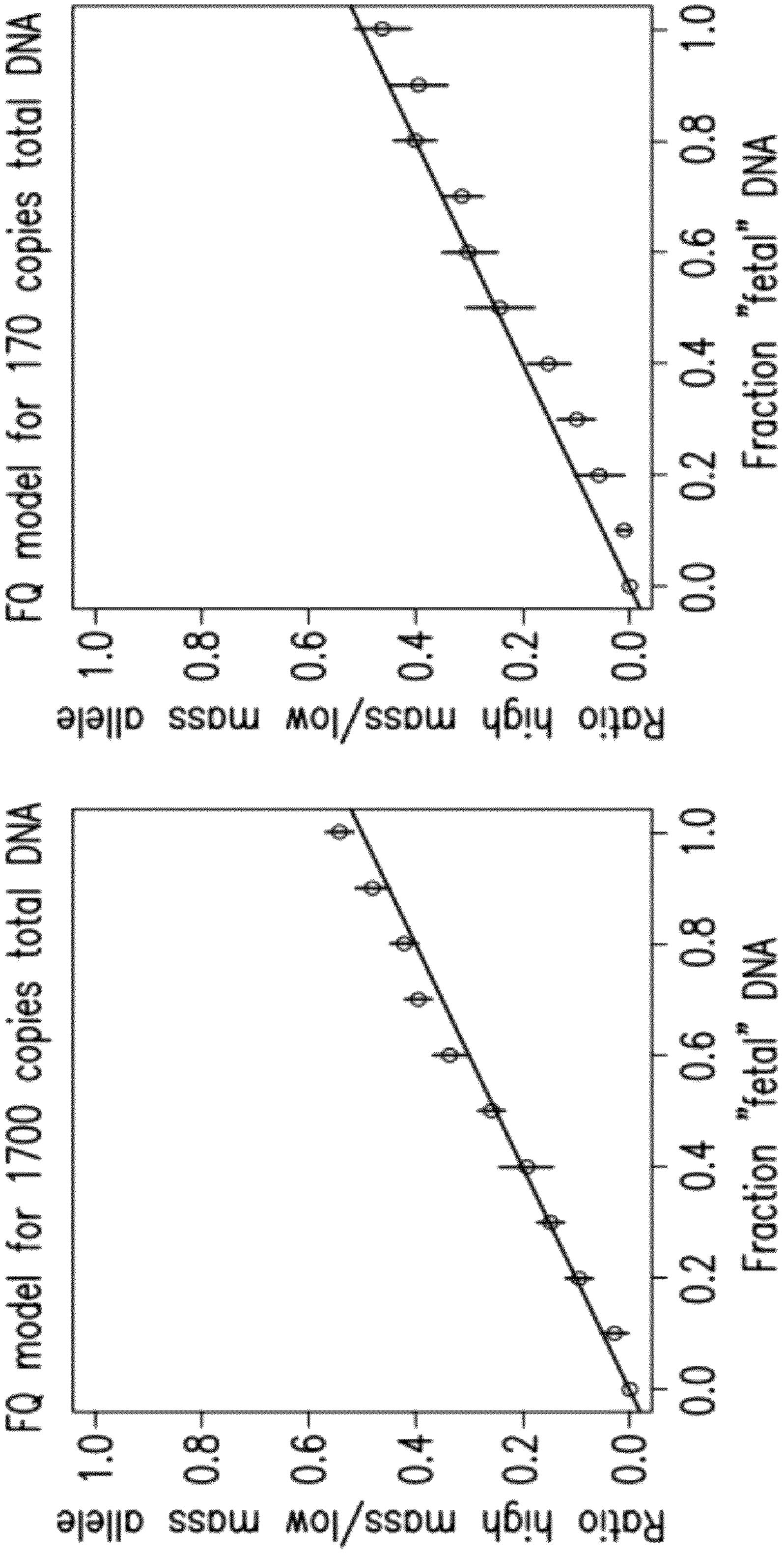
FIG. 8 depicts typical performance results for a qualified fetal identifier. Here the ability of the SNP assay to estimate the quantity of fetal DNA in the background of maternal DNA was verified for a total of 1700 copies and a total of 170 copies using genomic DNA mixtures. Note that the standard deviation of the estimate of fetal DNA increases due to the significant influence of the sampling error at low copy numbers
Figure 9:
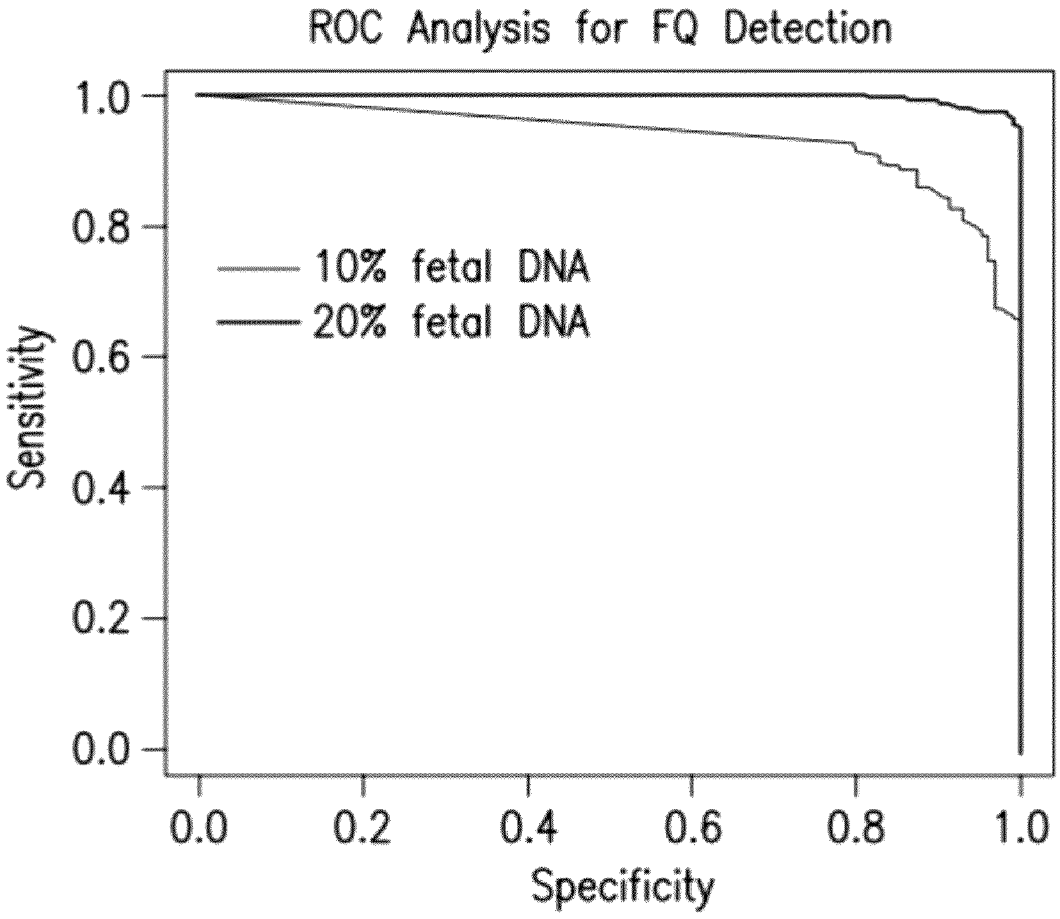
FIG. 9 shows the performance of multiplexed SNP assays (21 assays total) for detection of paternally-inherited alleles in a model system.

FIG. 8 depicts typical performance results for a qualified fetal identifier. Here the ability of the SNP assay to estimate the quantity of fetal DNA in the background of maternal DNA was verified for a total of 1700 copies and a total of 170 copies using genomic DNA mixtures. Note that the standard deviation of the estimate of fetal DNA increases due to the significant influence of the sampling error at low copy numbers Table 2 provides a list of SNPs that were multiplexed at 10+ plexing level and passed all phases of the validation shown in FIG. 7. Application of this assay panel to a model system for the detection of fetal DNA in maternal background showed that paternally-inherited fetal alleles can be detected with a sensitivity of 95% at 100% specificity if the sample preparation method can enrich the relative amount of fetal DNA to 20%. In Table 2, the minor allele frequency (MAF) for each SNP from different ethnic populations is provided. The ethnic populations are defined by the HapMap Project, where CEU represents individuals of Northern and Western Europe descent, HCB represents Han Chinese in Beijing, JAP represents Japanese in Tokyo, and YRI represents the Yoruba in Ibadan, Nigeria.

TABLE 2

| SNP | MAF CEU | MAF HCB | MAF JAP | MAF YRI |
|---|---|---|---|---|
| rs11166512 | 0.43 | 0.41 | 0.50 | 0.49 |
| rs11184494 | 0.50 | 0.40 | 0.48 | 0.50 |
| rs11247894 | 0.43 | 0.39 | 0.32 | 0.44 |
| rs12089156 | 0.46 | 0.49 | 0.44 | 0.43 |
| rs12125888 | 0.40 | 0.43 | 0.48 | 0.43 |
| rs12136370 | 0.42 | 0.48 | 0.42 | 0.48 |
| rs12143315 | 0.40 | 0.42 | 0.42 | 0.42 |
| rs12759642 | 0.39 | 0.48 | 0.48 | 0.42 |
| rs156988 | 0.46 | 0.40 | 0.45 | 0.41 |
| rs2050927 | 0.44 | 0.50 | 0.41 | 0.49 |
| rs213624 | 0.48 | 0.44 | 0.40 | 0.34 |
| rs2454175 | 0.46 | 0.48 | 0.43 | 0.40 |
| rs4329520 | 0.45 | 0.43 | 0.40 | 0.44 |
| rs4487973 | 0.47 | 0.43 | 0.44 | 0.40 |
| rs454782 | 0.48 | 0.40 | 0.41 | 0.46 |
| rs4648888 | 0.33 | 0.30 | 0.33 | 0.46 |
| rs635364 | 0.49 | 0.40 | 0.46 | 0.43 |
| rs660279 | 0.41 | 0.49 | 0.50 | 0.39 |
| rs6687785 | 0.48 | 0.46 | 0.48 | 0.44 |
| rs7551188 | 0.46 | 0.49 | 0.45 | 0.46 |
| rs9431593 | 0.41 | 0.43 | 0.49 | 0.40 |

A multiplexed panel of 16 SNPs was analyzed with maf>0.3 in the same maternal plasma DNA extraction and established a baseline of maternal genotypes by analyzing DNA from PBMCs. Using the maternal genotype information, paternally-inherited alleles were identified in plasma samples and estimated the amount of fetal DNA from the peak area ratio of extension products representing paternally-inherited fetal alleles and maternal alleles.

The AMG XY frequency was then compared with the allele-frequency of paternally-inherited fetal alleles in informative SNPs. This comparison revealed that samples with a positive Y-frequency of 10% (used as a Limit-of-quantitation threshold) or more have significantly higher differences between maternally and paternally-inherited fetal allele-frequencies (p-value <0.001; Fishers' exact test). This data shows that Fetal Identifiers can be used as a non-gender specific approach for identification of the presence of fetal DNA. FIG. 8 exemplifies those results.

Example 3

Multiplex Schemes

The above described RhD, fetal identifier and sex test may be run simultaneously in various multiplex schemes. Exemplary multiplex schemes are provided in FIG. 10. For example, in the Scenario 1 assay, two multiplex reactions are run in parallel. In the MP1, the following reactions are performed: 10 Fetal Identifiers reactions, the RhD 4 reaction, the RhD 10 reaction and the SRY reaction. In the MP2, the following reactions are performed: 11 Fetal Identifiers reactions, the RhD 4 psi quantitative reaction, the RhD 5 reaction and the RhD 7 reaction. Other exemplary multiplex schemes are provided in FIG. 10, but are not intended to limit the scope of the invention.

The PCR primers and extend primers for MP1 and MP2 are provided below in Table 3. Lower case nucleotides in the extend primer sequence represent non-template nucleotides that are added as mass modifiers. Additional fetal identifiers which may be used as described herein are provided in Table 4.

TABLE 3

| Multiplex | Primer Name | Amplification primer | Amplification primer | Extend Primer sequence |
|---|---|---|---|---|
| MP1 | RhD-10-3r-i | ACGTTGGATGACGCTCATGACAGCAAAGTC (SEQ ID NO: 12) | ACGTTGGATGAACTCCATTTTCTCTGACTC (SEQ ID NO: 13) | gGTCTCCAATGTTCGCGCAGGCAC (SEQ ID NO: 15) |
| MP1 | RhD-4-3r-i | ACGTTGGATGCTGCCAAAGCCTCTACACG (SEQ ID NO: 1) | ACGTTGGATGTGGCAGACAAACTGGGTGTC (SEQ ID NO: 2) | GAACGGAGGATAAAGATCAGA (SEQ ID NO: 17) |
| MP1 | rs7551188 | ACGTTGGATGATCCCTGGTTCCTTCCTTAG (SEQ ID NO: 27) | ACGTTGGATGGAGCCTCTCAGTGTCTATAC (SEQ ID NO: 28) | GGACAGATTCTGGGAC (SEQ ID NO: 29) |
| MP1 | rs11247894 | ACGTTGGATGATCCTAGATAGCCCAAAGCC (SEQ ID NO: 30) | ACGTTGGATGGGAGGAAAGAGAAGATTGTG (SEQ ID NO: 31) | CCAAAGCCAAGAATTCA (SEQ ID NO: 32) |
| MP1 | rs6687785 | ACGTTGGATGATGCTGTAAAGAGCCTCAAC (SEQ ID NO: 33) | ACGTTGGATGTTCTCCTCTGACCTGCTTTC (SEQ ID NO: 34) | CCTCAACAGTACACTTAATC (SEQ ID NO: 35) |
| MP1 | rs4487973 | ACGTTGGATGTCAGAGAGTGACAAGACCTG (SEQ ID NO: 36) | ACGTTGGATGGAATGCATGCCAACTTAGGG (SEQ ID NO: 37) | cAGGTCACACAGTTAGGATT (SEQ ID NO: 38) |
| MP1 | rs4648888 | ACGTTGGATGCAGAGAGTCCCCTGTTATTG (SEQ ID NO: 39) | ACGTTGGATGTGCCCAGACCAGAGAGGTCA (SEQ ID NO: 40) | aTGGACCTTCGGAAAGGATA (SEQ ID NO: 41) |
| MP1 | rs12089156 | ACGTTGGATGGCTACATACTATGTGGTCTC (SEQ ID NO: 42) | ACGTTGGATGCCTGCTGGCAACAAATCTTC (SEQ ID NO: 43) | TACTATGTGGTCTCAACTATAT (SEQ ID NO: 44) |
| MP1 | rs2050927 | ACGTTGGATGTTCTAGCTTGCTTCTCCTCC (SEQ ID NO: 45) | ACGTTGGATGTTGGGTGCAGAGTAGTCATC (SEQ ID NO: 46) | TGCTTCTCCTCCATCATCCTTAGC (SEQ ID NO: 47) |
| MP1 | rs12125888 | ACGTTGGATGCAACATCCTGTACATCACTC (SEQ ID NO: 48) | ACGTTGGATGAGACAATTTCTGTCCTCTGG (SEQ ID NO: 49) | TACATGACTATCTCCTCCCTTAGGT (SEQ ID NO: 50) |
| MP1 | rs12143315 | ACGTTGGATGACAGGCATGAGCCATCTTAC (SEQ ID NO: 51) | ACGTTGGATGTGCCATTGGTACAGTCACTC (SEQ ID NO: 52) | CCATCTTACCCAGCCTCTTTCTTCAA (SEQ ID NO: 53) |
| MP1 | rs213624 | ACGTTGGATGTAGGTCAAGCCAAGGCCTC (SEQ ID NO: 54) | ACGTTGGATGTGTCCACCCAGGAGCAGCCA (SEQ ID NO: 55) | gGCCAAGGCCTCGGAGTCTGAACAGTT (SEQ ID NO: 56) |
| MP1 | SRY_5-ib | ACGTTGGATGAGCATCTAGGTAGGTCTTTG (SEQ ID NO: 24) | ACGTTGGATGAGCAACGGGACCGCTACAG (SEQ ID NO: 25) | cGTTACCCGATTGTCCTAC (SEQ ID NO: 57) |
| MP2 | RhD-4-psi-3r-i | ACGTTGGATGGACTATCAGGGCTTGCCCCG (SEQ ID NO: 5) | ACGTTGGATGTGCGAACACGTAGATGTGAC (SEQ ID NO: 58) | cTGCAGACAGACTACCACATGAAC (SEQ ID NO: 18) |
| MP2 | RhD-5_3r-i | ACGTTGGATGAATCGAAAGGAAGAATGCCG (SEQ ID NO: 7) | ACGTTGGATGCTGAGATGGCTGTCACCACG (SEQ ID NO: 8) | ATGCCGTGTTCAACACCTACTATGCT (SEQ ID NO: 19) |
| MP2 | RhD-7-3r-i | ACGTTGGATGAGCTCCATCATGGGCTACAA (SEQ ID NO: 9) | ACGTTGGATGTTGCCGGCTCCGACGGTATC (SEQ ID NO: 10) | CTTGCTGGGTCTGCTTGGAGAGATCA (SEQ ID NO: 22) |
| MP2 | rs660279 | ACGTTGGATGTTTCAGCAACCACTCTGAGC | ACGTTGGATGTGCCCGTAAGTAGGAGAGTG | CTTGATGTGCTTCCCTG |

TABLE 3-continued

| Multiplex | Primer Name | Amplification primer | Amplification primer | Extend Primer sequence |
|---|---|---|---|---|
| | | (SEQ ID NO: 59) | (SEQ ID NO: 60) | (SEQ ID NO: 61) |
| MP2 | rs635364 | ACGTTGGATGGAAATTTCTGGATTACTGGC (SEQ ID NO: 62) | ACGTTGGATGAGAGACTCCATTTGTTTGGG (SEQ ID NO: 63) | TGGATTACTGGCAAAGAC (SEQ ID NO: 64) |
| MP2 | rs9431593 | ACGTTGGATGTTGAGATCAGTGTCGGTTCC (SEQ ID NO: 65) | ACGTTGGATGGCCTCAGTAGTCACATAAGG (SEQ ID NO: 66) | TGTTCCTGACTCTCAAAAT (SEQ ID NO: 67) |
| MP2 | rs11166512 | ACGTTGGATGCTTCATCCACTATATCCACC (SEQ ID NO: 68) | ACGTTGGATGTGACCAGATGTTGGATTAG (SEQ ID NO: 69) | CCACTATATCCACCTTTTCT (SEQ ID NO: 70) |
| MP2 | rs4329520 | ACGTTGGATGGAAAGTTGTCGTGGTAGAGG (SEQ ID NO: 71) | ACGTTGGATGATGTCCACCTCCTGCTCCAC (SEQ ID NO: 72) | GCGTGGTTCTAGACTTATGC (SEQ ID NO: 73) |
| MP2 | rs454782 | ACGTTGGATGCTGTTAAGATGCCAACTCCC (SEQ ID NO: 74) | ACGTTGGATGCTGTCTTCCTCATTGCTCTG (SEQ ID NO: 75) | AACTCCCATATTAGTCCACAG (SEQ ID NO: 76) |
| MP2 | rs12136370 | ACGTTGGATGGAGTAGTTCTTTGCAGTAAGC (SEQ ID NO: 77) | ACGTTGGATGCTCCTGGAAAACAGCAAAAG (SEQ ID NO: 78) | gGCAGTAAGCTATTCTTGGGG (SEQ ID NO: 79) |
| MP2 | rs12759642 | ACGTTGGATGATTCTTCCTGGGACTCAGAC (SEQ ID NO: 80) | ACGTTGGATGGGAAATACCAGCAACCACAG (SEQ ID NO: 81) | caTCGGGATTCCCTGAACAAAA (SEQ ID NO: 82) |
| MP2 | rs11184494 | ACGTTGGATGAGCTGGCCATGTTTATTTGAC (SEQ ID NO: 83) | ACGTTGGATGGCCAATCTATGAAGAATTAC (SEQ ID NO: 84) | ATTTGACTTTCCTACTCCTTAAC (SEQ ID NO: 85) |
| MP2 | rs2454175 | ACGTTGGATGGGAATCAGACCTGTAAACAC (SEQ ID NO: 86) | ACGTTGGATGGCCCAGCAGGACACTTTTAT (SEQ ID NO: 87) | cCTTCAAGGATTGGAATTAGAGT (SEQ ID NO: 88) |
| MP2 | rs156988 | ACGTTGGATGAAAGCTCTGTGATGCGTCTC (SEQ ID NO: 89) | ACGTTGGATGGAAAGGGCTATGTAAGGAGG (SEQ ID NO: 90) | tCGTCTCGGTCCTTCCTTTTCACTT (SEQ ID NO: 91) |

TABLE 4

| Multiplex | SNP_ID | Amplification primer | Amplification primer | Extend Primer sequence |
|---|---|---|---|---|
| W1 | rs10793675 | ACGTTGGATGAAGAGATGAGACAGACTGGG (SEQ ID NO: 92) | ACGTTGGATGCTCTGTATTTATAGCTTTC (SEQ ID NO: 93) | AACGGCTCAACAGTT (SEQ ID NO: 94) |
| W1 | rs1829309 | ACGTTGGATGATCTCTGAGTTGACACCACC (SEQ ID NO: 95) | ACGTTGGATGTTCCTAATCAGGAGAGACCG (SEQ ID NO: 96) | TTGCTTTGGGGAGCAG (SEQ ID NO: 97) |
| W1 | rs660279 | ACGTTGGATGTTTCAGCAACCACTCTGAGC (SEQ ID NO: 59) | ACGTTGGATGTGCCCGTAAGTAGGAGAGTG (SEQ ID NO: 60) | CTTGATGTGCTTCCCTG (SEQ ID NO: 61) |
| W1 | rs635364 | ACGTTGGATGGAAATTTCTGGATTACTGGC (SEQ ID NO: 62) | ACGTTGGATGAGAGACTCCATTTGTTTGGG (SEQ ID NO: 63) | TGGATTACTGGCAAAGAC (SEQ ID NO: 64) |
| W1 | rs9431593 | ACGTTGGATGTTGAGATCAGTGTCGGTTCC (SEQ ID NO: 65) | ACGTTGGATGGCCTCAGTAGTCACATAAGG (SEQ ID NO: 66) | TGTTCCTGACTCTCAAAAT (SEQ ID NO: 67) |
| W1 | rs11166512 | ACGTTGGATGCTTCATCCACTATATCCACC (SEQ ID NO: 68) | ACGTTGGATGTGACCAGATGTTGGATTAG (SEQ ID NO: 69) | CCACTATATCCACCTTTTCT (SEQ ID NO: 70) |
| W1 | rs4329520 | ACGTTGGATGGAAAGTTGTCGTGGTAGAGG (SEQ ID NO: 71) | ACGTTGGATGATGTCCACCTCCTGCTCCAC (SEQ ID NO: 72) | GCGTGGTTCTAGACTTATGC (SEQ ID NO: 73) |
| W1 | rs454782 | ACGTTGGATGCTGTTAAGATGCCAACTCCC (SEQ ID NO: 74) | ACGTTGGATGCTGTCTTCCTCATTGCTCTG (SEQ ID NO: 75) | AACTCCCATATTAGTCCACAG (SEQ ID NO: 76) |
| W1 | rs12136370 | ACGTTGGATGGAGTAGTTCTTTGCAGTAAGC (SEQ ID NO: 77) | ACGTTGGATGCTCCTGGAAAACAGCAAAAG (SEQ ID NO: 78) | gGCAGTAAGCTATTCTTGGGG (SEQ ID NO: 79) |
| W1 | rs12759642 | ACGTTGGATGATTCTTCCTGGGACTCAGAC (SEQ ID NO: 80) | ACGTTGGATGGGAAATACCAGCAACCACAG (SEQ ID NO: 81) | caTCGGGATTCCCTGAACAAAA (SEQ ID NO: 82) |
| W1 | rs11184494 | ACGTTGGATGAGCTGGCCATGTTTATTTGAC (SEQ ID NO: 83) | ACGTTGGATGGCCAATCTATGAAGAATTAC (SEQ ID NO: 84) | ATTTGACTTTCCTACTCCTTAAC (SEQ ID NO: 85) |
| W1 | rs2454175 | ACGTTGGATGGGAATCAGACCTGTAAACAC (SEQ ID NO: 86) | ACGTTGGATGGCCCAGCAGGACACTTTTAT (SEQ ID NO: 87) | cCTTCAAGGATTGGAATTAGAGT (SEQ ID NO: 88) |
| W1 | rs1452628 | ACGTTGGATGGCTTGTGCTTTGTTGTGTGG (SEQ ID NO: 98) | ACGTTGGATGGGTCAAGCAAAGGCTTCAAG (SEQ ID NO: 99) | acatAGTTATTCCTAGGGCTTCTC (SEQ ID NO: 100) |
| W1 | rs156988 | ACGTTGGATGAAAGCTCTGTGATGCGTCTC (SEQ ID NO: 89) | ACGTTGGATGGAAAGGGCTATGTAAGGAGG (SEQ ID NO: 90) | tCGTCTCGGTCCTTCCTTTTCACTT (SEQ ID NO: 91) |
| W1 | rs4570430 | ACGTTGGATGACCCGAGCCAATCAGGTATC (SEQ ID NO: 101) | ACGTTGGATGGCACATGGAGATGAATGGTC (SEQ ID NO: 102) | GGTATCATAAGATACCTATGATGTC (SEQ ID NO: 103) |
| W1 | rs12062414 | ACGTTGGATGTGCGTCAACCTTTCCAGTTC (SEQ ID NO: 104) | ACGTTGGATGGGAAAGTCCTCGACTGTTTG (SEQ ID NO: 105) | ggaaTTTCCAGTTCTATTCCAGCCTC (SEQ ID NO: 106) |
| W1 | rs7545381 | ACGTTGGATGCCAGTCAAGCTAAGGACAAA | ACGTTGGATGGTGAGCACAACTGTGTTCTA | tccCTGAATGACAAAAGGGGAAGATA |

TABLE 4-continued

| Multiplex | SNP_ID | Amplification primer | Amplification primer | Extend Primer sequence |
|---|---|---|---|---|
| | | (SEQ ID NO: 107) | (SEQ ID NO: 108) | (SEQ ID NO: 109) |
| W1 | rs6427673 | ACGTTGGATGGGACTAAAACAGGGCCAAAC (SEQ ID NO: 110) | ACGTTGGATGGTCTCTCTAGTACTAGTAAC (SEQ ID NO: 111) | ccctcGCCAAACTTAGACCAAGGACAAC (SEQ ID NO: 112) |
| W1 | rs10802761 | ACGTTGGATGTCTTCTAAAATGTAGTTATG (SEQ ID NO: 113) | ACGTTGGATGGGATGAGGTTTTGACTAAGC (SEQ ID NO: 114) | AGTTATGAAATAAGTTTTATTCATTTAC (SEQ ID NO: 115) |
| W2 | rs642449 | ACGTTGGATGCCAAAAAACCATGCCCTCTG (SEQ ID NO: 116) | ACGTTGGATGAGATTGCCTCTCCATGTGAC (SEQ ID NO: 117) | CCTCTGCCTCCCCTA (SEQ ID NO: 118) |
| W2 | rs4839419 | ACGTTGGATGCTGCCGCATCCCTTCACAA (SEQ ID NO: 119) | ACGTTGGATGATGTGTTTGTGGCCACTTCC (SEQ ID NO: 120) | CCTTCACAAAGCCGA (SEQ ID NO: 121) |
| W2 | rs9324198 | ACGTTGGATGAAAGGCCTACTGTTTGCTGG (SEQ ID NO: 122) | ACGTTGGATGCAAAATATGTGTGAATCAGC (SEQ ID NO: 123) | cGTTTGCTGGAAGCCT (SEQ ID NO: 124) |
| W2 | rs1192619 | ACGTTGGATGGCTCAACTCTGAACCAATCG (SEQ ID NO: 125) | ACGTTGGATGCCAGGAATGGGCATGTGTTC (SEQ ID NO: 126) | TGGCCAGAAGAAGGAG (SEQ ID NO: 127) |
| W2 | rs4657868 | ACGTTGGATGCTAACCAGGAAAAGACACCC (SEQ ID NO: 128) | ACGTTGGATGCTAGCGTACCCAATGGAATC (SEQ ID NO: 129) | AGACACCCCCATACATTA (SEQ ID NO: 130) |
| W2 | rs6426873 | ACGTTGGATGTAAATCAGGGCTGCCTTCTC (SEQ ID NO: 131) | ACGTTGGATGAAGTGCTAGGGTTACAGGTG (SEQ ID NO: 132) | cccCTGCCTTCTCTTCCAA (SEQ ID NO: 133) |
| W2 | rs438981 | ACGTTGGATGTGTGCAAATTGGCTAACAT (SEQ ID NO: 134) | ACGTTGGATGGAACATTGGTATTTAAACTC (SEQ ID NO: 135) | ATGGACCACAAAAAACTTA (SEQ ID NO: 136) |
| W2 | rs12125888 | ACGTTGGATGAGACAATTTCTGTCCTCTGG (SEQ ID NO: 49) | ACGTTGGATGCAACATCCTGTACATCACTC (SEQ ID NO: 48) | TCTGTCCTCTGGTATCCTCT (SEQ ID NO: 137) |
| W2 | rs3128688 | ACGTTGGATGATCAAGAGGAAAATGGACAG (SEQ ID NO: 138) | ACGTTGGATGGATTTACTCAACTCTCTGGG (SEQ ID NO: 139) | cAAAATGGACAGAAGTTGAA (SEQ ID NO: 140) |
| W2 | rs4987351 | ACGTTGGATGGTGCATGGGCTCATCTAGAC (SEQ ID NO: 141) | ACGTTGGATGCCAAACAGGGCCAATGGTAG (SEQ ID NO: 142) | gCATCTAGACACATTTTGTGC (SEQ ID NO: 143) |
| W2 | rs6692911 | ACGTTGGATGCTATTCCCTCCTCAAAGAGC (SEQ ID NO: 144) | ACGTTGGATGATTAAGATGGGTAGTTAAG (SEQ ID NO: 145) | tccAAGAGCATTTTTCCTCTTC (SEQ ID NO: 146) |
| W2 | rs6684679 | ACGTTGGATGTATGTTACTTGCCTTGGCCC (SEQ ID NO: 147) | ACGTTGGATGTCTTAAGGTGTCTCCCTCTG (SEQ ID NO: 148) | ggaCCACTGAGGAGATACACTA (SEQ ID NO: 149) |
| W2 | rs4320829 | ACGTTGGATGGGTTCTATGGCTTTGGTGAG (SEQ ID NO: 150) | ACGTTGGATGTGCTAGACACTTTAACTGCC (SEQ ID NO: 151) | ggtcACCTCTTTTCATAACAGGA (SEQ ID NO: 152) |
| W2 | rs4658481 | ACGTTGGATGCTGCTAAGCATGAGAGAAAG (SEQ ID NO: 153) | ACGTTGGATGGTGGTAGAAACAAATGTCAGC (SEQ ID NO: 154) | atacGCATGAGAGAAAGGGAAAG (SEQ ID NO: 155) |
| W2 | rs3768458 | ACGTTGGATGCCAAATGTCTTAGTTACAAAG | ACGTTGGATGGAGTTTATGTAATGTCAAC | CTTAGTTACAAAGAAAATTGTGAG |

TABLE 4-continued

| Multiplex | SNP_ID | Amplification primer | Amplification primer | Extend Primer sequence |
|---|---|---|---|---|
| | | (SEQ ID NO: 156) | (SEQ ID NO: 157) | (SEQ ID NO: 158) |
| W2 | rs860954 | ACGTTGGATGTAGCCTTTAGTCTTGATGCC (SEQ ID NO: 159) | ACGTTGGATGCCATTCTTGTATGTTTTGTC (SEQ ID NO: 160) | TCTTGATGCCTTACAAAATAAATAT (SEQ ID NO: 161) |
| W2 | rs10453878 | ACGTTGGATGGAGGAGCTAACAAGTAGGAC (SEQ ID NO: 162) | ACGTTGGATGGGGATATGAATTACAACAGAG (SEQ ID NO: 163) | AAACAAATCCTCCTTTCTTTTAATTC (SEQ ID NO: 164) |
| W2 | rs10753912 | ACGTTGGATGGAGATTATATGTCTCTTTAA (SEQ ID NO: 165) | ACGTTGGATGATTCTTCTAACTTTTAGGC (SEQ ID NO: 166) | GAGATTATATGTCTCTTTAATATTGTC (SEQ ID NO: 167) |
| W2 | rs1637944 | ACGTTGGATGCTAATGCCTCCTTTTCTTCC (SEQ ID NO: 168) | ACGTTGGATGAATAGCAAACAACAGGTGGG (SEQ ID NO: 169) | cccccATATCATTTGCAATTGCATGGTT (SEQ ID NO: 170) |
| W2 | rs4839282 | ACGTTGGATGGAATCCTGGCAGCTCATTAG (SEQ ID NO: 171) | ACGTTGGATGTGGGTTCACATGAGTCTTGC (SEQ ID NO: 172) | gatgTCTCTTAAAGAGCAAAAAGCTAAG (SEQ ID NO: 173) |

Figure 10:
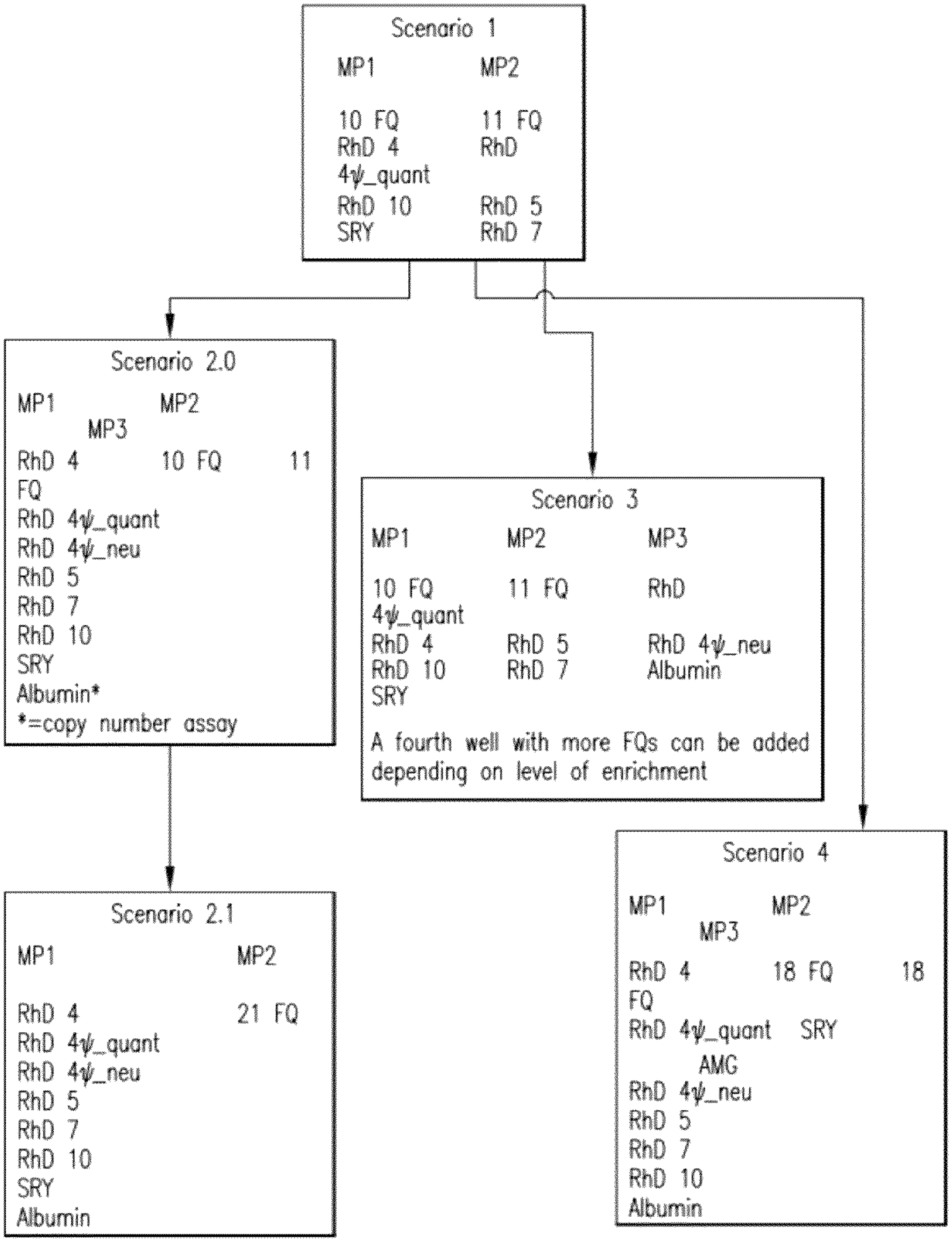
FIG. 10 (provided in duplicate) shows different multiplexed assay schemes of the invention.

Multiplex scheme 3 in FIG. 10 includes an albumin assay which may be performed to determine total copy number of DNA molecules for the human serum albumin gene. The albumin assay is useful to measure how much DNA is loaded into a particular reaction. It acts as an internal control and a guide to the likelihood of success for a particular PCR reaction. For example, if only 400 copies of ALB are measured then the probability of detecting any fetal DNA is very low. Primers for the Albumin assay are provided in FIG. 4.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, yet these modifications and improvements are within the scope and spirit of the invention.

The invention illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the invention claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" is about 1, about 2 and about 3). For example, a weight of "about 100 grams" can include weights between 90 grams and 110 grams. Thus, it should be understood that although the present invention has been specifically disclosed by representative embodiments and optional features, modification and variation of the concepts herein disclosed may be resorted to by those skilled in the art, and such modifications and variations are considered within the scope of this invention.

Embodiments of the invention are set forth in the claims that follow.

What is claimed is:

1. A multiplex method for determining the presence or absence of one or more RhD exons in a fetal nucleic acid, comprising:

simultaneously amplifying fetal nucleic acid from a pregnant female with two or more amplification primers yielding amplification products, contacting the amplification products with extension primers under extension conditions, thereby generating extension products, and determining the presence or absence of an RhD exon in the fetal nucleic acid based on the extension products; wherein:

the extension primers independently comprise a nucleotide sequence of;

gGATAAAGATCAGACAGCAAC (SEQ ID NO: 16)

cTGCAGACAGACTACCACATGAAC (SEQ ID NO: 18)

-continued

| | |
|---|---|
| tTGTCACCACGCTGACTGCTA and | (SEQ ID NO: 21) |
| CTTGCTGGGTCTGCTTGGAGAGATCA | (SEQ ID NO: 22) |

and a nucleotide in lowercase text in the table is not complementary to a RhD sequence nucleotide.

2. The method of claim 1, wherein the fetal nucleic acid is from the blood of the pregnant female.

3. The method of claim 1, wherein the fetal nucleic acid is from serum from the pregnant female.

4. The method of claim 1, wherein the fetal nucleic acid is from plasma from the pregnant female.

5. The method of claim 1, wherein the presence or absence of a 37 base pair insertion in exon 4 of RhD is determined.

6. The method of claim 5, wherein the zygosity of a 37 base pair insertion in exon 4 of RhD is determined.

7. The method of claim 1, wherein the presence or absence of exon 4 of RhD is determined.

8. The method of claim 1, wherein the presence or absence of exon 5 of RhD is determined.

9. The method of claim 1, wherein the presence or absence of exon 7 of RhD is determined.

* * * * *

UNITED STATES PATENT AND TRADEMARK OFFICE

CERTIFICATE OF CORRECTION

PATENT NO. : 8,173,370 B2
APPLICATION NO. : 12/027954
DATED : May 8, 2012
INVENTOR(S) : Paul A. Oeth, Mathias Ehrich and Min S. Lee It is certified that error appears in the above-identified patent and that said Letters Patent is hereby corrected as shown below:

In column 119, line 58, please correct claim 1 to read as follows:

1. A multiplex method for determining the presence or absence of one or more RhD exons in a fetal nucleic acid, comprising:

simultaneously amplifying fetal nucleic acid from a pregnant female with two or more amplification primers yielding amplification products, contacting the amplification products with extension primers under extension conditions, thereby generating extension products, and determining the presence or absence of an RhD exon in the fetal nucleic acid based on the extension products; wherein:

the extension primers independently comprise a nucleotide sequence of[[;]]

gGATAAAGATCAGACAGCAAC (SEQ ID NO: 16)

cTGCAGACAGACTACCACATGAAC (SEQ ID NO: 18)

tTGTCACCACGCTGACTGCTA (SEQ ID NO: 21) and

CTTGCTGGGTCTGCTTGGAGAGATCA (SEQ ID NO: 22)

; and a nucleotide in lowercase text in the table is not complementary to a RhD sequence nucleotide.

Signed and Sealed this
Eleventh Day of September, 2012

David J. Kappos
*Director of the United States Patent and Trademark Office*

SEQUENCE LISTING

```
<160> NUMBER OF SEQ ID NOS: 241

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1

acgttggatg ctgccaaagc ctctacacg                                         29


<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

acgttggatg tggcagacaa actgggtgtc                                        30


<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

acgttggatg agaacggagg ataaagatca gac                                    33


<210> SEQ ID NO 4
<211> LENGTH: 32
```

<212> TYPE: DNA
<213> ORGANISM: Artificial Sequence
<220> FEATURE:
<223> OTHER INFORMATION: Description of Artificial Sequence: Synthetic
primer

<400> SEQUENCE: 4
acgttggatg agccagcatg gcagacaaac tg 32

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 5
acgttggatg gactatcagg gcttgccccg 30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 6
acgttggatg tgcgaacacg tagatgtgca 30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 7
acgttggatg aatcgaaagg aagaatgccg 30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 8
acgttggatg ctgagatggc tgtcaccacg 30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 9
acgttggatg agctccatca tgggctacaa 30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 10
acgttggatg ttgccggctc cgacggtatc 30

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 11
acgttggatg agctccatca tgggctacaa c 31

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 12
acgttggatg acgctcatga cagcaaagtc 30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 13
acgttggatg aactccattt tctctgactc 30

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 14
acgttggatg actccatttt ctctgactc 29

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 15
ggtctccaat gttcgcgcag gcac 24

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
ggataaagat cagacagcaa c 21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
gaacggagga taaagatcag a 21

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
ctgcagacag actaccacat gaac 24

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
atgccgtgtt caacacctac tatgct 26

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
gatggctgtc accacgctga ctgcta 26

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
ttgtcaccac gctgactgct a 21

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
cttgctgggt ctgcttggag agatca 26

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
gttacccgat tgtcctac 18

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
acgttggatg agcatctagg taggtctttg 30

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
acgttggatg agcaacggga ccgctacag 29

<210> SEQ ID NO 26
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
acgttggatg 10

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
acgttggatg atccctggtt ccttccttag 30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 28

```
acgttggatg gagcctctca gtgtctatac                                        30


<210> SEQ ID NO 29
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

ggacagattc tgggac                                                       16


<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

acgttggatg atcctagata gcccaaagcc                                        30


<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

acgttggatg ggaggaaaga gaagattgtg                                        30


<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

ccaaagccaa gaattca                                                      17


<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

acgttggatg atgctgtaaa gagcctcaac                                        30


<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

acgttggatg ttctcctctg acctgctttc                                        30
```

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
cctcaacagt acacttaatc 20

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
acgttggatg tcagagagtg acaagacctg 30

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
acgttggatg gaatgcatgc caacttaggg 30

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
caggtcacac agttaggatt 20

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
acgttggatg cagagagtcc cctgttattg 30

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
acgttggatg tgcccagacc agagaggtca 30

<210> SEQ ID NO 41

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
atggaccttc ggaaaggata 20

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
acgttggatg gctacatact atgtggtctc 30

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
acgttggatg cctgctggca acaaatcttc 30

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
tactatgtgg tctcaactat at 22

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
acgttggatg ttctagcttg cttctcctcc 30

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
acgttggatg ttgggtgcag agtagtcatc 30

<210> SEQ ID NO 47
<211> LENGTH: 24
<212> TYPE: DNA

<213> ORGANISM: Artificial Sequence
<220> FEATURE:
<223> OTHER INFORMATION: Description of Artificial Sequence: Synthetic
primer

<400> SEQUENCE: 47
tgcttctcct ccatcatcct tagc 24

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 48
acgttggatg caacatcctg tacatcactc 30

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 49
acgttggatg agacaatttc tgtcctctgg 30

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 50
tacatgacta tctcctccct taggt 25

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 51
acgttggatg acaggcatga gccatcttac 30

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 52
acgttggatg tgccattggt acagtcactc 30

<210> SEQ ID NO 53
<211> LENGTH: 26
<212> TYPE: DNA
<213> ORGANISM: Artificial Sequence
<220> FEATURE:

<223> OTHER INFORMATION: Description of Artificial Sequence: Synthetic
primer

<400> SEQUENCE: 53
ccatcttacc cagcctcttt cttcaa 26

<210> SEQ ID NO 54
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 54
acgttggatg taggtcaagc caaggcctc 29

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 55
acgttggatg tgtccaccca ggagcagcca 30

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 56
ggccaaggcc tcggagtctg aacagtt 27

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 57
cgttacccga ttgtcctac 19

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 58
acgttggatg tgcgaacacg tagatgtgac 30

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 59
acgttggatg tttcagcaac cactctgagc 30

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 60
acgttggatg tgcccgtaag taggagagtg 30

<210> SEQ ID NO 61
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 61
cttgatgtgc ttccctg 17

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 62
acgttggatg gaaatttctg gattactggc 30

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 63
acgttggatg agagactcca tttgtttggg 30

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 64
tggattactg gcaaagac 18

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 65
acgttggatg ttgagatcag tgtcggttcc 30

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
acgttggatg gcctcagtag tcacataagg 30

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
tgttcctgac tctcaaaat 19

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
acgttggatg cttcatccac tatatccacc 30

<210> SEQ ID NO 69
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
acgttggatg tgaccagatg ttggattag 29

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
ccactatatc caccttttct 20

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
acgttggatg gaaagttgtc gtggtagagg 30

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 72
acgttggatg atgtccacct cctgctccac 30

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 73
gcgtggttct agacttatgc 20

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 74
acgttggatg ctgttaagat gccaactccc 30

<210> SEQ ID NO 75
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 75
acgttggatg ctgtcttcct cattgctctg 30

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 76
aactcccata ttagtccaca g 21

<210> SEQ ID NO 77
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 77
acgttggatg gagtagttct ttgcagtaag c 31

<210> SEQ ID NO 78
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 78
acgttggatg ctcctggaaa acagcaaaag 30

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 79
ggcagtaagc tattcttggg g 21

<210> SEQ ID NO 80
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 80
acgttggatg attcttcctg ggactcagac 30

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 81
acgttggatg ggaaatacca gcaaccacag 30

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 82
catcgggatt ccctgaacaa aa 22

<210> SEQ ID NO 83
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 83
acgttggatg agctggccat gtttatttga c 31

<210> SEQ ID NO 84
<211> LENGTH: 30

-continued

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
acgttggatg gccaatctat gaagaattac 30

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
atttgacttt cctactcctt aac 23

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
acgttggatg ggaatcagac ctgtaaacac 30

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
acgttggatg gcccagcagg acacttttat 30

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ccttcaagga ttggaattag agt 23

<210> SEQ ID NO 89
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
acgttggatg aaagctctgt gatgcgtctc 30

<210> SEQ ID NO 90
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 90
acgttggatg gaaagggcta tgtaaggagg 30

<210> SEQ ID NO 91
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 91
tcgtctcggt ccttcctttt cactt 25

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 92
acgttggatg aagagatgag acagactggg 30

<210> SEQ ID NO 93
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 93
acgttggatg ctctgtattt atagctttc 29

<210> SEQ ID NO 94
<211> LENGTH: 15
<212> TYPE: DNA
<213> ORGANISM: Artificial Sequence
<220> FEATURE:
<223> OTHER INFORMATION: Description of Artificial Sequence: Synthetic
primer

<400> SEQUENCE: 94
aacggctcaa cagtt 15

<210> SEQ ID NO 95
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 95
acgttggatg atctctgagt tgacaccacc 30

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 96
acgttggatg ttcctaatca ggagagaccg 30

<210> SEQ ID NO 97
<211> LENGTH: 16
<212> TYPE: DNA
<213> ORGANISM: Artificial Sequence
<220> FEATURE:
<223> OTHER INFORMATION: Description of Artificial Sequence: Synthetic
primer

<400> SEQUENCE: 97
ttgctttggg gagcag 16

<210> SEQ ID NO 98
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 98
acgttggatg gcttgtgctt tgttgtgtgg 30

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 99
acgttggatg ggtcaagcaa aggcttcaag 30

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 100
acatagttat tcctagggct tctc 24

<210> SEQ ID NO 101
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 101
acgttggatg acccgagcca atcaggtatc 30

<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 102
acgttggatg gcacatggag atgaatggtc 30

<210> SEQ ID NO 103
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 103
ggtatcataa gatacctatg atgtc 25

<210> SEQ ID NO 104
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
acgttggatg tgcgtcaacc tttccagttc 30

<210> SEQ ID NO 105
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
acgttggatg ggaaagtcct cgactgtttg 30

<210> SEQ ID NO 106
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
ggaatttcca gttctattcc agcctc 26

<210> SEQ ID NO 107
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
acgttggatg ccagtcaagc taaggacaaa 30

<210> SEQ ID NO 108
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 108
acgttggatg gtgagcacaa ctgtgttcta 30

<210> SEQ ID NO 109
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
tccctgaatg acaaaagggg aagata 26

<210> SEQ ID NO 110
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 110
acgttggatg ggactaaaac agggccaaac 30

<210> SEQ ID NO 111
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 111
acgttggatg gtctctctag tactagtaac 30

<210> SEQ ID NO 112
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 112
ccctcgccaa acttagacca aggacaac 28

<210> SEQ ID NO 113
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 113
acgttggatg tcttctaaaa tgtagttatg 30

<210> SEQ ID NO 114
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 114
acgttggatg ggatgaggtt ttgactaagc 30

<210> SEQ ID NO 115
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 115
agttatgaaa taagttttat tcatttac 28

<210> SEQ ID NO 116
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
acgttggatg ccaaaaaacc atgccctctg 30

<210> SEQ ID NO 117
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
acgttggatg agattgcctc tccatgtgac 30

<210> SEQ ID NO 118
<211> LENGTH: 15
<212> TYPE: DNA
<213> ORGANISM: Artificial Sequence
<220> FEATURE:
<223> OTHER INFORMATION: Description of Artificial Sequence: Synthetic primer

<400> SEQUENCE: 118
cctctgcctc cccta 15

<210> SEQ ID NO 119
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
acgttggatg ctgccgcatc ccttcacaa 29

<210> SEQ ID NO 120
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
acgttggatg atgtgtttgt ggccacttcc 30

<210> SEQ ID NO 121

<211> LENGTH: 15
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
ccttcacaaa gccga 15

<210> SEQ ID NO 122
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 122
acgttggatg aaaggcctac tgtttgctgg 30

<210> SEQ ID NO 123
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 123
acgttggatg caaaatatgt gtgaatcagc 30

<210> SEQ ID NO 124
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 124
cgtttgctgg aagcct 16

<210> SEQ ID NO 125
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 125
acgttggatg gctcaactct gaaccaatcg 30

<210> SEQ ID NO 126
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 126
acgttggatg ccaggaatgg gcatgtgttc 30

<210> SEQ ID NO 127
<211> LENGTH: 16
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 127
tggccagaag aaggag 16

<210> SEQ ID NO 128
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
acgttggatg ctaaccagga aaagacaccc 30

<210> SEQ ID NO 129
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
acgttggatg ctagcgtacc caatggaatc 30

<210> SEQ ID NO 130
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
agacaccccc atacatta 18

<210> SEQ ID NO 131
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
acgttggatg taaatcaggg ctgccttctc 30

<210> SEQ ID NO 132
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
acgttggatg aagtgctagg gttacaggtg 30

<210> SEQ ID NO 133
<211> LENGTH: 19
<212> TYPE: DNA
<213> ORGANISM: Artificial Sequence
<220> FEATURE:

<223> OTHER INFORMATION: Description of Artificial Sequence: Synthetic
primer

<400> SEQUENCE: 133
cccctgcctt ctcttccaa 19

<210> SEQ ID NO 134
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 134
acgttggatg tgtgcaaatt ggctaacat 29

<210> SEQ ID NO 135
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 135
acgttggatg gaacattggt atttaaactc 30

<210> SEQ ID NO 136
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 136
atggaccaca aaaaactta 19

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 137
tctgtcctct ggtatcctct 20

<210> SEQ ID NO 138
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 138
acgttggatg atcaagagga aaatggacag 30

<210> SEQ ID NO 139
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 139
acgttggatg gatttactca actctctggg 30

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 140
caaaatggac agaagttgaa 20

<210> SEQ ID NO 141
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 141
acgttggatg gtgcatgggc tcatctagac 30

<210> SEQ ID NO 142
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 142
acgttggatg ccaaacaggg ccaatggtag 30

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 143
gcatctagac acattttgtg c 21

<210> SEQ ID NO 144
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 144
acgttggatg ctattccctc ctcaaagagc 30

<210> SEQ ID NO 145
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 145
acgttggatg attaagatgg gtagttaag 29

<210> SEQ ID NO 146
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 146
tccaagagca tttttcctct tc 22

<210> SEQ ID NO 147
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 147
acgttggatg tatgttactt gccttggccc 30

<210> SEQ ID NO 148
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 148
acgttggatg tcttaaggtg tctccctctg 30

<210> SEQ ID NO 149
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 149
ggaccactga ggagatacac ta 22

<210> SEQ ID NO 150
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 150
acgttggatg ggttctatgg ctttggtgag 30

<210> SEQ ID NO 151
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 151
acgttggatg tgctagacac tttaactgcc 30

<210> SEQ ID NO 152
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 152
ggtcacctct tttcataaca gga 23

<210> SEQ ID NO 153
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 153
acgttggatg ctgctaagca tgagagaaag 30

<210> SEQ ID NO 154
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 154
acgttggatg gtggtagaaa caaatgtcag c 31

<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 155
atacgcatga gagaaaggga aag 23

<210> SEQ ID NO 156
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 156
acgttggatg ccaaatgtct tagttacaaa g 31

<210> SEQ ID NO 157
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 157
acgttggatg gagtttatgt aatgtcaac 29

<210> SEQ ID NO 158
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 158
cttagttaca aagaaaattg tgag 24

<210> SEQ ID NO 159
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 159
acgttggatg tagcctttag tcttgatgcc 30

<210> SEQ ID NO 160
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 160
acgttggatg ccattcttgt atgttttgtc 30

<210> SEQ ID NO 161
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 161
tcttgatgcc ttacaaaata aatat 25

<210> SEQ ID NO 162
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 162
acgttggatg gaggagctaa caagtaggac 30

<210> SEQ ID NO 163
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 163
acgttggatg gggatatgaa ttacaacaga g 31

<210> SEQ ID NO 164
<211> LENGTH: 26

<212> TYPE: DNA
<213> ORGANISM: Artificial Sequence
<220> FEATURE:
<223> OTHER INFORMATION: Description of Artificial Sequence: Synthetic primer

<400> SEQUENCE: 164
aaacaaatcc tcctttcttt taattc 26

<210> SEQ ID NO 165
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 165
acgttggatg gagattatat gtctctttaa 30

<210> SEQ ID NO 166
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 166
acgttggatg attcttctaa cttttaggc 29

<210> SEQ ID NO 167
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 167
gagattatat gtctctttaa tattgtc 27

<210> SEQ ID NO 168
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 168
acgttggatg ctaatgcctc cttttcttcc 30

<210> SEQ ID NO 169
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 169
acgttggatg aatagcaaac aacaggtggg 30

<210> SEQ ID NO 170
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 170
cccccatatc atttgcaatt gcatggtt 28

<210> SEQ ID NO 171
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 171
acgttggatg gaatcctggc agctcattag 30

<210> SEQ ID NO 172
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 172
acgttggatg tgggttcaca tgagtcttgc 30

<210> SEQ ID NO 173
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 173
gatgtctctt aaagagcaaa aagctaag 28

<210> SEQ ID NO 174
<211> LENGTH: 359
<212> TYPE: DNA
<213> ORGANISM: Homo sapiens

<400> SEQUENCE: 174
gtaagctctg aacaccagtc tcatggcttc aagtcacacc tcctaagtga agctctgaac 60
tttctccaag gactatcagg gcttgccccg ggcagaggat gccgacactc actgctctta 120
ctgggtttta ttgcagacag actaccacat gaacatgatg cacatctacg tgttcgcagc 180
ctattttggg ctgtctgtgg cctggtgcct gccaaagcct ctacccgagg gaacggagga 240
taaagatcag acagcaacga tacccagttt gtctgccatg ctgggtaagg acaaggtggg 300
gtgagtggtc tcctacttgg gctgagcaga atggctcaga aaaggctctg gctgaaaaa 359

<210> SEQ ID NO 175
<211> LENGTH: 360
<212> TYPE: DNA
<213> ORGANISM: Homo sapiens

<400> SEQUENCE: 175
gtaagctctg aacaccagtc tcgtggcttc aagtcacacc tcctaagtga agctctgaac 60
tttctccaag gaccatcagg gctttcccct gggcagagga tgccgacact cactgctctt 120
actgggtttt attgcagaca gactaccaca tgaacctgag gcacttctac gtgttcgcag 180
cctattttgg gctgactgtg gcctggtgcc tgccaaagcc tctacccaag ggaacggagg 240
ataatgatca gagagcaacg atacccagtt tgtctgccat gctgggtaag gacaaggtgg 300
ggtgagtggt ctcatacttg ggctgagcag aatggctcag aaaaggctct ggctgaaaaa 360

<210> SEQ ID NO 176
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 176
ttactgggtt ttattgcaga cagactacca catgaac 37

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 177
gataaagatc agacagcaac 20

<210> SEQ ID NO 178
<211> LENGTH: 240
<212> TYPE: DNA
<213> ORGANISM: Homo sapiens

<400> SEQUENCE: 178
tttggagcag gagtgtgatt ctggccaacc accctctctg gcccccaggc gccctcttct 60
tgtggatgtt ctggccaagt ttcaactctg ctctgctgag aagtccaatc gaaaggaaga 120
atgccgtgtt caacacctac tatgctgtag cagtcagcgt ggtgacagcc atctcagggt 180
catccttggc tcacccccaa gggaagatca gcaaggtgag cagggcgctg cccttgggca 240

<210> SEQ ID NO 179
<211> LENGTH: 240
<212> TYPE: DNA
<213> ORGANISM: Homo sapiens

<400> SEQUENCE: 179
tttggagcag gagtgtgatt ctggccaacc accctctctg gcccccaggc gccctcttct 60
tgtggatgtt ctggccaagt gtcaactctg ctctgctgag aagtccaatc caaaggaaga 120
atgccatgtt caacacctac tatgctctag cagtcagtgt ggtgacagcc atctcagggt 180
catccttggc tcacccccaa aggaagatca gcatggtgag cagggcgctg cccttgggca 240

<210> SEQ ID NO 180
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 180
acgttggatg tgtggctggg ctgatctgcg 30

<210> SEQ ID NO 181

<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 181
acgttggatg ttcagccaaa gcagaggagg 30

<210> SEQ ID NO 182
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 182
agttgtctag tttcttaccg gcagg 25

<210> SEQ ID NO 183
<211> LENGTH: 240
<212> TYPE: DNA
<213> ORGANISM: Homo sapiens

<400> SEQUENCE: 183
gtgttctctc tctaccttgc ttcctttacc cacacgctat ttctttgcag acttatgtgc 60
acagtgcggt gttggcagga ggcgtggctg tgggtacctc gtgtcacctg atcccttctc 120
cgtggcttgc catggtgctg ggtcttgtgg ctgggctgat ctccgtcggg ggagccaagt 180
acctgccggt aagaaactag acaactaacc tcctctgctt tggctgaagg ccagcaggac 240

<210> SEQ ID NO 184
<211> LENGTH: 240
<212> TYPE: DNA
<213> ORGANISM: Homo sapiens

<400> SEQUENCE: 184
gtgttctctc tctaccttgc ttcctttacc cacacgctat ttctttgcag acttatgtgc 60
acagtgcggt gttggcagga ggcgtggctg tgggtacctc gtgtcacctg atcccttctc 120
cgtggcttgc catggtgctg ggtcttgtgg ctgggctgat ctccatcggg ggagccaagt 180
gcctgccggt aagaaactag acaactaatg ctctctgctt tggctgaagg ccagcaggac 240

<210> SEQ ID NO 185
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 185
tgctgggtct gcttggagag atca 24

<210> SEQ ID NO 186
<211> LENGTH: 240
<212> TYPE: DNA
<213> ORGANISM: Homo sapiens

<400> SEQUENCE: 186
tgccaatctg cttataataa cacttgtcca caggggtgtt gtaaccgagt gctggggatt 60
ccccacagct ccatcatggg ctacaacttc agcttgctgg gtctgcttgg agagatcatc 120
tacattgtgc tgctggtgct tgataccgtc ggagccggca atggcatgtg ggtcactggg 180
cttacccccc atccccttaa cactcccctc caactcagga agaaatgtgt gcagagtcct 240

<210> SEQ ID NO 187
<211> LENGTH: 240
<212> TYPE: DNA
<213> ORGANISM: Homo sapiens

<400> SEQUENCE: 187
tgccaatctg cttataataa cacttgtcca caggtgtgtt gtaaccgagt gctggggatt 60
caccacatct ccgtcatgca ctccatcttc agcttgctgg gtctgcttgg agagatcacc 120
tacattgtgc tgctggtgct tcatactgtc tggaacggca atggcatgtg ggtcactggg 180
cttacccccc atccccttaa cactcccctc caactcagga agaaatgtgt gcagagtcct 240

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 188
gtctccaatg ttcgcgcagg cac 23

<210> SEQ ID NO 189
<211> LENGTH: 240
<212> TYPE: DNA
<213> ORGANISM: Homo sapiens

<400> SEQUENCE: 189
agatcaagcc aaaatcagta tgtgggttca tctgcaataa aaatgtttgt tttgctttta 60
cagtttcctc atttggctgt tggattttaa gcaaaagcat ccaagaaaaa caaggcctgt 120
tcaaaaacaa gacaacttcc tctcactgtt gcctgcattt gtacgtgaga aacgctcatg 180
acagcaaagt ctccaatgtt cgcgcaggca ctggagtcag agaaaatgga gttgaatcct 240

<210> SEQ ID NO 190
<211> LENGTH: 232
<212> TYPE: DNA
<213> ORGANISM: Homo sapiens

<400> SEQUENCE: 190
agatcaagcc aaaatcagta tgtgggttca tctgcaataa aaatgtttgt tttgctttta 60
cagtttcctc atttggctgt tggattttaa gcaaaagcat ccaagaaaaa caaggcctgt 120
tcaaaaacaa gacaacttcc tctcactgtt gcctgcattt gtacgtgaga aacgctcatg 180
acagcaaagt ctccttatgt ataatgaaac aaggtcagag acagatttga ta 232

<210> SEQ ID NO 191
<211> LENGTH: 1960
<212> TYPE: DNA
<213> ORGANISM: Homo sapiens

<400> SEQUENCE: 191
tttctaaaag tcaaatgtta gccatcctag aagttgggca taaaatactt gtaagtatat 60
gctaatattc tgatacttaa tgcctgtgaa aaatgtgtat agaattttca atttttaaat 120
agaagtgaag aaaaagcgat aataattact ataaattcaa tatgcagtta tgtatgtatg 180

-continued

```
tgtgtggtta agacaattag gttctcatta agctttgttt ttttaaagat aacatacaca    240

tatattgata atgataaaca attcatatag ctttttgtgt cctctcgttt tgtgacataa    300

aaggtcaatg aaaaaattgg cgattaagtc aaattcgcat ttttcaggac agcagtagag    360

cagtcaggga ggcagatcag cagggcaagt agtcaacgtt actgaattac catgttttgc    420

ttgagaatga atacattgtc agggtactag gggtaggct ggttgggcgg ggttgagggg    480

gtgttgaggg cggagaaatg caagtttcat tacaaaagtt aacgtaacaa agaatctggt    540

agaagtgagt tttggatagt aaaataagtt tcgaactctg gcacctttca attttgtcgc    600

actctccttg tttttgacaa tgcaatcata tgcttctgct atgttaagcg tattcaacag    660

cgatgattac agtccagctg tgcaagagaa tattcccgct ctccggagaa gctcttcctt    720

cctttgcact gaaagctgta actctaagta tcagtgtgaa acgggagaaa acagtaaagg    780

caacgtccag gatagagtga agcgacccat gaacgcattc atcgtgtggt ctcgcgatca    840

gaggcgcaag atggctctag agaatcccag aatgcgaaac tcagagatca gcaagcagct    900

gggataccag tggaaaatgc ttactgaagc cgaaaaatgg ccattcttcc aggaggcaca    960

gaaattacag gccatgcaca gagagaaata cccgaattat aagtatcgac ctcgtcggaa   1020

ggcgaagatg ctgccgaaga attgcagttt gcttcccgca gatcccgctt cggtactctg   1080

cagcgaagtg caactggaca acaggttgta cagggatgac tgtacgaaag ccacacactc   1140

aagaatggag caccagctag gccacttacc gcccatcaac gcagccagct caccgcagca   1200

acgggaccgc tacagccact ggacaaagct gtaggacaat cgggtaacat tggctacaaa   1260

gacctaccta gatgctcctt tttacgataa cttacagccc tcactttctt atgtttagtt   1320

tcaatattgt tttcttttct ctggctaata aaggccttat tcatttcagt tttactggta   1380

tttcatttta aacttaattt caagacaagt tgtgtcaaca cgattaacat gcaaagaaat   1440

aagacatcca gaagtgagcc tgcctatgtt tgtggccgtc agagtactaa cttgatacaa   1500

acggacactg tggcttactt taaatgctct aatgagaaac acacttgaaa attgtaccaa   1560

aaaaaatcac acttctatat gcagcgtgtt aagcagtcct ctctagaccg tgtattcatt   1620

ggtctttcag ctactttgta cgtgtctata aattgcaggt aactaaggaa tggatatgta   1680

agcaggatca aacttgtttc tttctctccc cttcacgctg tggaaaaaac cagttttacc   1740

tccacttgca attcagttcc tttactccat ataaatccaa acggttgaca tttcctttca   1800

actagttata aaatgcctct ggtaaaacaa aatatttaat tccttgtcat ttttgtatct   1860

ctatgaaact tatcattttg cctttcttct gaaaactatc ttttaaaatg gcaatctact   1920

tgtttccatg gcctattaac ttttaagcct gtggaatgaa                         1960
```

<210> SEQ ID NO 192
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 192

```
acgttggatg cgcatttttc aggacagcag                                      30
```

<210> SEQ ID NO 193
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 193
acgttggatg gtaacgttga ctacttgccc 30

<210> SEQ ID NO 194
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 194
caggacagca gtagagca 18

<210> SEQ ID NO 195
<211> LENGTH: 67
<212> TYPE: DNA
<213> ORGANISM: Homo sapiens

<400> SEQUENCE: 195
cgcatttttc aggacagcag tagagcactc agggaggcag atcagcaggg caagtagtca 60
acgttac 67

<210> SEQ ID NO 196
<211> LENGTH: 67
<212> TYPE: DNA
<213> ORGANISM: Homo sapiens

<400> SEQUENCE: 196
gtaacgttga ctacttgccc tgctgatctg cctccctgag tgctctactg ctgtcctgaa 60
aaatgcg 67

<210> SEQ ID NO 197
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 197
acgttggatg agatggctct agagaatccc 30

<210> SEQ ID NO 198
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 198
acgttggatg gcattttcca ctggtatccc 30

<210> SEQ ID NO 199
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 199
tcccagaatg cgaaactc 18

<210> SEQ ID NO 200
<211> LENGTH: 72
<212> TYPE: DNA
<213> ORGANISM: Homo sapiens

<400> SEQUENCE: 200
agatggctct agagaatccc agaatgcgaa actctgagat cagcaagcag ctgggatacc 60
agtggaaaat gc 72

<210> SEQ ID NO 201
<211> LENGTH: 72
<212> TYPE: DNA
<213> ORGANISM: Homo sapiens

<400> SEQUENCE: 201
gcattttcca ctggtatccc agctgcttgc tgatctcaga gtttcgcatt ctgggattct 60
ctagagccat ct 72

<210> SEQ ID NO 202
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 202
cgttacccga ttgtcctac 19

<210> SEQ ID NO 203
<211> LENGTH: 80
<212> TYPE: DNA
<213> ORGANISM: Homo sapiens

<400> SEQUENCE: 203
agcaacggga ccgctacagc cactggacaa agcagtagga caatcgggta acattggcta 60
caaagaccta cctagatgct 80

<210> SEQ ID NO 204
<211> LENGTH: 80
<212> TYPE: DNA
<213> ORGANISM: Homo sapiens

<400> SEQUENCE: 204
agcatctagg taggtctttg tagccaatgt tacccgattg tcctactgct ttgtccagtg 60
gctgtagcgg tcccgttgct 80

<210> SEQ ID NO 205
<211> LENGTH: 95
<212> TYPE: DNA
<213> ORGANISM: Homo sapiens

<400> SEQUENCE: 205
tcacgaggtc aggagatcga gacaatcctg gctaacatgg tgaaaccccg tctctactaa 60
aaatacaaca aattcgtagg gccaggtggc aggtg 95

<210> SEQ ID NO 206
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 206
acgttggatg aggagatcga gacaatcctg 30

<210> SEQ ID NO 207
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 207
acgttggatg ctggccctac gaatttgttg 30

<210> SEQ ID NO 208
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 208
cggccctacg aatttgttgt attttt 26

<210> SEQ ID NO 209
<211> LENGTH: 81
<212> TYPE: DNA
<213> ORGANISM: Homo sapiens

<400> SEQUENCE: 209
gctacttctc taccttatgg cagggacttg tcgctaggca atggtggcat tcattgtgat 60
gctagccaga gctcacagct c 81

<210> SEQ ID NO 210
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 210
acgttggatg taccttatgg cagggacttg 30

<210> SEQ ID NO 211
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 211
acgttggatg ctctggctag catcacaatg 30

<210> SEQ ID NO 212
<211> LENGTH: 16
<212> TYPE: DNA
<213> ORGANISM: Artificial Sequence
<220> FEATURE:
<223> OTHER INFORMATION: Description of Artificial Sequence: Synthetic
primer

<400> SEQUENCE: 212
gggacttgtc gctagg 16

<210> SEQ ID NO 213
<211> LENGTH: 212
<212> TYPE: DNA
<213> ORGANISM: Homo sapiens

<400> SEQUENCE: 213
acctcatcct gggcaccctg gttatatcaa cttcagctat gaggtaattt ttctctttac 60
taattttgac cattgtttgc gttaacaatg ccctgggctc tgtaaagaat agtgtgttga 120
ttctttatcc cagatgtttc tcaagtggtc ctgattttac agttcctacc accagcttcc 180
cagtttaagc tctgatggtt ggcctcaagc ct 212

<210> SEQ ID NO 214
<211> LENGTH: 218
<212> TYPE: DNA
<213> ORGANISM: Homo sapiens

<400> SEQUENCE: 214
acctcatcct gggcaccctg gttatatcaa cttcagctat gaggtaattt ttctctttac 60
taattttgat cactgtttgc attagcagtc ccctgggctc tgtaaagaat agtgggtgga 120
ttcttcatcc caaataaagt ggtttctcaa gtggtcccaa ttttacagtt cctaccatca 180
gcttcccagt ttaagctctg atggttggcc tcaagcct 218

<210> SEQ ID NO 215
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 215
acgttggatg ccctgggctc tgtaaagaat 30

<210> SEQ ID NO 216
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 216
acgttggatg aggcttgagg ccaaccatca g 31

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 217
ttcttcatcc caaataaagt 20

<210> SEQ ID NO 218
<211> LENGTH: 122
<212> TYPE: DNA

<213> ORGANISM: Homo sapiens

<400> SEQUENCE: 218
ccctgggctc tgtaaagaat agtgtgttga ttctttatcc cagaagtttc tcaagtggtc 60
ctgattttac agttcctacc accagcttcc cagtttaagc tctgatggtt ggcctcaagc 120
ct 122

<210> SEQ ID NO 219
<211> LENGTH: 122
<212> TYPE: DNA
<213> ORGANISM: Homo sapiens

<400> SEQUENCE: 219
aggcttgagg ccaaccatca gagcttaaac tgggaagctg gtggtaggaa ctgtaaaatc 60
aggaccactt gagaaacttc tgggataaag aatcaacaca ctattcttta cagagcccag 120
gg 122

<210> SEQ ID NO 220
<211> LENGTH: 128
<212> TYPE: DNA
<213> ORGANISM: Homo sapiens

<400> SEQUENCE: 220
ccctgggctc tgtaaagaat agtgggtgga ttcttcatcc caaataaagt cgtttctcaa 60
gtggtcccaa ttttacagtt cctaccatca gcttcccagt ttaagctctg atggttggcc 120
tcaagcct 128

<210> SEQ ID NO 221
<211> LENGTH: 128
<212> TYPE: DNA
<213> ORGANISM: Homo sapiens

<400> SEQUENCE: 221
aggcttgagg ccaaccatca gagcttaaac tgggaagctg atggtaggaa ctgtaaaatt 60
gggaccactt gagaaacgac tttatttggg atgaagaatc cacccactat tctttacaga 120
gcccaggg 128

<210> SEQ ID NO 222
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 222
acgttggatg tatcaacttc agctatgagg 30

<210> SEQ ID NO 223
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 223
acgttggatg cactattctt tacagagc 28

<210> SEQ ID NO 224

<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 224
ctttacagag cccaggg 17

<210> SEQ ID NO 225
<211> LENGTH: 90
<212> TYPE: DNA
<213> ORGANISM: Homo sapiens

<400> SEQUENCE: 225
tatcaacttc agctatgagg taatttttct ctttactaat tttgaycayt gtttgcrtta 60
rcartaccct gggctctgta aagaatagtg 90

<210> SEQ ID NO 226
<211> LENGTH: 90
<212> TYPE: DNA
<213> ORGANISM: Homo sapiens

<400> SEQUENCE: 226
cactattctt tacagagccc agggtartgr taargcaaac aytgytcaaa attagtaaag 60
agaaaaatta cctcatagct gaagttgata 90

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 227
ccctgggctc tgtaaagaat 20

<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 228
gagcttaaac tgggaagctg 20

<210> SEQ ID NO 229
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 229
ccctgggctc tgtaaagaat agt 23

<210> SEQ ID NO 230
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 230
ttcttcatcc caaataaagt g 21

<210> SEQ ID NO 231
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 231
ccctgggctc tgtaaagaat agtg 24

<210> SEQ ID NO 232
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 232
ctgggctctg taaagaatag t 21

<210> SEQ ID NO 233
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 233
ctgggctctg taaagaatag tg 22

<210> SEQ ID NO 234
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 234
caggacagca gtagagcag 19

<210> SEQ ID NO 235
<211> LENGTH: 68
<212> TYPE: DNA
<213> ORGANISM: Homo sapiens

<400> SEQUENCE: 235
gctcagtatc ttcagcagtg tccatttgaa gatcatgtaa aattagtgaa tgaagtaact 60
gaatttgc 68

<210> SEQ ID NO 236
<211> LENGTH: 68
<212> TYPE: DNA
<213> ORGANISM: Homo sapiens

<400> SEQUENCE: 236
gctcagtatc ttcagcagtg tccatttgaa gatcatgtaa aattagtgaa tgaagtaact 60

```
gaatttgc                                                            68


<210> SEQ ID NO 237
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237

acgttggatg cagtatcttc agcagtgtcc                                    30


<210> SEQ ID NO 238
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238

acgttggatg gcaaattcag ttacttcatt c                                  31


<210> SEQ ID NO 239
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239

cagtgtccat ttgaagatc                                                19


<210> SEQ ID NO 240
<211> LENGTH: 65
<212> TYPE: DNA
<213> ORGANISM: Homo sapiens

<400> SEQUENCE: 240

cagtatcttc agcagtgtcc atttgaagat cttgtaaaat tagtgaatga agtaactgaa     60

tttgc                                                               65


<210> SEQ ID NO 241
<211> LENGTH: 65
<212> TYPE: DNA
<213> ORGANISM: Homo sapiens

<400> SEQUENCE: 241

gcaaattcag ttacttcatt cactaatttt acaagatctt caaatggaca ctgctgaaga     60

tactg                                                               65
```